US012709608B2

(12) United States Patent
Srinivasan et al.

(10) Patent No.: US 12,709,608 B2
(45) Date of Patent: Aug. 18, 2026

(54) 4-AMINO PYRIMIDINE COMPOUNDS FOR THE TREATMENT OF CANCER

(71) Applicants: University of Rochester, Rochester, NY (US); Ann & Robert H. Lurie Children's Hospital of Chicago, Chicago, IL (US)

(72) Inventors: Venkatesan Srinivasan, Madison, WI (US); Frank H. Ebetino, Rochester, NY (US); Rintaro Hashizume, Chicago, IL (US); Robert K. Boeckman, Jr., Glenfield, NY (US)

(73) Assignees: University of Rochester, Rochester, NY (US); Ann & Robert H. Lurie Children's Hospital of Chicago, Chicago, IL (US)

( * ) Notice: Subject to any disclaimer, the term of this patent is extended or adjusted under 35 U.S.C. 154(b) by 356 days.

(21) Appl. No.: 18/052,838

(22) Filed: Nov. 4, 2022

(65) Prior Publication Data

US 2023/0150976 A1 May 18, 2023

Related U.S. Application Data

(60) Provisional application No. 63/276,555, filed on Nov. 6, 2021.

(51) Int. Cl.
*A61P 35/00* (2006.01)
*C07D 401/14* (2006.01)

(52) U.S. Cl.
CPC ............ *C07D 401/14* (2013.01); *A61P 35/00* (2018.01)

(58) Field of Classification Search
CPC ............................... C07D 401/14; A61P 35/00
See application file for complete search history.

(56) References Cited

U.S. PATENT DOCUMENTS

2021/0069230 A1* 3/2021 Rees .................... A61K 31/341

FOREIGN PATENT DOCUMENTS

CN 106608869 A * 5/2017 ........... C07D 401/14

OTHER PUBLICATIONS

Lapin et al. Genomic Insights into Diffuse Intrinsic Pontine Glioma, (Frontiers in Oncology), Mar. 2017, pp. 1-7, [online], [retrieved on Jan. 26, 2024]. Retrieved from the internet <URL: https://www.frontiersin.org/journals/oncology/articles/10.3389/fonc.2017.00057/full >. (Year: 2017).*
CN106608869 A Machine Translation (Year: 2017).*
Lapin et al. Genomic Insights into Diffuse Intrinsic Pontine Glioma, (Frontiers in Oncology), Mar. 2017, pp. 1-7 (Year: 2017).*
Hashizume et al: "Pharmacologic inhibition of histone demethylation as a therapy for pediatric brainstem glioma", Nature Medicine, Received Apr. 24; accepted Sep. 11; published online Nov. 17, 2014; doi: 10.1038/hm.3716, pp. 1-5.

* cited by examiner

*Primary Examiner* — San Ming R Hui
*Assistant Examiner* — Mikhail O'Donnel Robinson
(74) *Attorney, Agent, or Firm* — Fox Rothschild LLP

(57) ABSTRACT

This patent document discloses novel compounds as inhibitors of the activity of the histone H3K27 demethylase JMJD3. Also disclosed are the use of the compounds and compositions thereof for the treatment of diseases and conditions mediated by JMJD3, in particular cancer, inflammation and autoimmune diseases.

26 Claims, 9 Drawing Sheets

GSK-J1

GSK-J4
(pro-drug of GSK-J1)

UR-8

UR-17

UR-8

4-AMINO PYRIMIDINE COMPOUNDS FOR THE TREATMENT OF CANCER

CROSS REFERENCE TO RELATED APPLICATION

This application claims priority to U.S. Provisional Application No. 63/276,555 filed on Nov. 6, 2021. The content of the application is incorporated herein by reference in its entirety.

TECHNICAL FIELD

The present invention relates to compounds as inhibitors of the activity of the histone H3K27 demethylase JMJD3. The invention also relates to the use of the compounds and compositions thereof to modify the epigenetic status of cells and/or the treatment of diseases and conditions mediated by JMJD3, in particular cancer, inflammation and autoimmune diseases.

BACKGROUND

The Jumonji C (JMJC) domain-containing proteins, including the histone H3 lysine 27 (H3K27) demethylase JMJD3, have been implicated in tumorogenesis and thus have identified histone demethylases as targets of research for anti-cancer therapies. JMJD3 (KDM6B) is one of the approximately 30 JMJC family members found in humans, and functions as a specific demethylase of histone H3K27. JMJD3 can demethylate both the tri- and di-methylated H3K27-repressive histone marks (H3K27me2/me3), thereby facilitating gene transcription. Studies have placed JMJD3 at key cell fate decision checkpoints in T lymphocytes and macrophages. In addition, JMJD3 has been demonstrated to regulate the differentiation state of the epidermis and to activate the tumour suppressor, INK4A-Arf, in response stress induced signals. JMJD3 also appears to be involved in more acute, externally-driven, inflammatory processes. In macrophages, for example, JMJD3 is rapidly induced through an NF-kB-dependent mechanism in response to bacterial products and inflammatory stimuli. Moreover, depletion experiments in these cells have demonstrated that JMJD3 participates directly in the inflammatory transcriptional response, although it remains unclear whether this is achieved through demethylation of H3K27me2/me3 at target gene promoters.

Diffuse intrinsic pontine glioma (DIPG) is the most frequent brainstem tumor in pediatrics and one of the devastating childhood cancers with a median survival of 9 to 12 months from diagnosis. Since these tumors occur in the brainstem, which is a vital area, there are no surgical options for providing relief to patients, and conventional chemotherapy as well as radiation therapy provide palliative relief at best. Children with DIPG will die of their disease despite the more than 250 clinical trials that have been executed to date in attempt to increase survival. Given these dire circumstances, the identification of molecular mechanisms and efficacious therapeutic agents is of high importance for improving treatment outcomes for DIPG patients. In contrast to adult gliomas, DIPG is uniquely dependent on the H3K27M mutation for cancer initiation and maintenance. The H3K27M mutation occurs in H3F3A or HIST1H3B C genes encoding histone H3 variants H3.3 and H3.1, respectively. The H3K27M mutation is detected in as many as 80% of DIPGs and is associated with a significantly shorter survival among all patients with DIPG. The recent discovery of histone H3K27M mutations in pediatric gliomas and the identification of the altered epigenetic program resulting from these mutations has prompted the investigation of small-molecule inhibitors targeting JMJD3 H3K27 demethylases as new cancer therapies.

SUMMARY

This patent document discloses compounds as inhibitors of the activity of the histone H3K27 demethylase JMJD3 for the treatment of diseases and conditions including cancer, inflammation and autoimmune diseases. An aspect of the invention provides a compound of Formula I or a pharmaceutically acceptable salt, or isomer thereof, Formula I

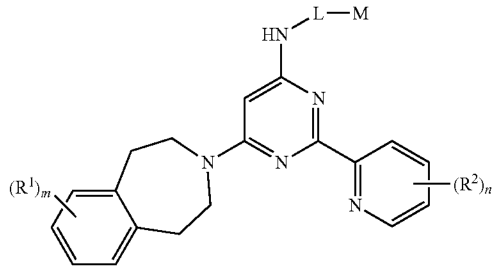

wherein:

L is a linker selected from the group consisting of $C_{1-6}$alkylene, $C_{2-6}$alkenylene, and $C_{2-6}$alkynlene, each of which is optionally substituted with one or more substituents selected from $C_{1-6}$alkyl, halo$C_{1-6}$alkyl, halogen, wherein two or more $C_{1-6}$alkyl substituents optionally link up to form a 3-6 membered ring;

M is selected from the group consisting of $OR^a$, $C(O)R^b$, 3-6 membered cycloalkylnone, 4-6 membered lactam, and 4-6 membered lactone;

$R^a$ is selected from the group consisting of H, $C_{1-6}$alkyl, halo$C_{1-6}$alkyl, $C(O)C_{1-6}$alkyl, $C(O)C_{1-4}$alkylene-$(OC_{2-4}$alkylene$)_p$-$OC_{1-4}$alkyl;

$R^b$ is selected from the group consisting of halo$C_{1-4}$alkyl, $C_{1-4}$alkylene-OH, $NR^cR^d$;

$R^c$ is H or $C_{1-4}$alkyl;

$R^d$ is OH, $OC_{1-6}$alkyl, $OC_{1-4}$alkylene$C_{6-10}$aryl, $OC_{1-4}$alkylene$C_{5-10}$heteroaryl, $C_{6-10}$aryl, or $C_{5-10}$heteroaryl, wherein the $C_{6-10}$aryl or $C_5$-10heteroaryl is optionally substituted with one or more substituents selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$;

Each $R^e$ is independently H or $C_{1-4}$alkyl;

Each $R^1$ is independently selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$;

Each $R^2$ is independently selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$;

m and n are each an integer ranging from 0 to 4; and p is an integer ranging from 1 to 20.

Another aspect of this patent document discloses a pharmaceutical composition comprising the compound described herein or the pharmaceutically acceptable salt, isomer, or prodrug thereof.

Another aspect of this disclosure provides a method of treating a disease in a subject comprising administering to the subject in need a therapeutically effective amount of a compound of Formula I, a pharmaceutically acceptable salt or isomer thereof, or a pharmaceutical composition thereof. The diseases to be treated with the method of the present invention include cancer, inflammation and autoimmune diseases.

DESCRIPTIONS OF THE DRAWINGS

FIG. 1 shows the structures of GSK-J1, GSK-J4 and UR-8.

FIG. 2. shows dose-dependent inhibition of DIPG cell growth, with $IC_{50}$ at 4-6 μM in three H3K27M mutant DIPG cell lines (H3.3 K27M SF8628, H3.3 K27M DIPG-007, and H3.1 K27M SU-DIPGIV) which were treated with GSK-J4 (R&D System), UR-8, and UR-17 for 72 hours.

FIG. 3 shows UR-compounds in vivo anti-tumor activity in patient-derived K27M DIPG xenografted mice. Mice with SF8628 intracranial (brainstem) tumor were randomized to four treatment groups: vehicle control (DMSO, n=7), GSK-J4 (100 mg/kg/day for 10 consecutive days, n=8), UR-8 (100 mg/kg/day for 10 consecutive days, n=8), and UR-17 (100 mg/kg/day for 10 consecutive days, n=8). FIG. 3 (A) Upper: Growth plots for intracranial tumors using tumor bioluminescence values. Lower: Corresponding tumor bioluminescence intensity overlay images for representative vehicle-treated, GSK-J4, UR-17, and UR-8-treated mice. FIG. 3 (B) Corresponding survival plots for each experiment. Statistical analysis was performed using a log-rank test: control vs. GSK-J4, P=0.0094; control vs. UR-8, *P=0.0002; control vs. UR-17, *P=0.0008; GSK-J4 vs. UR-8, *P=0.0008; UR-8 vs. UR-17, *P=0.0197. FIG. 3 (*c*) Effects of UR-8 on cell proliferation.

DETAILED DESCRIPTION

Figure 1:
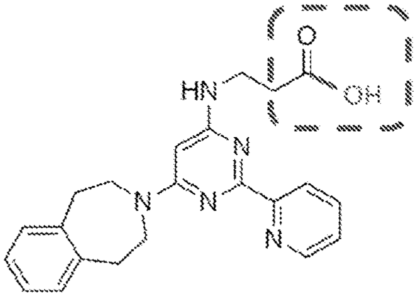
Figure 1:
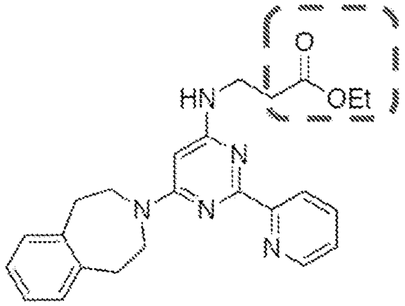
Figure 1:
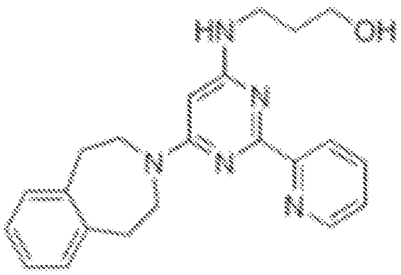
Figure 1:
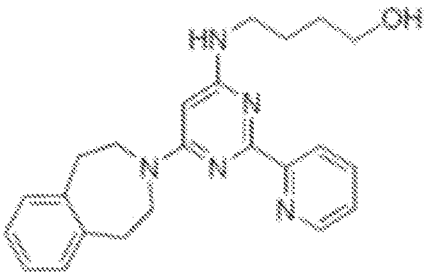

Studies have identified JMJC domain-containing proteins as histone demethylases that mediate the reversal of methylation at histone H3K4, H3K9 and H3K36. The JMJD3 family of proteins is a subfamily of JMJC domain-containing proteins that have been shown to demethyate H3K27. Inhibitors of JMJD3 histone H3K27 demethylase are therefore useful in changing the epigenetic status of cells resulting in inhibiting or activating chromatin remodelling by modifying histone methylation and thus in treating disorders associated with such modified histone methylation including cancer and other conditions associated with undesirable cell proliferation, autoimmune and inflammatory diseases or conditions and psychiatric disorders including depression.

While the following text may reference or exemplify specific embodiments of a compound or a method of treating a disease or condition, it is not intended to limit the scope of the compound or method to such particular reference or examples. Various modifications may be made by those skilled in the art, in view of practical and economic considerations, such as the substitutions of the compound and the amount or administration of the compound for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "subject" encompasses any animal, but preferably a mammal, e.g., human, non-human primate, a dog, a cat, a horse, a cow, or a rodent. More preferably, the subject is a human.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" or "pharmaceutically acceptable" refers to a carrier or diluent that does not abrogate the biological activity and properties of the compound.

The term "therapeutically effective amount" refers to an amount of a compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The term "alkyl" refers to monovalent saturated alkane radical groups particularly having up to about 18 carbon atoms, more particularly as a lower alkyl, from 1 to 8 carbon atoms and still more particularly, from 1 to 6 carbon atoms. The hydrocarbon chain may be either straight-chained or branched. The term "$C_{1-10}$ alkyl" or "$C_1$-$C_{10}$ alkyl" refers to alkyl groups having 1, 2, 3, 4, 5, 6, 7, 8, 9 or 10 carbon atoms. Similarly, the term "$C_{1-4}$alkyl" refers to alkyl groups having 1, 2, 3, or 4 carbon atoms. Non-limiting examples of alkyls include groups such as methyl, ethyl, n-propyl, iso-propyl, n-butyl, iso-butyl, tert-butyl, n-hexyl, n-octyl, tert-octyl and the like.

The term "alkylene" refers to a divalent hydrocarbon which may be either straight-chained or branched. Different from alkyl which has only one point of bonding with other groups or atoms, alkylene has two points of bonding. Non-limiting examples include groups such as $CH_2$, $(CH_2)_2$, $CH_2CH(CH_3)$, and the like. A $C_{1-6}$ alkylene has 1, 2, 3, 4, 5 or 6 carbons. A $C_{1-4}$ alkylene has 1, 2, 3 or 4 carbons.

The term "$C_{1-4}$ alkoxy" includes an alkyoxy group having 1, 2, 3 or 4 carbons.

The term "carbocycle" or "cycloalkyl" refers to 3 to 10 membered cyclic hydrocarbyl groups having only carbon atoms as ring atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

The term "haloalkyl" refers to a $C_{6-10}$alkyl chain, straight or branched, in which one or more hydrogen has been replaced by a halogen. Non-limiting examples of haloalkyls include $CHF_2$, $CFH_2$, $CF_3$, $CH_2CF_2$, $CH_2CF_3$, and $CH_2CH_2F$. In some embodiments, the alkyl in haloalkyl has 1, 2, 3 or 4 carbons.

The term "heterocycle" or "heterocycloalkyl" refers to 3 to 10 membered substituted or nonsubstituted non-armoatic cyclic groups where one or more carbon ring atoms are replaced with hetero atoms or groups containing heteroatoms (e.g. NH, NC1-C4alkyl O, and S). Nonlimiting examples include pyrrolidine, piperidine, N-methyl-piperizine, and morpholine. Optional substituents include $C_{1-6}$ alkyl, $C_{1-4}$ alkoxy, halogen, haloalkyl, sulfonamido, and amido.

The term "aryl" is intended to mean any stable monocyclic or bicyclic carbon ring of up to 7 members in each ring, wherein at least one ring is aromatic and all ring atoms of the aromatic ring are carbon atoms. Typical aryl groups include, but are not limited to, groups derived from aceanthrylene, acephenanthrylene, anthracene, azulene, benzene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, and the like. Particularly, an aryl group comprises from 6 to 10 or 6 to 14 carbon atoms.

The term "hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloheteroalkyl.

The term "halogen" refers to F, Cl, Br, or I.

The term "carboxamide" refers to a group of —CONRR, wherein each R is independently a hydrogen, $C_{1-6}$ alkyl, 3-7 membered carbocycle, 3-7 membered heterocycle, 5-10 membered heteroaryl or 6-10 membered aryl. The two R groups may link up to form a 3-7 membered carbocycle, 3-7 membered heterocycle, 5-10 membered heteroaryl or 6-10 membered aryl.

The term "amido" refers to a group of —NRCOR', where R is hydrogen or $C_{1-4}$ alkyl and R' is $C_{1-6}$ alkyl, 3-7 membered carbocycle, 3-7 membered heterocycle, 5-10 membered heteroaryl or 6-10 membered aryl.

The term "oxo" refers to =O as a substituent. None-limiting examples of include pyrrolidinone (oxo on pyrrolidine) and cyclopentanone.

The term "heteroaryl" refers to groups having 5 to 14 ring atoms, preferably 5, 6, 9, or 10 ring atoms, having 6, 10, or 14 π electrons shared in a cyclic array, wherein at least one ring atom contributing to the shared π electrons in the cyclic array is a heteroatom. Typical heteroaryl groups include, but are not limited to, groups derived from acridine, carbazole, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, phenanthridine, phenanthroline, phenazine, phthalazine, phthalimide, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

The term "pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

An aspect of this patent document provides a compound or a pharmaceutically acceptable salt thereof, wherein the compound is represented by Formula I, Formula I

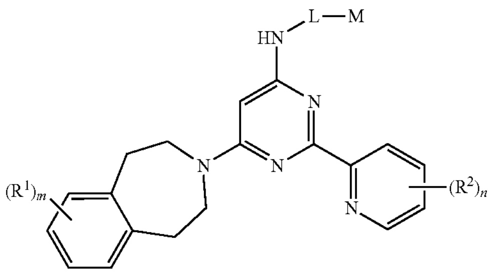

wherein:

L is a linker selected from the group consisting of $C_{1-6}$alkylene, $C_{2-6}$alkenylene, and $C_{2-6}$alkynlene, each of which is optionally substituted with one or more substituents selected from $C_{1-6}$alkyl, halo$C_{1-6}$alkyl, halogen, wherein two or more $C_{1-6}$alkyl substituents optionally link up to form a 3-6 membered ring;

M is selected from the group consisting of $OR^a$, $C(O)R^b$, 3-6 membered cycloalkylnone, 4-6 membered lactam, and 4-6 membered lactone;

$R^a$ is selected from the group consisting of H, $C_{1-6}$alkyl, halo$C_{1-6}$alkyl, $C(O)C_{1-6}$alkyl, $C(O)C_{1-4}$alkylene-($OC_{2-4}$ alkylene)$_p$-$OC_{1-4}$alkyl;

$R^b$ is selected from the group consisting of halo$C_{1-4}$alkyl, $C_{1-4}$alkylene-OH, $NR^cR^d$;

$R^c$ is H or $C_{1-4}$alkyl;

$R^d$ is OH, $OC_{1-6}$alkyl, $OC_{1-4}$alkylene$C_{6-10}$aryl, $OC_{1-4}$alkylene$C_{5-10}$heteroaryl, $C_{6-10}$aryl, or $C_{5-10}$heteroaryl, wherein the $C_{6-10}$aryl or $C_{5-10}$ heteroaryl is optionally substituted with one or more substituents selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

each $R^e$ is independently H or $C_{1-4}$alkyl;

Each $R^1$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

Each $R^2$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

m and n are each an integer ranging from 0 to 4 (i.e. 0, 1, 2, 3 or 4); and p is an integer ranging from 1 to 20 (i.e. 1, 2, 3, 4, 5, 6, 7, 8, 9, 10, 11 . . . 20).

In each of the embodiments disclosed herein, when one or more chiral centers are present, each chiral center is independently R or S in configuration.

In some embodiments, M is $OR^a$, $R^a$ is H or $C_{1-6}$alkyl, L is optionally substituted $C_{2-6}$alkylene. In some embodiments, M is $OR^a$, $R^a$ is H or $C_{1-6}$alkyl, L is $C_{2-4}$alkylene. In some embodiments, M is OH, L is $C_{2-4}$alkylene (e.g. $C_2$, $C_3$, or $C_4$ alkylene). In some embodiments, m and n are both 0. In some embodiments, M is OH, L is $C_{2-3}$alkylene (e.g. $C_2$, or $C_3$ alkylene), m and n are both 0.

In some embodiments, M is $OR^a$, $R^a$ is H or $C_{1-6}$alkyl, L is $C_{2-6}$alkylene substituted with halo$C_{1-6}$alkyl. In some embodiments, M is OH, L is $C_{2-4}$alkylene substituted with $CF_3$, and $CF_3$ and OH are preferably on carbons adjacent to each other. In some embodiments, m and n are both 0. In some embodiments, m and n are both 0, M is OH, L is $C_{2-3}$alkylene substituted with $CF_3$, and $CF_3$ and OH are preferably on carbons adjacent to each other.

In some embodiments, M is $OR^a$, $R^a$ is H or $C_{1-6}$alkyl, L is $C_{3-6}$alkylene wherein two substituents of the $C_{3-6}$alkylene link up to form a 3-5 membered carbocyclic or heterocyclic ring. In some embodiments, M is OH, L is $C_{2-4}$alkylene wherein two substituents of the $C_{3-6}$alkylene link up to form a 3-membered carbocyclic or heterocyclic ring. In some embodiments, M is OH, L is $C_4$alkylene wherein two substituents of the $C_{3-6}$alkylene link up to form a 3- or 4-membered carbocyclic ring, wherein the carbocyclic ring may be in a Z or E configuration with regards to groups attached thereto.

In some embodiments, M is $OR^a$, $R^a$ is $C(O)C_{1-6}$alkyl, L is optionally substituted $C_{2-6}$alkylene, and preferably the $C_{1-6}$alkyl is a secondary or tertially alkyl. In some embodiments, M is $OR^a$, $R^a$ is $C(O)_{tert}$butyl, L is $C_{2-6}$alkylene.

In some embodiments, L is $C_{2-6}$alkylene, wherein M is $OR^a$, and $R^a$ is $C(O)C_{1-4}$alkylene-($OC_{2-4}$alkylene)$_p$-$OC_{1-4}$ alkyl, p is 1, 2, 3 or 4. In some embodiments, m and n are both 0. In some embodiments, L is $C_{2-6}$alkylene, wherein M is $OR^a$, and $R^a$ is $C(O)C_2$alkylene-($OC_{2-3}$alkylene)$_p$-$OC_{1-3}$ alkyl, p is 2, 3 or 4, and m and n are both 0.

In some embodiments, L is $C_{2-6}$alkylene, M is $C(O)R^b$, and $R^b$ is selected from the group consisting of halo$C_{1-4}$ alkyl, $C_{1-4}$alkylene-OH, and $NR^cR^d$. In some embodiments, $R^c$ is H or $C_{1-4}$alkyl, and $R^d$ is OH or $OC_{1-2}$alkylene$C_6$aryl. In some embodiments, L is $C_{2-3}$alkylene, M is $C(O)R^b$, and $R^b$ is $NR^cR^d$, $R^c$ is H or $C_{1-4}$alkyl, and $R^d$ is OH or $OC_{1-2}$alkylene$C_6$aryl, and $C_6$aryl is optionally substituted phenyl.

In some embodiments, L is $C_{2-6}$alkylene, and M is 3-6 membered cycloalkylnone, 4-6 membered lactam, or 4-6 membered lactone. Any atom, of the ring, if chemically feasible, can be substituted with a substituent such as OH, $C_{1-6}$alkyl, phenyl, or 5-10 membered heteroaryl. Nonlimiting examples of M are as follows.

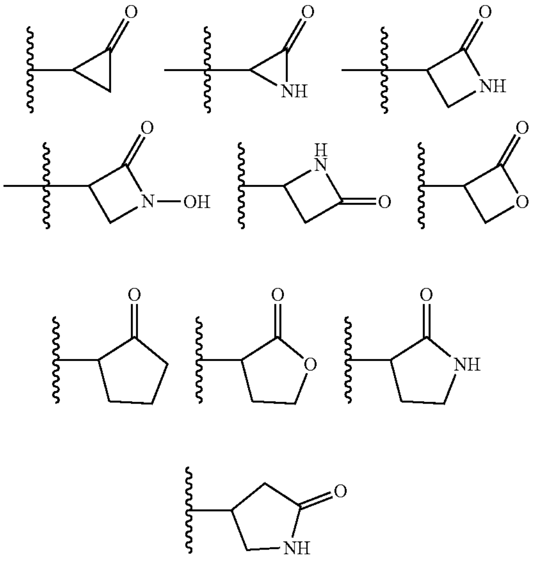

Nonlimiting examples of the compounds of Formula include the following:

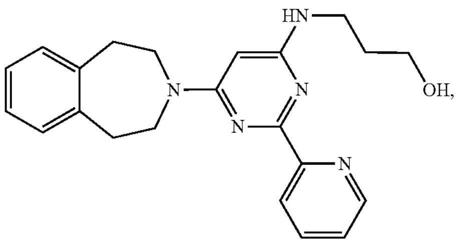
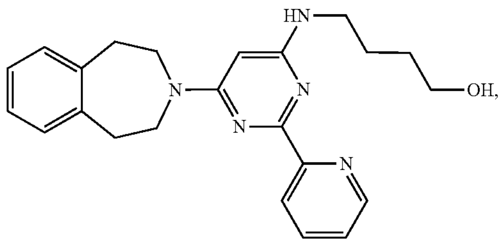
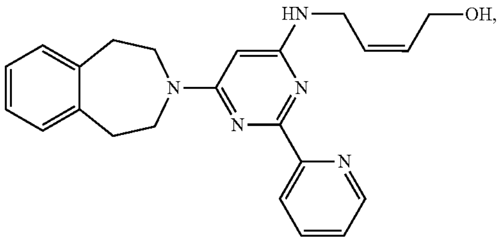
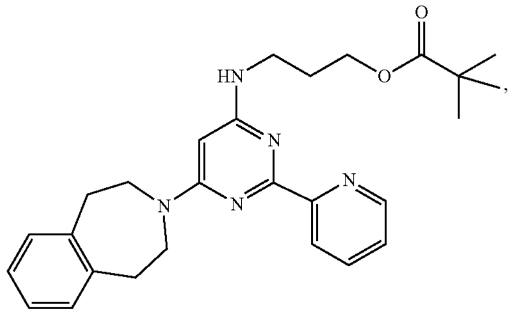
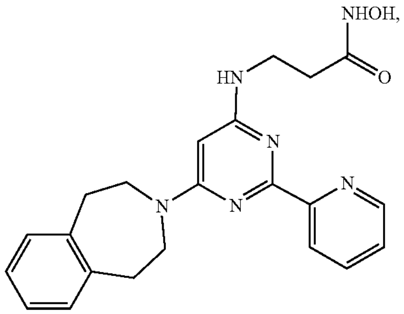
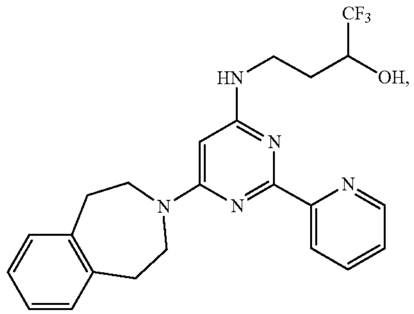
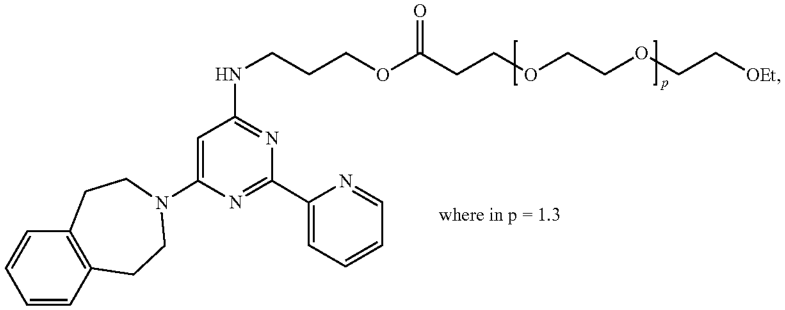
where in p = 1.3
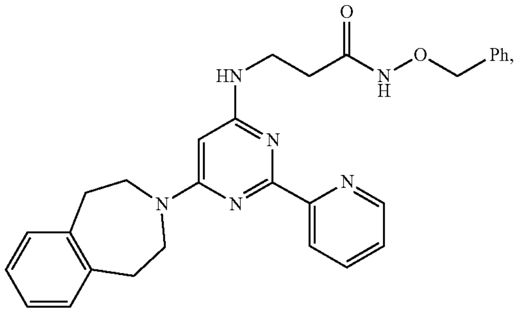
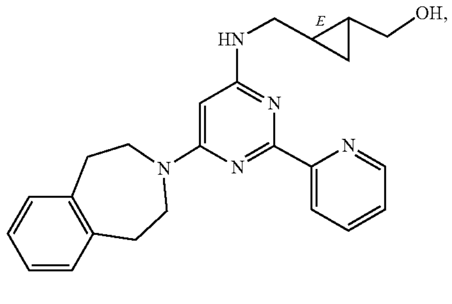

-continued
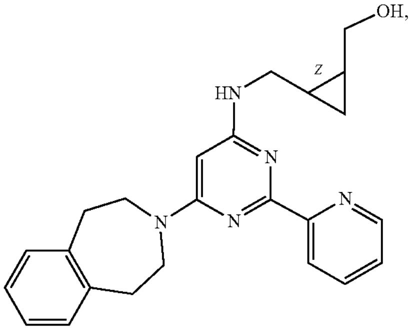
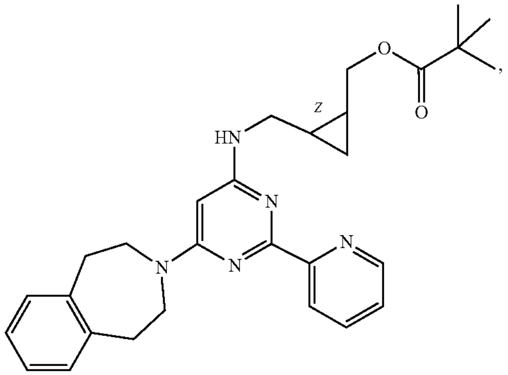
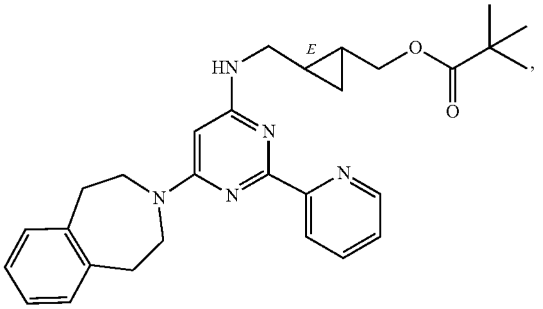
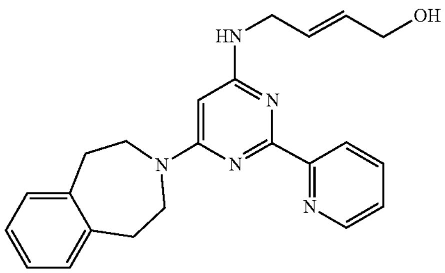
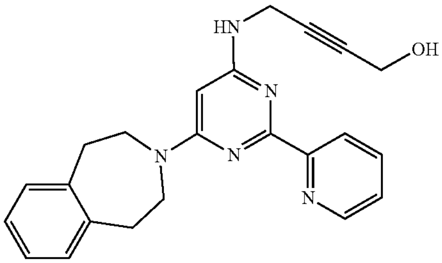
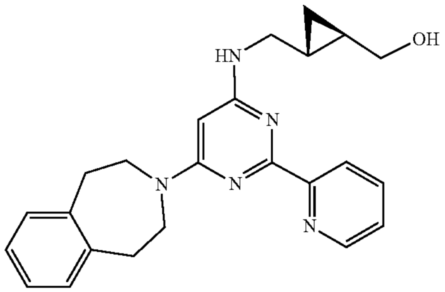
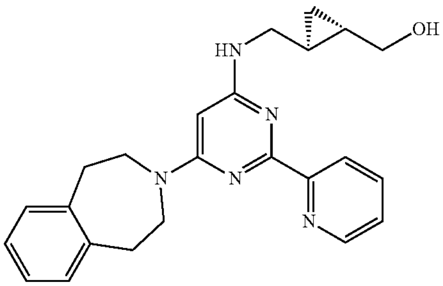
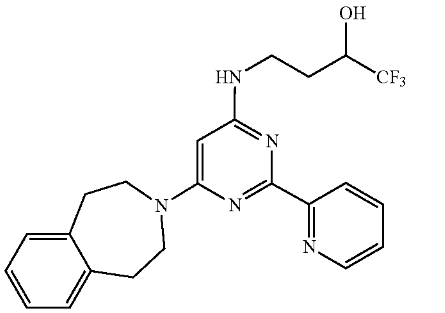
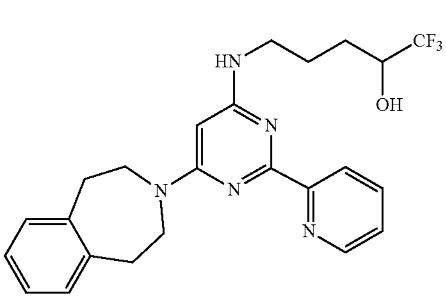
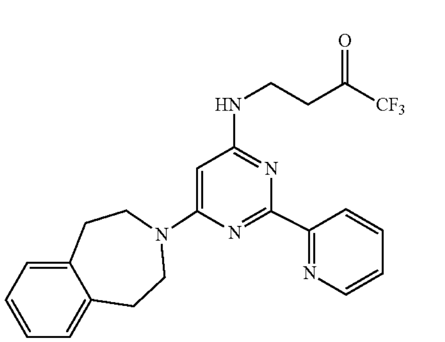

-continued
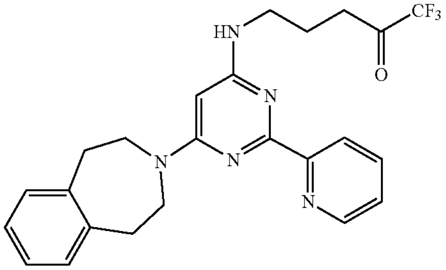
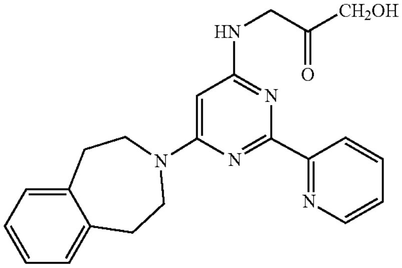
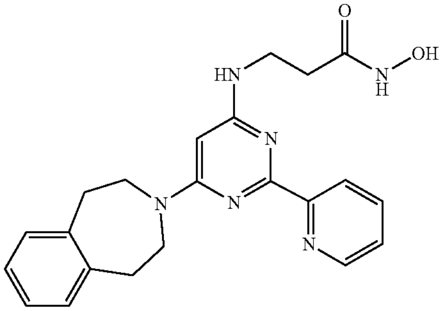
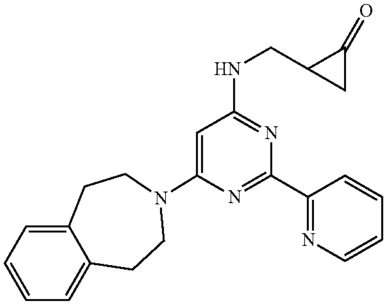
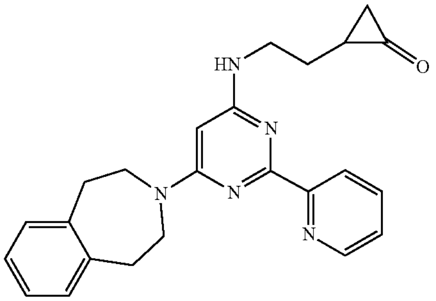
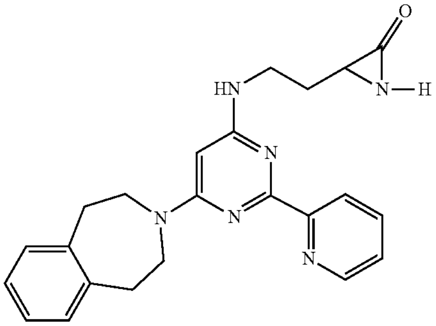
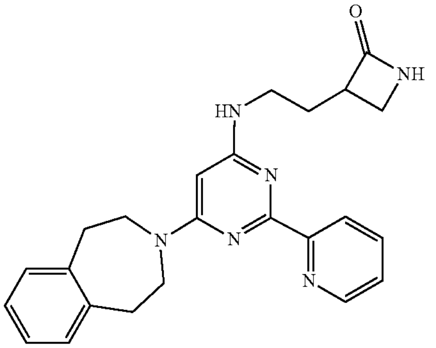
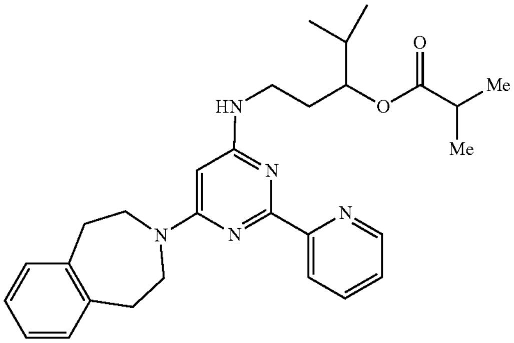
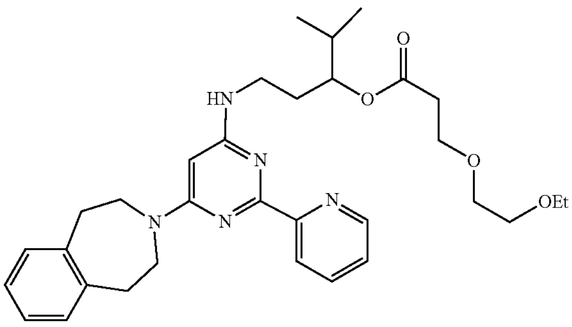
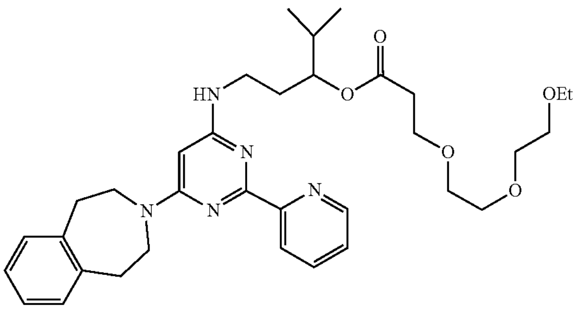

-continued
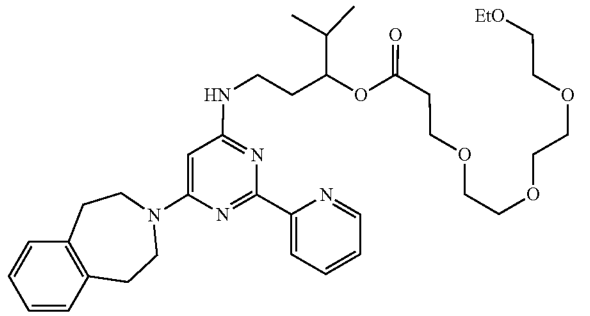
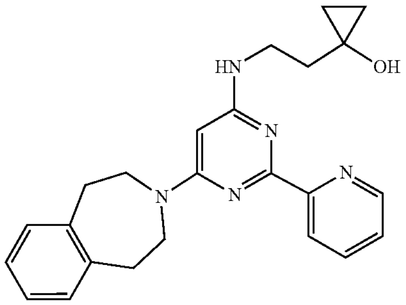
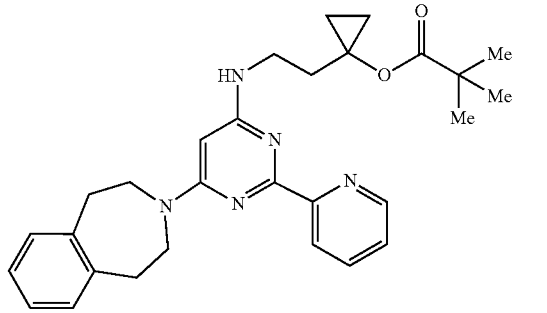
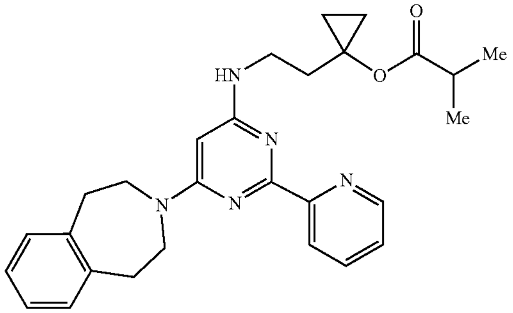
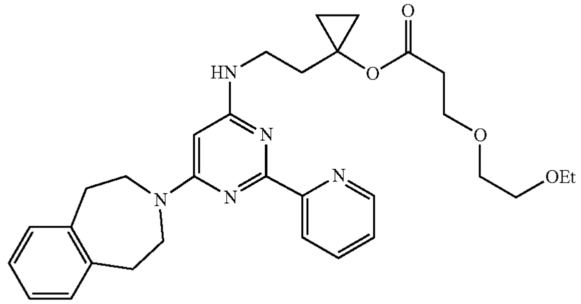
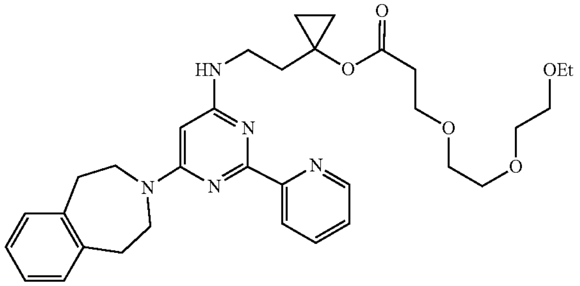
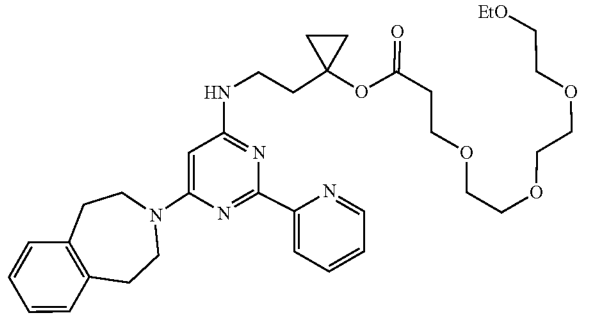
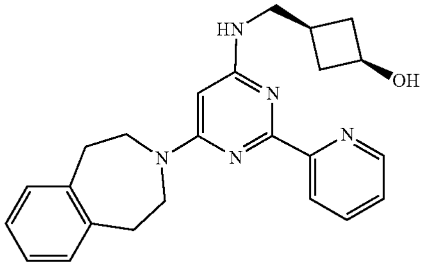
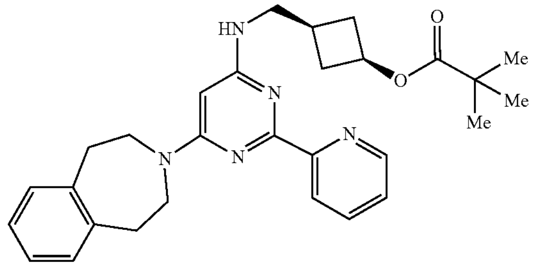
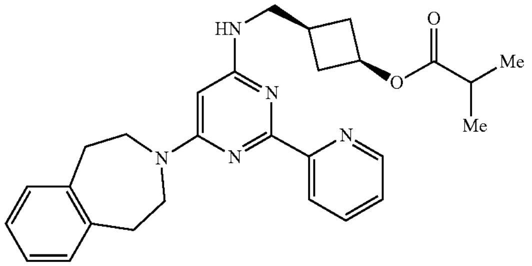

-continued
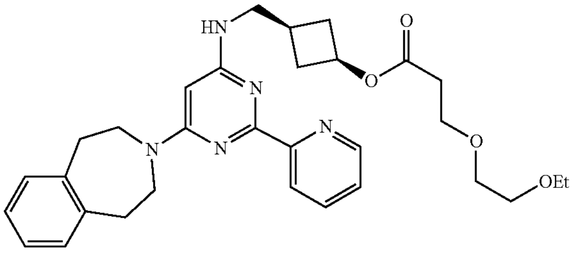
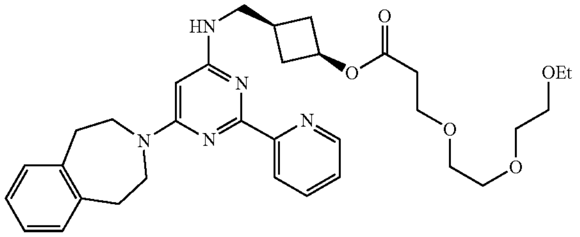
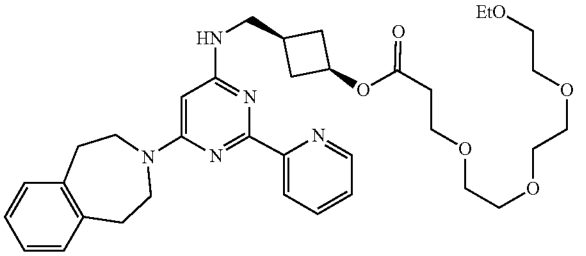
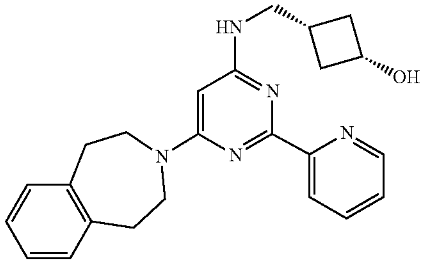
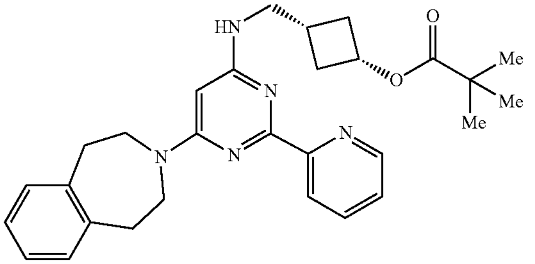
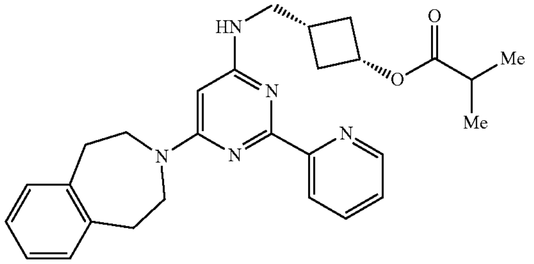
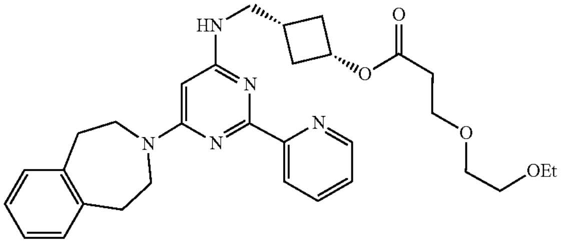
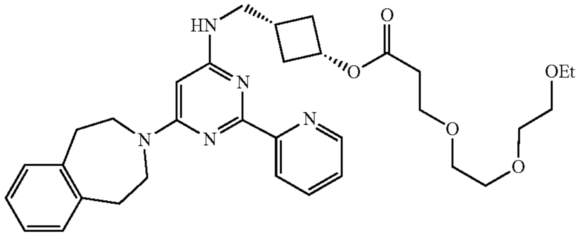
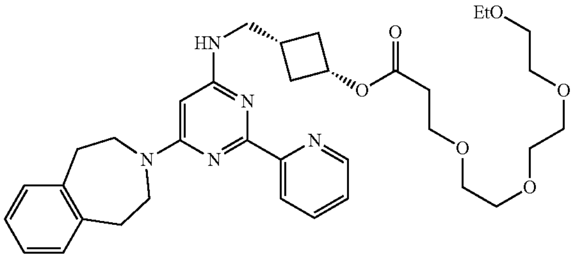
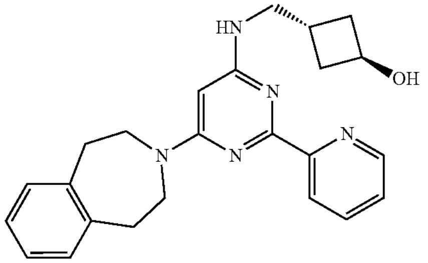
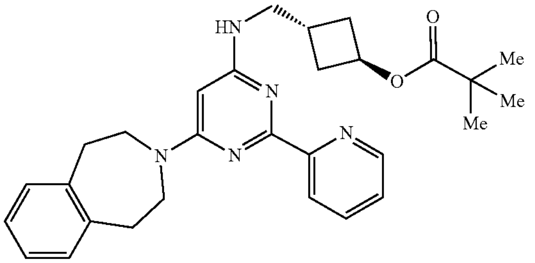
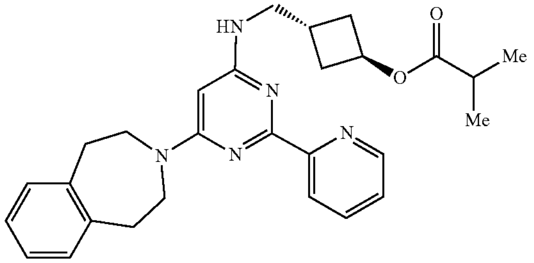

-continued
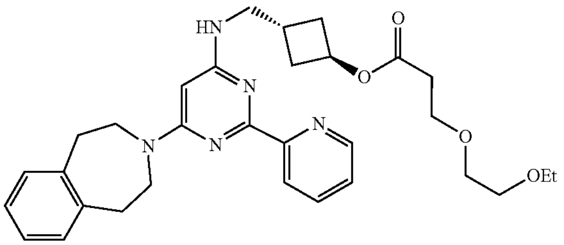
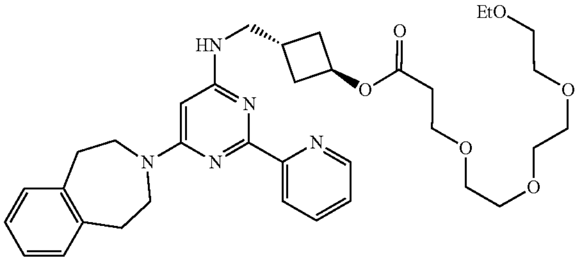
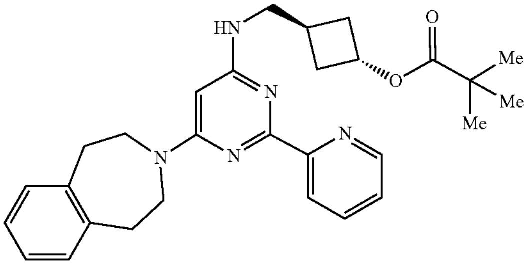
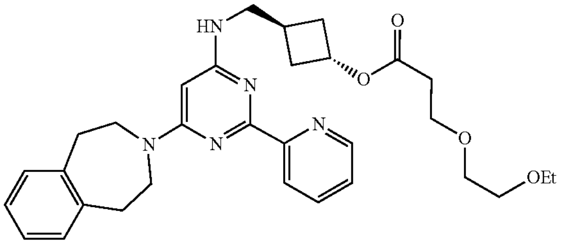
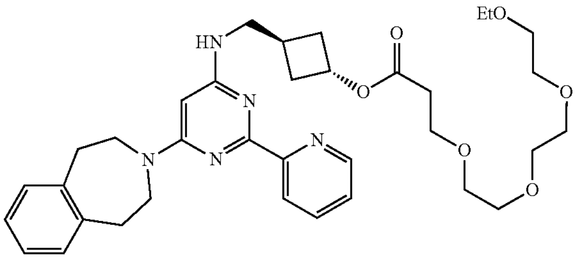
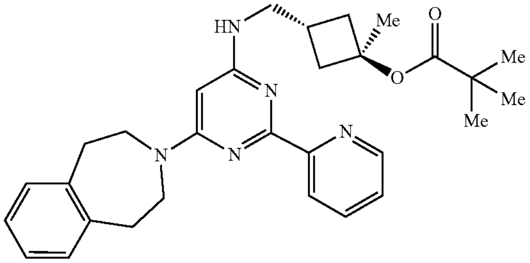
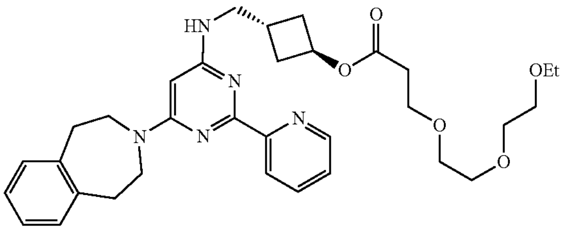
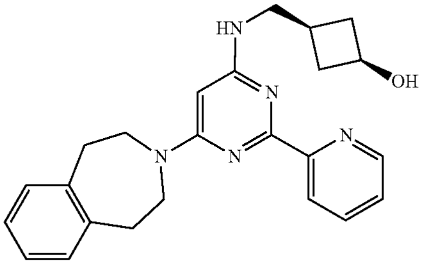
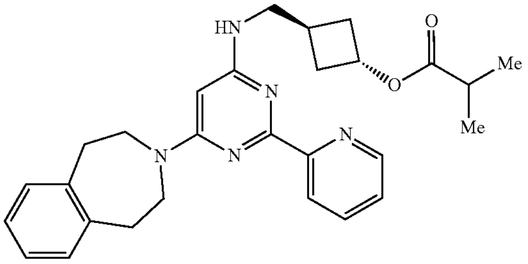
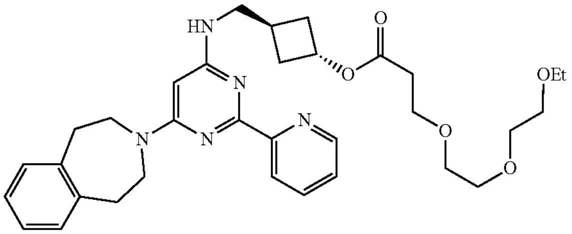
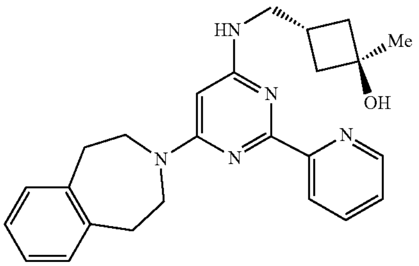
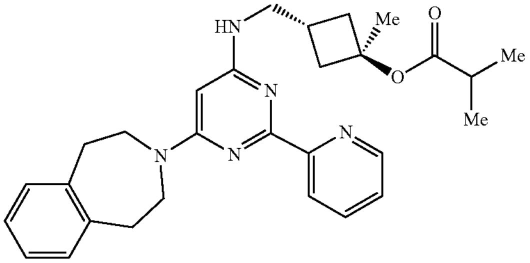

-continued
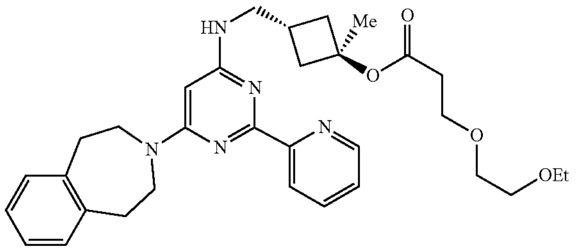
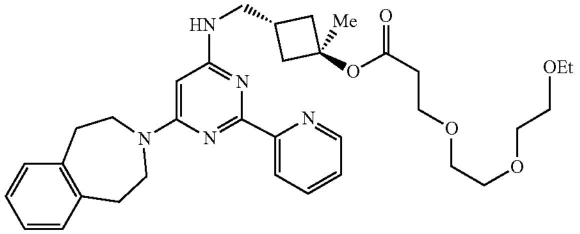
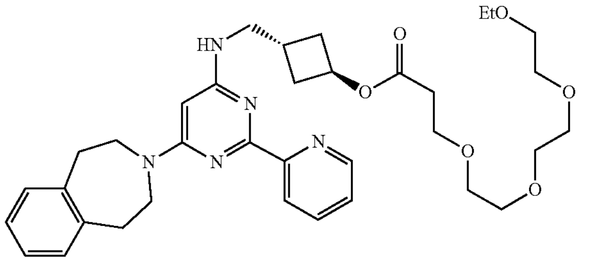
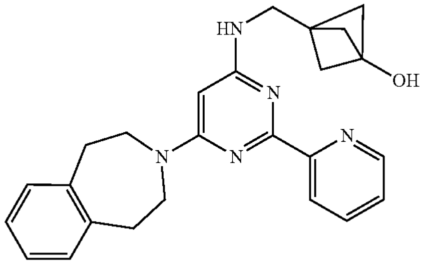
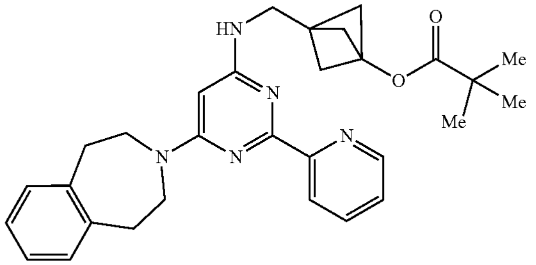
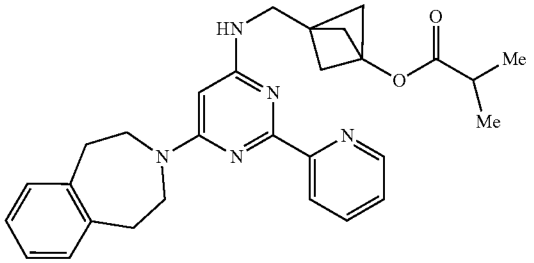
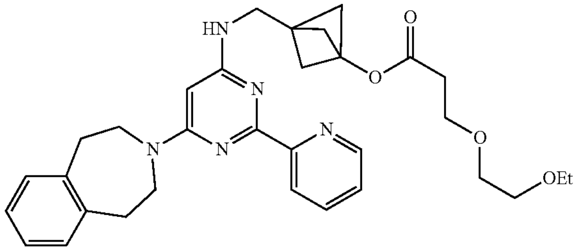
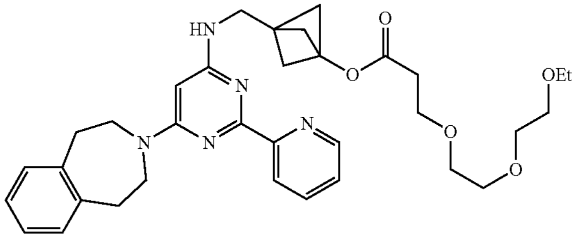
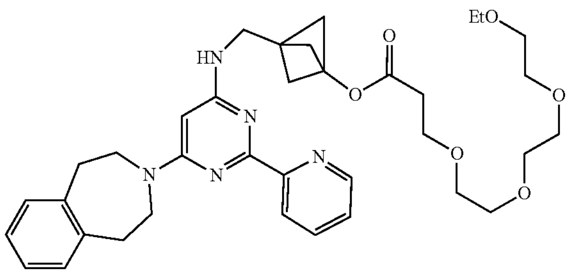
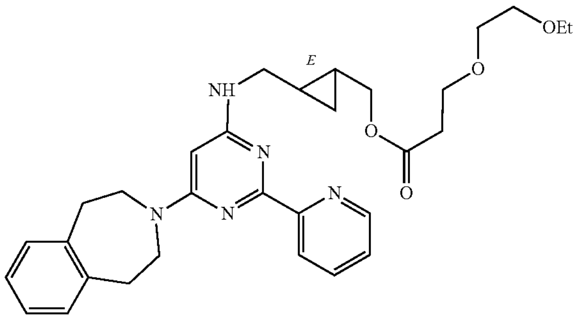
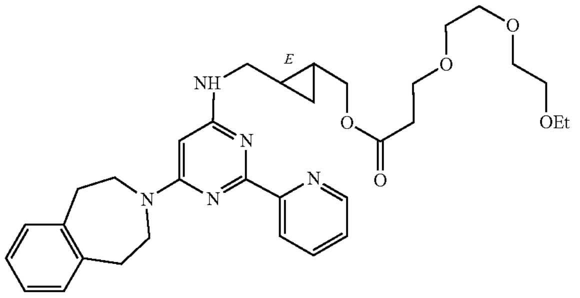
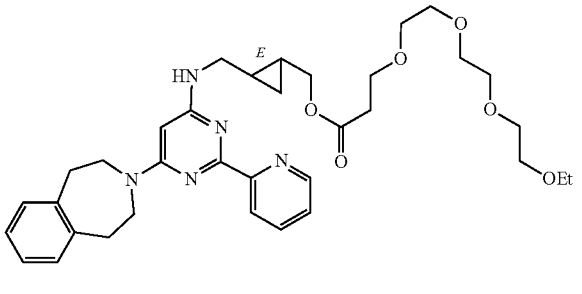

-continued

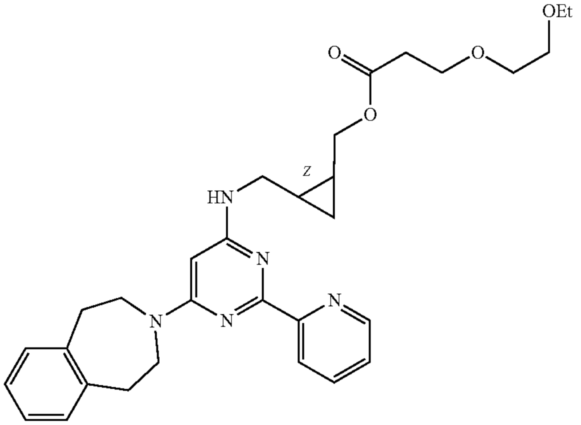

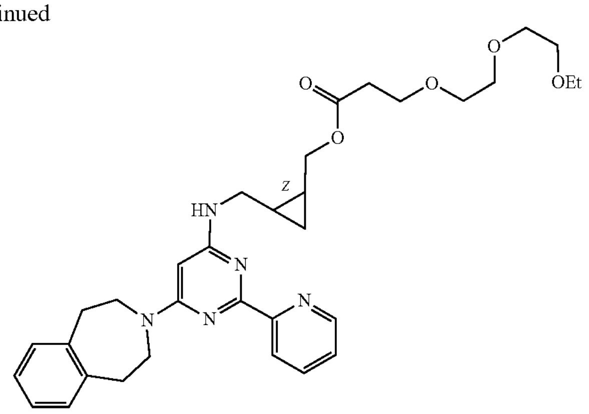

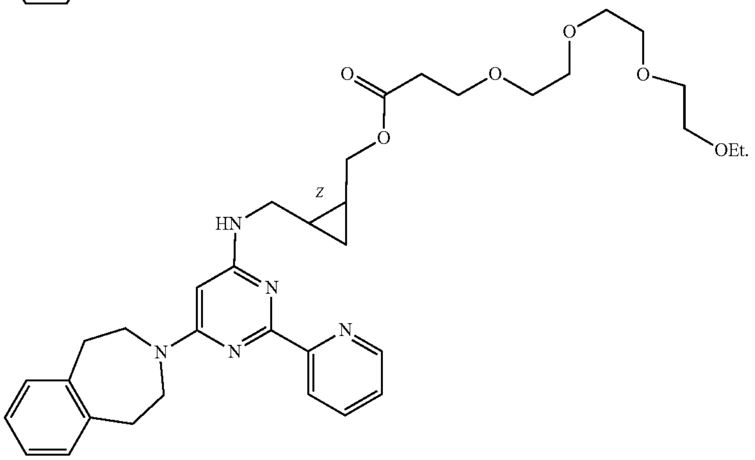

Another aspect of the present disclosure provides a pharmaceutical composition containing a therapeutically effective amount of the above-described compound and a pharmaceutically acceptable carrier.

The pharmaceutical composition may also contain one or more physiologically acceptable surface-active agents, additional carriers, diluents, excipients, smoothing agents, suspension agents, film forming substances, and coating assistants, or a combination thereof, and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid, and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compounds described herein can be administered to a human patient per se, or in pharmaceutical compositions where they are mixed with other active ingredient(s), as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of the compound to treat a disease as part of a particular administration protocol, as would be understood by those of skill in the art. Techniques for formulation and administration of the compounds of the instant application may be found in "Remington's Pharmaceutical Sciences," Mack Publishing Co., Easton, PA, 18th edition, 1990.

The pharmaceutical compositions may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Another aspect of this disclosure provides a method of treating cancer, autoimmune and inflammatory diseases, or conditions in a subject. The method includes administering to the subject in need a therapeutically effective amount of a compound of Formula I or a pharmaceutically acceptable salt, isomer, or pharmaceutical composition thereof. Specific embodiments of the compound of Formula I are as described above. Without being limited to any particular theory, it is postulated that the therapeutic efficacy of the compound of Formula I results from pharmacologic restoration of global H3K27 methylation via inhibition of JMJD3 demethylase activity for that residue.

Examples of cancer diseases and conditions in which compounds of formula (I), or a pharmaceutically acceptable salt thereof may have potentially beneficial antitumour effects include, but are not limited to, cancers of the lung, bone, pancreas, skin, head, neck, uterus, ovaries, stomach, colon, breast, esophagus, small intestine, bowel, endocrine system, thyroid glad, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers. The compounds of the compound of formula (I) or a pharmaceutically acceptable salt thereof may also be useful in the treatment of one or more diseases afflicting mammals which are characterized by cellular proliferation in the area of disorders associated with neovascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases. In some embodiments, the cancer is T-cell acute lymphoblastic leukemia, acute myeloid leukemia, diffuse large B-cell lymphoma, neuroblastoma, prostate cancer, gastric cancer, or diffuse pontine intrinsic glioblastoma (DIPG).

The compound of compound of formula (I) or a pharmaceutically acceptable salt thereof may be employed with other therapeutic methods of cancer treatment. In particular, in antineoplastic therapy, combination therapy with other chemotherapeutic, hormonal, antibody agents as well as surgical and/or radiation treatments other than those mentioned above are envisaged. As indicated, therapeutically effective amounts of the compound of compound of formula (I) or a pharmaceutically acceptable salt thereof are discussed above. The therapeutically effective amount of the further therapeutic agents of the present invention will depend upon several factors including, for example, the age and weight of the mammal, the precise condition requiring treatment, the severity of the condition, the nature of the formulation, and the route of administration. Ultimately, the therapeutically effective amount will be at the discretion of the attendant physician or veterinarian. The relative timings of administration will be selected to achieve the desired combined therapeutic effect. In one embodiment, the further anti-cancer therapy is surgical and/or radiotherapy.

In some embodiments, the methods disclosed herein further including administering to the subject one, two, three or more of the anticancer agents or therapies including chemotherapy, biologics, immunotherapy, HER2 targeted therapy, or curative-intent radiotherapy for the treatment of the cancer. Examples of anticancer agents or therapies for use in combination with the compound of Formula I or its pharmaceutically acceptable salt thereof are shown below.

Non-limiting examples of HER2-targeted agents include trastuzumab, pertuzumab, lapatinib, neratinib, SYD985 and trastuzumab emtansine (T-DM1), and antibody-drug conjugate thereof (e.g. Trastuzumab duocarmazine).

Non-limiting examples of checkpoint inhibitors include those that target PD-1, PD-L1, CTLA4 and TIGIT (T cell immunoglobulin and ITIM domain). Further examples include Ipilimumab (Yervoy®; blocking a checkpoint protein called CTLA-4); pembrolizumab (Keytruda®), Cemiplimab (Libtayo) and nivolumab (Opdivo®) (targeting another checkpoint protein called PD-1); atezolizumab (Tecentriq®), Avelumab (Bavencio), and Durvalumab (Imfinzi) (targeting PD-L1); MK-7684, Etigilimab/OMP-313 M32, Tiragolumab/MTIG7192A/RG-6058, BMS-986207, AB-154 and ASP-8374 (targeting TIGIT), and V-domain Ig suppressor of T cell activation (VISTA).

Non-limiting examples of tyrosine kinase inhibitors as chemotherapy include erlotinib, gefitinib, afatinib, dacomitinib and osimertinib.

Further non-limiting examples of the chemotherapy include alkylating agents: Busulfan, dacarbazine, ifosfamide, hexamethylmelamine, thiotepa, dacarbazine, lomustine, chlorambucil, procarbazine, altretamine, estramustine phosphate, mechlorethamine, streptozocin, temozolomide, Semustine cyclophosphamide;

platinum agents: spiroplatin, tetraplatin, ormaplatin, iproplatin, ZD-0473 (AnorMED), oxaliplatin carboplatin, lobaplatin (Aeterna), satraplatin (Johnson Matthey), BBR-3464 (Hoffmann-La Roche), SM-11355 (Sumitomo), AP-5280 (Access), cisplatin, arboplatin, cisplatin, satraplatin, oxaliplatin, nedaplatin, triplatin tetranitrate, temozolomide, procarbazin;

antimetabolites: azacytidine, Floxuridine, 2-chlorodeoxyadenosine, 6-mercaptopurine, 6-thioguanine, cytarabine, 2-fluorodeoxy cytidine, methotrexate, tomudex, fludarabine, raltitrexed, trimetrexate, deoxycoformycin, pentostatin, hydroxyurea, decitabine (SuperGen), clofarabine (Bioenvision), irofulven (MGI Pharma), DMDC (Hoffmann-La Roche), ethynylcytidine (Taiho), gemcitabine, capecitabine;

topoisomerase inhibitors: amsacrine, epirubicin, etoposide, teniposide or mitoxantrone, 7-ethyl-10-hydroxy-camptothecin, dexrazoxanet (TopoTarget), pixantrone (Novuspharma), rebeccamycin analogue (Exelixis), BBR-3576 (Novuspharma), rubitecan (SuperGen), irinotecan (CPT-11), topotecan; antitumor antibiotics: valrubicin, therarubicin, idarubicin, rubidazone, plicamycin, porfiromycin mitoxantrone (novantrone), amonafide, azonafide, anthrapyrazole, oxantrazole, losoxantrone, MEN-10755 (Menarini), GPX-100 (Gem Pharmaceuticals), Epirubicin, mitoxantrone, doxorubicin;

antimitotic agents: colchicine, vinblastine, vindesine, dolastatin 10 (NCI), rhizoxin (Fujisawa), mivobulin (Warner-Lambert), cemadotin (BASF), RPR 109881A (Aventis), TXD 258 (Aventis), epothilone B (Novartis), T 900607 (Tularik), T 138067 (Tularik), cryptophycin 52 (Eli Lilly), vinflunine (Fabre), auristatin PE (Teikoku Hormone), BMS 247550 (BMS), BMS 184476 (BMS), BMS 188797 (BMS), taxoprexin (Protarga), SB 408075 (GlaxoSmithKline), Vinorelbine, Trichostatin A, E7010 (Abbott), PG-TXL (Cell Therapeutics), IDN 5109 (Bayer), A 105972 (Abbott), A 204197 (Abbott), LU 223651 (BASF), D 24851 (ASTA-Medica), ER-86526 (Eisai), combretastatin A4 (BMS), isohomohalichondrin-B (PharmaMar), ZD 6126 (AstraZeneca), AZ10992 (Asahi), IDN-5109 (Indena), AVLB (Prescient NeuroPharma), azaepothilone B (BMS), BNP-7787 (BioNumerik), CA-4 prodrug (OXiGENE), dolastatin-10 (NIH), CA-4 (OXiGENE), docetaxel, vincristine, paclitaxel;

aromatase inhibitors: aminoglutethimide, atamestane (BioMedicines), letrozole, anastrazole, YM-511 (Yamanouchi), formestane, exemestane;

thymidylate synthase inhibitors: pemetrexed (Eli Lilly), ZD-9331 (BTG), nolatrexed (Eximias), CoFactor™ (BioKeys);

dna antagonists: trabectedin (PharmaMar); glufosfamide (Baxter International), albumin+32P (Isotope Solutions), thymectacin (NewBiotics), edotreotide (Novartis), mafosfamide (Baxter International), apaziquone (Spectrum Pharmaceuticals), 06 benzyl guanine (Paligent);

farnesyltransferase inhibitors: arglabin (NuOncology Labs), lonafarnib (Schering-Plough), BAY-43-9006 (Bayer), tipifarnib (Johnson & Johnson), perillyl alcohol (DOR BioPharma);

pump inhibitors: CBT-1 (CBA Pharma), tariquidar (Xenova), MS-209 (Schering AG), zosuquidar trihydrochloride (Eli Lilly), biricodar dicitrate (Vertex);

histone acetyltransferase inhibitors: tacedinaline (Pfizer), SAHA (Aton Pharma), MS-275 (Schering AG), pivaloyloxymethyl butyrate (Titan), depsipeptide (Fujisawa);

metalloproteinase inhibitors: Neovastat (Aeterna Laboratories), marimastat (British Biotech), CMT-3 (CollaGenex), BMS-275291 (Celltech);

ribonucleoside reductase inhibitors: gallium maltolate (Titan), triapine (Vion), tezacitabine (Aventis), didox (Molecules for Health);

tnf alpha agonists/antagonists: virulizin (Lorus Therapeutics), CDC-394 (Celgene), revimid (Celgene); endothelin a receptor antagonist: atrasentan (Abbott), ZD-4054 (AstraZeneca), YM-598 (Yamanouchi); retinoic acid receptor agonists: fenretinide (Johnson & Johnson), LGD-1550 (Ligand), alitretinoin (Ligand);

immuno-modulators: Pembrolizumab (formerly lambrolizumab, brand name Keytruda); interferon, oncophage (Antigenics), GMK (Progenics), adenocarcinoma, vaccine (Biomira), CTP-37 (AVI BioPharma), IRX-2 (Immuno-Rx), PEP-005 (Peplin Biotech), synchrovax vaccines (CTL Immuno), melanoma vaccine (CTL Immuno), p21 RAS vaccine (GemVax), MAGE-A3 (GSK), nivolumab (BMS), abatacept (BMS), dexosome therapy (Anosys), pentrix (Australian Cancer Technology), ISF-154 (Tragen), cancer vaccine (Intercell), norelin (Biostar), BLP-25 (Biomira), MGV (Progenics), ß-alethine (Dovetail), CLL therapy (Vasogen), Ipilimumab (BMS), CM-10 (cCam Biotherapeutics), MPDL3280A (Genentech);

hormonal and antihormonal agents: estrogens, conjugated estrogens, ethinyl estradiol, chlortrianisen, idenestrol, hydroxyprogesterone caproate, medroxyprogesterone, testosterone, testosterone propionate, fluoxymesterone, methyltestosterone, diethylstilbestrol, megestrol, bicalutamide, flutamide, nilutamide, dexamethasone, prednisone, methylprednisolone, prednisolone, aminoglutethimide, leuprolide, octreotide, mitotane, P-04 (Novogen), 2-methoxyestradiol (EntreMed), arzoxifene (Eli Lilly), tamoxifen, toremofine, goserelin, Leuporelin, bicalutamide;

photodynamic agents: talaporfin (Light Sciences), Theralux (Theratechnologies), motexafin gadolinium (Pharmacyclics), Pd-bacteriopheophorbide (Yeda), lutetium texaphyrin (Pharmacyclics), hypericin; and kinase inhibitors: afatinib, osimertinib, poziotinib (Spectrum), imatinib (Novartis), leflunomide (Sugen/Pharmacia), ZD1839 (AstraZeneca), erlotinib (Oncogene Science), canertinib (Pfizer), squalamine (Genaera), SU5416 (Pharmacia), SU6668 (Pharmacia), ZD4190 (AstraZeneca), ZD6474 (AstraZeneca), vatalanib (Novartis), PKI166 (Novartis), GW2016 (GlaxoSmithKline), EKB-509 (Wyeth), trastuzumab (Genentech), OSI-774 (Tarceva™), CI-1033 (Pfizer), SU11248 (Pharmacia), RH3 (York Medical), Genistein, Radicinol, Met-MAb (Roche), EKB-569 (Wyeth), kahalide F (PharmaMar), CEP-701 (Cephalon), CEP-751 (Cephalon), MLN518 (Millenium), PKC412 (Novartis), Phenoxodiol (Novogen), C225 (ImClone), rhu-Mab (Genentech), MDX-H210 (Medarex), 2C4 (Genentech), MDX-447 (Medarex), ABX-EGF (Abgenix), IMC-1C11 (ImClone), Tyrphostins, Gefitinib (Iressa), PTK787 (Novartis), EMD 72000 (Merck), Emodin, Radicinol, Vemurafenib (B-Raf enzyme inhibitor, Daiichi Sankyo), SR-27897 (CCK A inhibitor, Sanofi-Synthelabo), tocladesine (cyclic AMP agonist, Ribapharm), alvocidib (CDK inhibitor, Aventis), CV-247 (COX-2 inhibitor, Ivy Medical), P54 (COX-2 inhibitor, Phytopharm), CapCell™ (CYP450 stimulant, Bavarian Nordic), GCS-100 (gal3 antagonist, GlycoGenesys), G17DT immunogen (gastrin inhibitor, Aphton), efaproxiral (oxygenator, Allos Therapeutics), PI-88 (heparanase inhibitor, Progen), tesmilifene (histamine antagonist, YM BioSciences), histamine (histamine H2 receptor agonist, Maxim), tiazofurin (IMPDH inhibitor, Ribapharm), cilengitide (integrin antagonist, Merck KGaA), SR-31747 (IL-1 antagonist, Sanofi-Synthelabo), CCI-779 (mTOR kinase inhibitor, Wyeth), exisulind (PDE V inhibitor, Cell Pathways), CP-461 (PDE V inhibitor, Cell Pathways), AG-2037 (GART inhibitor, Pfizer), WX-UK1 (plasminogen activator inhibitor, Wilex), PBI-1402 (PMN stimulant, ProMetic LifeSciences), bortezomib (proteasome inhibitor, Millennium), SRL-172 (T cell stimulant, SR Pharma), TLK-286 (glutathione S transferase inhibitor, Telik), PT-100 (growth factor agonist, Point Therapeutics), midostaurin (PKC inhibitor, Novartis), bryostatin-1 (PKC stimulant, GPC Biotech), CDA-II (apoptosis promotor, Everlife), SDX-101 (apoptosis promotor, Salmedix), rituximab (CD20 antibody, Genentech, carmustine, Mitoxantrone, Bleomycin, Absinthin, Chrysophanic acid, Cesium oxides, BRAF inhibitors, PDL1 inhibitors, MEK inhibitors, bevacizumab, angiogenesis inhibitors, dabrafenib, ceflatonin (apoptosis promotor, ChemGenex); BCX-1777 (PNP inhibitor, BioCryst), ranpirnase (ribonuclease stimulant, Alfacell), galarubicin (RNA synthesis inhibitor, Dong-A), tirapazamine (reducing agent, SRI International), N, acetylcysteine (reducing agent, Zambon), R-flurbiprofen (NF-kappaB inhibitor, Encore), 3CPA (NF-kappaB inhibitor, Active Biotech), seocalcitol (vitamin D receptor agonist, Leo), 131-I-TM-601 (DNA antagonist, TransMolecular), eflornithine (ODC inhibitor, ILEX Oncology), minodronic acid (osteoclast inhibitor, Yamanouchi), indisulam (p53 stimulant, Eisai), aplidine (PPT inhibitor, PharmaMar), gemtuzumab (CD33 antibody, Wyeth Ayerst), PG2 (hematopoiesis enhancer, Pharmagenesis), Immunol™ (triclosan oral rinse, Endo), triacetyluridine (uridine prodrug, Wellstat), SN-4071 (sarcoma agent, Signature BioScience), TransMID-107™ (immunotoxin, KS Biomedix), PCK-3145 (apoptosis promotor, Procyon), doranidazole (apoptosis promotor, Pola), CHS-828 (cytotoxic agent, Leo), trans-retinoic acid (differentiator, NIH), MX6 (apoptosis promotor, MAXIA), apomine (apoptosis promotor, ILEX Oncology), urocidin (apoptosis promotor, Bioniche), Ro-31-7453 (apoptosis promotor, La Roche), brostallicin (apoptosis promotor, Pharmacia), β-lapachone, gelonin, cafestol, kahweol, caffeic acid, Tyrphostin AG, PD-1 inhibitors, CTLA-4 inhibitors, sorafenib, BRAF inhibitors, mTOR inhibitors (e.g. Vistusertib, everolimus/Afinitor, rapamycin, dactolisib, BGT226, SF1126, PKI-587, NVPBE235) and Pan-HER inhibitor (e.g. afatinib, neratinb, AC480).

In some embodiments, the agent for chemotherapy is selected from bevacizumab, bortezomib, capecitabine, cetuximab, fluorouracil, imatinib, irinotecan, leucovorin, oxaliplatin, panitumumab, pemetrexed, temozolomide, cisplatin, paclitaxel, erlotinib, sunitinib, lapatinib, sorafenib, carboplatin, doxorubicin, docetaxel, gemcitabine, etoposide, gefitinib, PD153035, cetuximab, bevacizumab, panitumumab, trastuzumab, anti-c-Met antibodies, gefitinib, ZD6474, EMD-72000, pariitumab, ICR-62, CI-1033, lapatinib, AEE788, EKB-569, EXEL 7647/EXEL 0999, erlotinib, imatinib, sorafinib, sunitinib, dasatinib, vandetinib, temsirolimus, PTK787, pazopanib, AZD2171, everolimus, seliciclib, AMG 706, axitinib, PD0325901, PKC-412, CEP701, XL880, bosutinib, BIBF1120, BIBF1120, nilotinib, AZD6244, HKI-272, MS-275, BI2536, GX15-070, AZD0530, enzastaurin, MLN-518, ARQ197, CM101, IFN-.alpha., IL-12, platelet factor-4, suramin, SU5416, thrombospondin, VEGFR antagonists, angiostatic steroids plus heparin, Cartilage-Derived Angiogenesis Inhibitory Factor, matrix metalloproteinase inhibitors, batimastat, marimastat, angiostatin, endostatin, 2-methoxyestradiol, tecogalan, thrombospondin, .alpha.V.beta.3 inhibitors, linomide, and ADH-1, chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL119, dacarbazine, chlormethine, bendamustine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylenemelamine, procarbazin, doxorubicin, daunorubicin, epirubicin, idarubicin, anthracenedione, mitoxantrone, mitomycin C, bleomycin, dactinomycin, plicatomycin, irinotecan, camptothecin, rubitecan, belotecan, etoposide, teniposide, topotecan, paclitaxel, taxol, docetaxel, BMS-275183, xyotax, tocosal, vinorlebine, vincristine, vinblastine, vindesine, vinzolidine, etoposide, teniposide, ixabepilone, larotaxel, ortataxel, tesetaxel, ispinesib, fluorouracil, floxuridine, methotrexate, xeloda, arranon, leucovorin, hydroxyurea, thioguanine, mercaptopurine, cytarabine, pentostatin, fludarabine phosphate, cladribine, asparaginase, gemcitabine, pemetrexed, bortezomib, aminopterin, raltitrexed, clofarabine, enocitabine, sapacitabine, azacitidine.

Further examples of agent for chemotherapy include SHP2 inhibitors (e.g. RMC-4550 and RMC-4630), phosphatase inhibitors (e.g. Tautomycin), CDK 4/6 inhibitors (abemaciclib (Lilly), palbociclib (Pfizer)), protein-protein interaction disruptors (BI 1701963), HSP90 inhibitor, tubulin inhibitor, apoptosis inhibitor, chemopreventative agent, and therapies targeting PBK/AKT/mTOR pathway.

Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. Another example is Trastuzumab duocarmazine. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

Examples of immunotherapies include immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons a, b, and g IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

Further examples of agents for use in combination with the compound of Formula I or its salt include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy. In some embodiments, the agents for use in combination with the compound of Formula I or its salt include one or more of bortezumib, taxol, aromatase inhibitor, and tazemetostat (ezh2 inhibitor).

In some embodiments, the disease or condition is autoimmune. Autoimmune diseases associated with type 1 interferon include, but are not limited to Systemic lupus erythematosus, Psoriasis, insulin-dependent diabetes mellitus (IDDM), dermatomyositis and Sjogren's syndrome (SS).

In some embodiments, the disease or condition is inflammation, which may be inflammation of any tissue and organs of the body, including for example musculoskeletal inflammation, vascular inflammation, neural inflammation, digestive system inflammation, ocular inflammation, inflammation of the reproductive system, and other inflammation, as exemplified below.

In some embodiments, the disease or condition is selected from glioblastomas, diffuse intrinsic pontine glioma (DIPG), T-cell acute lymphoblastic leukemia, acute myeloid leukemia, diffuse large B-cell lymphoma, neuroblastoma, prostate cancer, gastric cancer, multiple myeloma, rheumatoid arthritis, other arthritis, and bone metastases. In some embodiments, the disease is DIPG.

The compound of Formula I or a pharmaceutical composition thereof may be used in combination with or include one or more other therapeutic agents, for example selected from NSAIDS, corticosteroids, COX-2 inhibitors, cytokine inhibitors, anti-TNF agents, inhibitors oncostatin M, antimalarials, immunosuppressive and cytostatics.

In some embodiments of the method disclosed herein, the subjected has been determined to have a mutation selected from mutation of H3K27M, mutation of TP53 (H3.3 and H3.1 K27M-mutant DIPG), and mutation of ACVR1 (H3.1 K27M-mutant DIPG). In some embodiments, the subjected has been determined to have a mutation of H3K27M. In some embodiments, the method further includes a step of determining the subject as having one or more the above mutations.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a viral infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication, and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively, dosages may be based and calculated upon the surface area of the patient, as understood by those of skill in the art.

The exact formulation, route of administration and dosage for the pharmaceutical compositions can be chosen by the individual physician in view of the patient's condition. (see e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively, the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety, which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

In some embodiments, in the pharmaceutical industry, it is standard practice to provide substantially pure material when formulating pharmaceutical compositions. Therefore, in some embodiments, "substantially pure" refers to the amount of purity required for formulating pharmaceuticals, which may include, for example, a small amount of other material that will not affect the suitability for pharmaceutical use. In some embodiments, the substantially pure compound contains at least about 96% of the compound by weight, such as at least about 97%, 98%, 99%, or 100% of the compound.

EXAMPLES

Example 1

Study of JMJD3 demethylase inhibitors. JMJD3 demethylase inhibitor GSK-J4 restores K27 methylation and compacts chromatin, while demonstrating potent anti-tumor activity, in vitro and in vivo. Because of its promising anti-tumor activities, GSK-J4 has been used to treat many kinds of tumors in preclinical models including T-cell acute lymphoblastic leukemia, acute myeloid leukemia, diffuse large B-cell lymphoma, neuroblastoma, prostate cancer, gastric cancer, and DIPG. The major challenge of GSK-J4 in clinical development is that GSK-J4 is a prodrug and is rapidly converted to the active drug GSK-JT in vivo (FIG. 1). The biodistribution study of brainstem tissue from mice that were euthanized at 3 hours after completion of GSK-J4 treatment, correspondingly demonstrated only GSK-J1 in the samples. The highly polar GSK-J1 compound, while effective in enzyme assays, has restricted cellular and brain permeability and therefore been rendered inactive if hydrolysed from GSK-J4 in vivo before reaching the vicinity of the target tumor. The development of novel compounds such as UR-8 offered desirable properties including good cellular and brain transport which is essential to improving in vivo efficacy. UR-8 showed apparent favorable biodistribution in the brainstem and selective cytotoxic activity against human K27M DIPG cells and intracranial xenografts. It also showed greater anti-tumor activity and survival benefit than that obtained by GSK-J4 in DIPG PDX models.

UR-8 has demonstrated selective cytotoxic activity against human K27M DIPG cells ($IC_{50}$ range=4 to 6 μM) in vitro and apparently transports the brain to a useful extent based on its in vivo stability and effectiveness. Indeed, UR-8 showed greater anti-tumor activity and survival benefit than that obtained by GSK-J4 treatment in intracranial (brainstem) human DIPG xenografted mice. This is despite its lower in vitro potency than GSK-J4/J1 in vitro.

Figure 2:
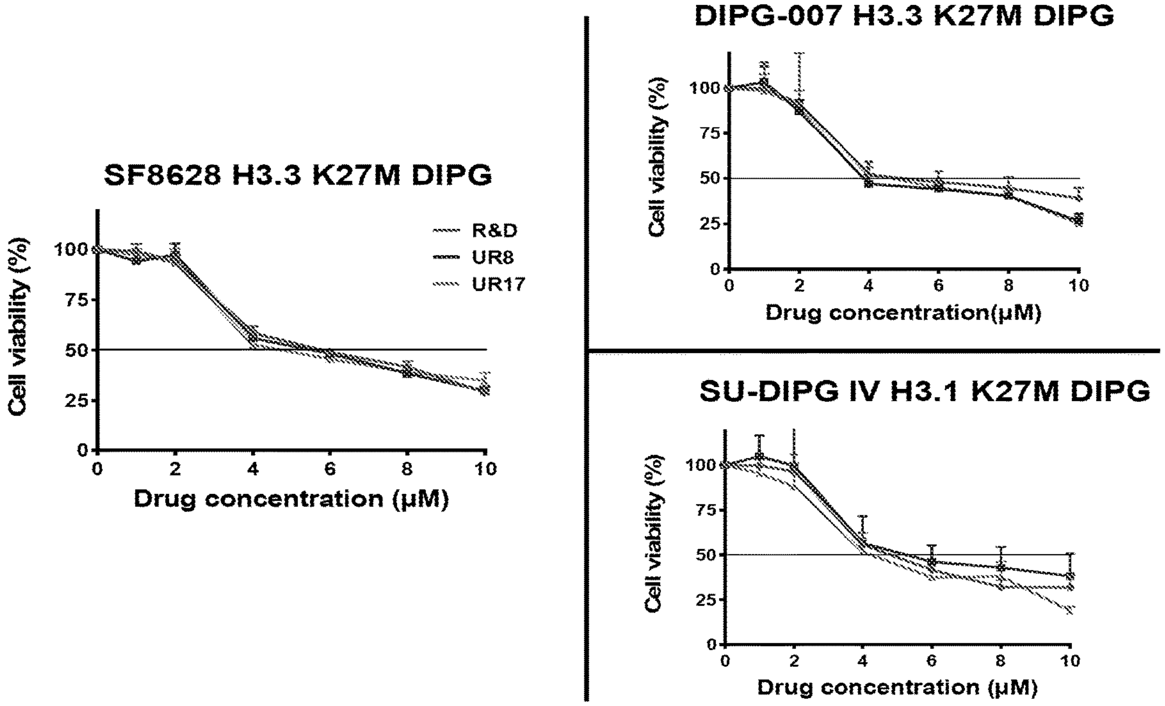

Specifically, UR-8 and UR-17 induced dose dependent inhibition of the growth of K27M DIPG cells—To determine the potential of the UR-analog series, UR-8 and UR-17 were selected for initial studies on DIPG cell growth. Thus, three H3K27M DIPG cell lines (H3.3 K27M SF8628, H3.3 K27M DIPG-007, and H3.1 K27M SU-DIPGIV) were treated with GSK-J4 (R&D System), UR-8, and UR-17 for 72 hours. All compounds induced a dose-dependent inhibition of DIPG cell growth, with IC50 at 4-6 μM (FIG. 2), indicating that UR-8 and UR-17 have similar cytotoxic activity with GSK-J4 against human H3K27M DIPG cells.

Example 2

UR-8 showed favorable biodistribution in the brainstem in compared to GSK-J4. UR-8 was administered by intraperitoneal injection to mice that were euthanized at 3 hours following UR-8 administration. Their brains were immediately resected, the brainstem was dissected from the surrounding brain, and the serum was collected by cardiac puncture. High-performance liquid chromatography (HPLC) analysis of tissue extracts revealed a detectable UR-8 concentration in the mice brainstem (8.77±2.37% of serum concentration) (Table 1), thereby supporting UR-8 access to the brain, and specifically to the brainstem, a site of DIPG development. GSK-J1 was highly detected in either serum and brainstem in the mice treated with GSK-J4 in compared to that of the mice treated with UR-8. GSK-J4 was not detected in any specimens from mice treated with GSK-J4. These results indicate that UR-8 transports to the brain with favorable concentrations in the brainstem and exhibits little conversion to the cell impermeable GSK-J1 in comparison. Furthermore, this data suggests that UR-8 is likely active in its original form and this subclass of inhibitors therefore offers great potential for clinical application relative to GSK-J4.

TABLE 1

| GSK-J1 and UR-8 concentration in brainstem and serum | |
|---|---|
| GSK-J1 concentration (ng/ml) | |
| Serum | |
| GSK-J4 treated | 31250 ± 18879 |
| UR-8 treated | 12090 ± 10196 |
| Brainstem | |
| GSK-J4 treated | 141.5 ± 50.2 |
| UR-8 treated | 110.35 ± 17.8 |
| UR-8 concentration (ng/ml) | |
| Serum | |
| UR-8 treated | 4455 ± 1576 |
| Brainstem | |
| UR-8 treated | 409.5 ± 243.9 |
| Brain penetration ratio (%) | |
| GSK-J4 treatment: | 0.61 ± 0.53 (GSK-J1) |
| UR-8 treatment: | 1.32 ± 0.96 (GSK-J1) |
| | 8.77 ± 2.37 (UR-8) |

Example 3

Figure 3A:
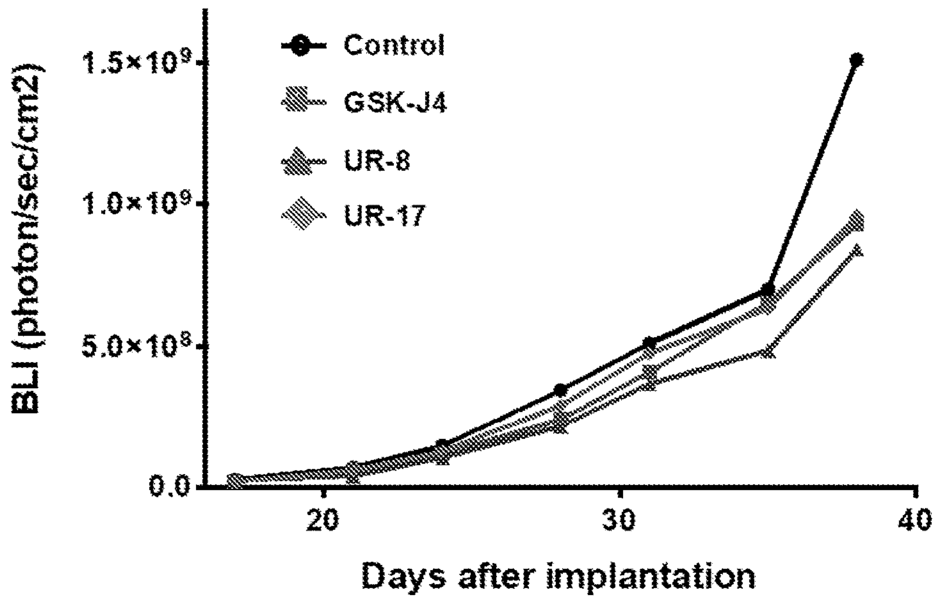
Figure 3B:
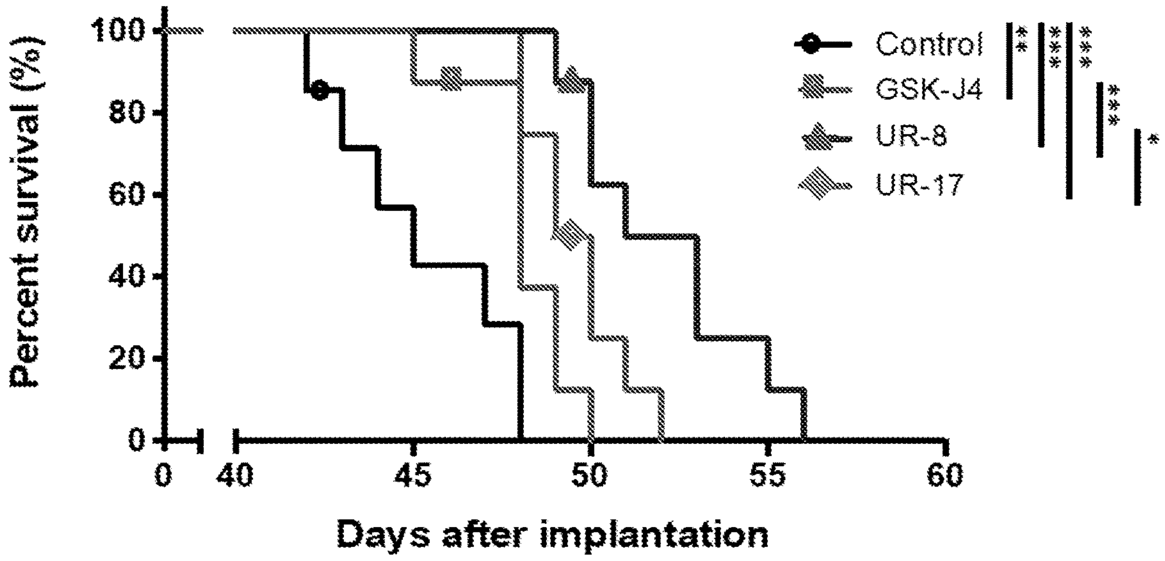
Figure 3C:
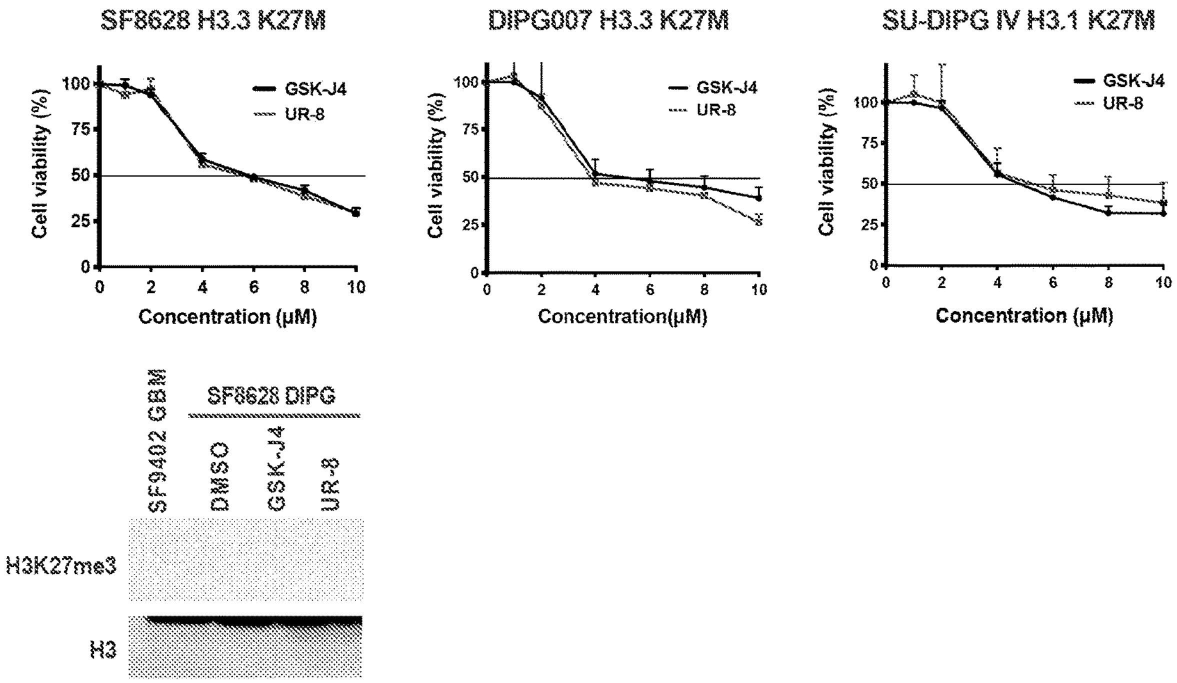

UR-8 inhibited tumor growth and prolonged survival of mice bearing human DIPG xenografts—Based on the biological effects of UR-analogs in vitro, it was hypothesized that UR-analogs would suppress tumor growth and increase survival in mice with orthotopic (brainstem) human DIPG xenografts. To determine in vivo anti-tumor activity of UR-analogs, the mice were implanted with SF8628 DIPG cells in the brainstem and were treated with 100 mg/kg of GSK-J4, UR-8, and UR-17 for 10 consecutive days. GSK-J4 resulted in reduced tumor growth rate and conferred substantial survival benefit against intracranial (brainstem) SF8628 DIPG xenografts, as indicated by bioluminescence monitoring [FIG. 3(A)] and survival of treated mice [FIG. 3(B)]. Similarly, UR-8 and UR-17 analogs provided a significant benefit. It was found that UR-8 treatment significantly increased therapeutic benefit, outperforming either GSK-J4 or UR-17 [FIG. 3(C)].

Example 4

Figure 4:
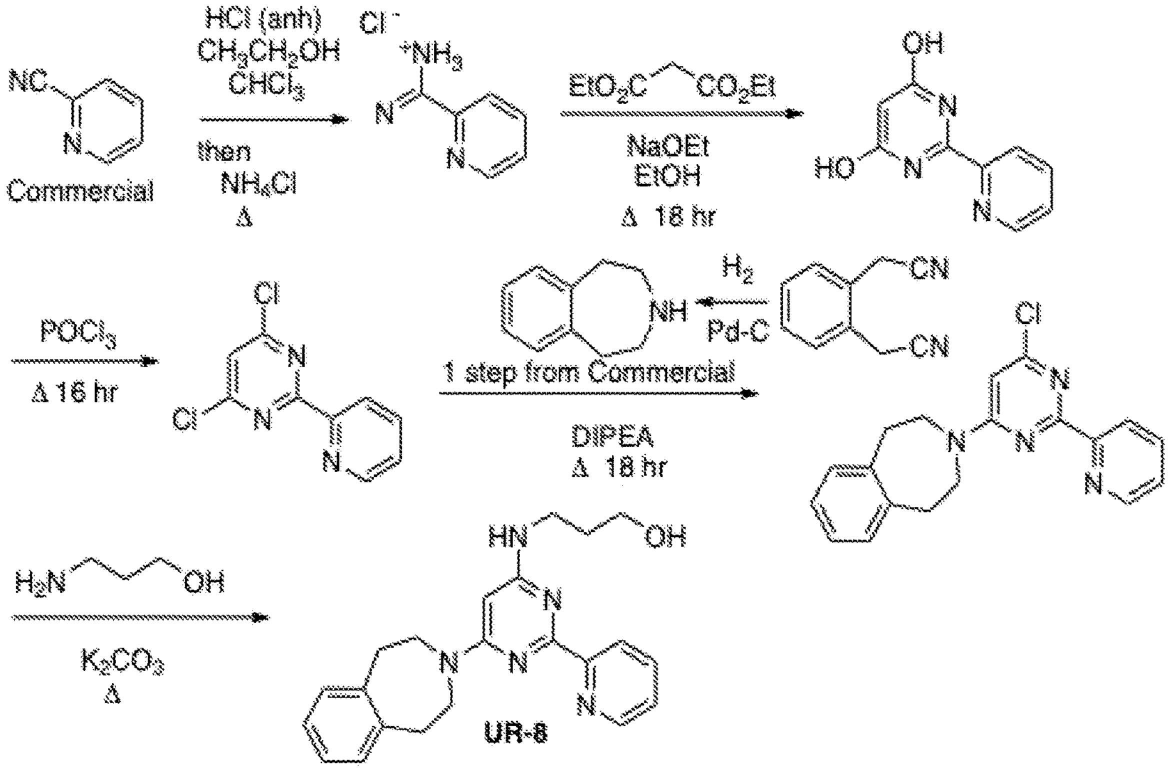
FIG. 4 shows an example synthesis route for UR-8.
Figure 5:
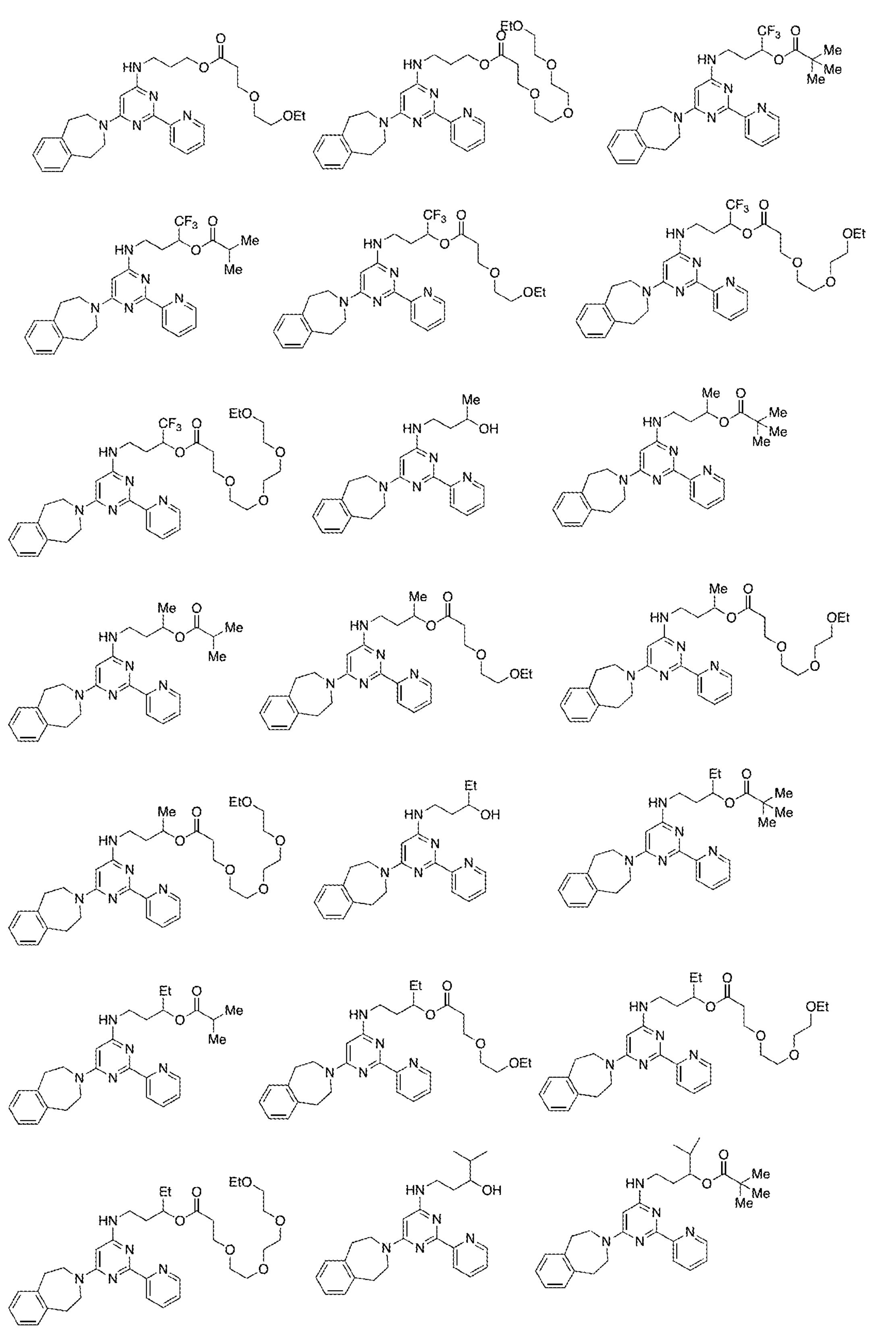
FIG. 5 shows examples compounds of Formula I.
Figure 5:
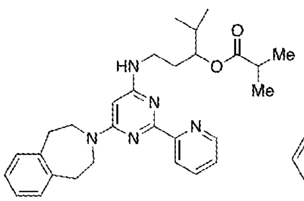
Figure 5:
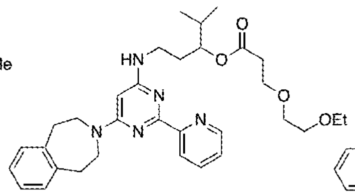
Figure 5:
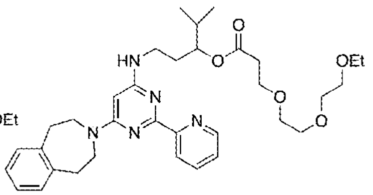
Figure 5:
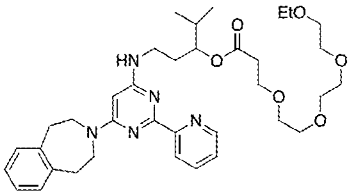
Figure 5:
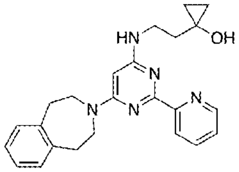
Figure 5:
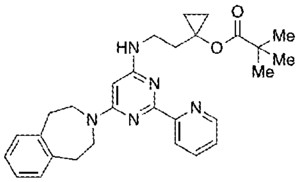
Figure 5:
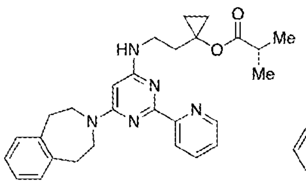
Figure 5:
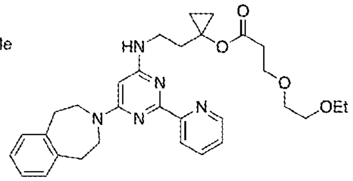
Figure 5:
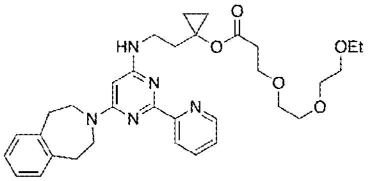
Figure 5:
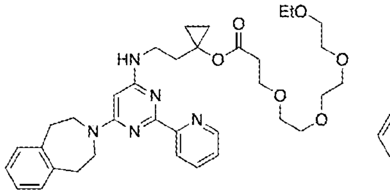
Figure 5:
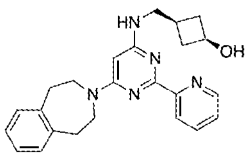
Figure 5:
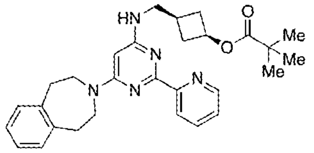
Figure 5:
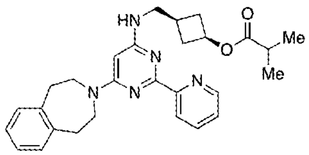
Figure 5:
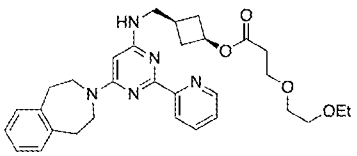
Figure 5:
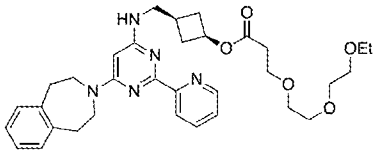
Figure 5:
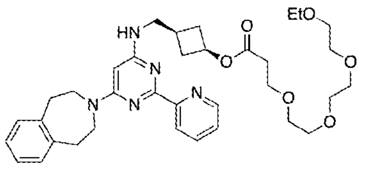
Figure 5:
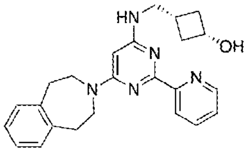
Figure 5:
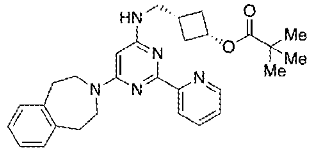
Figure 5:
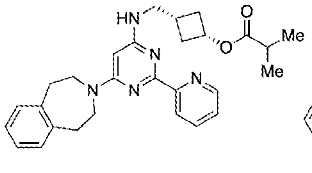
Figure 5:
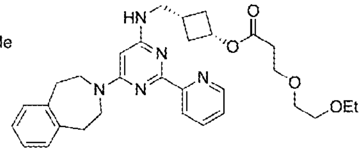
Figure 5:
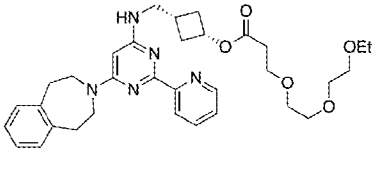
Figure 5:
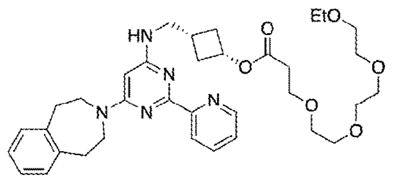
Figure 5:
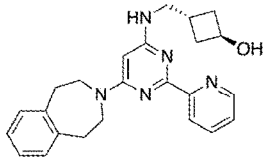
Figure 5:
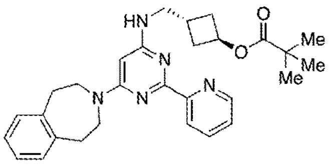
Figure 5:
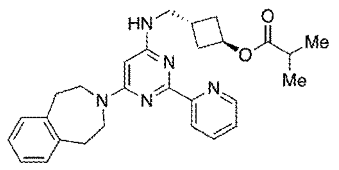
Figure 5:
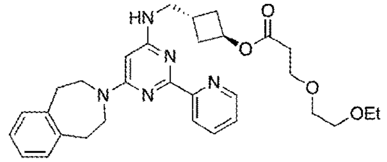
Figure 5:
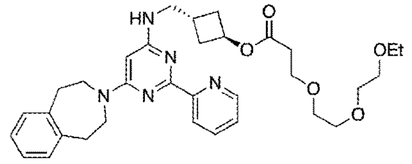
Figure 5:
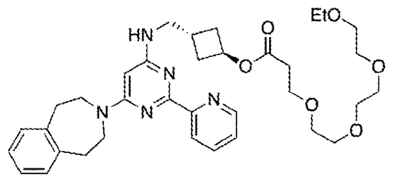
Figure 5:
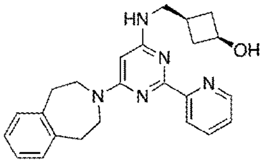
Figure 5:
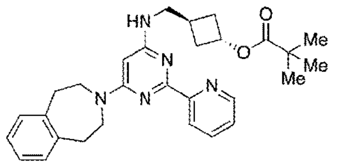
Figure 5:
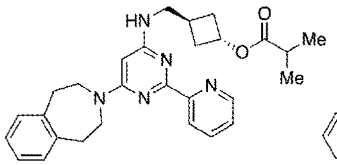
Figure 5:
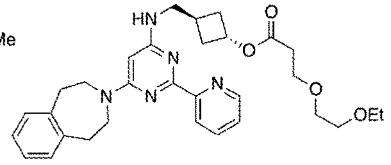
Figure 5:
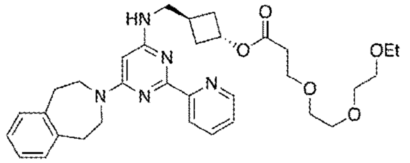
Figure 5:
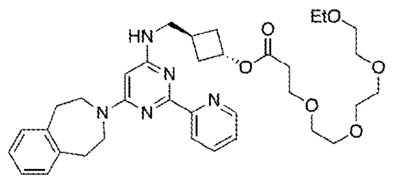
Figure 5:
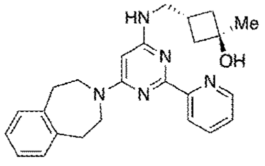
Figure 5:
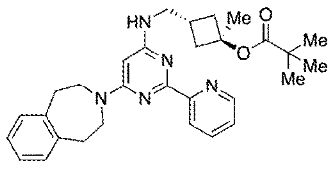
Figure 5:
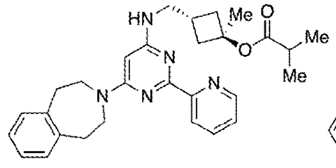
Figure 5:
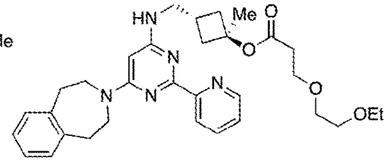
Figure 5:
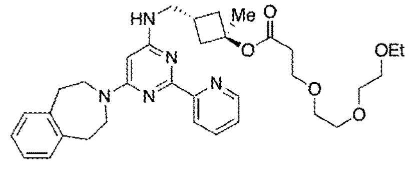
Figure 5:
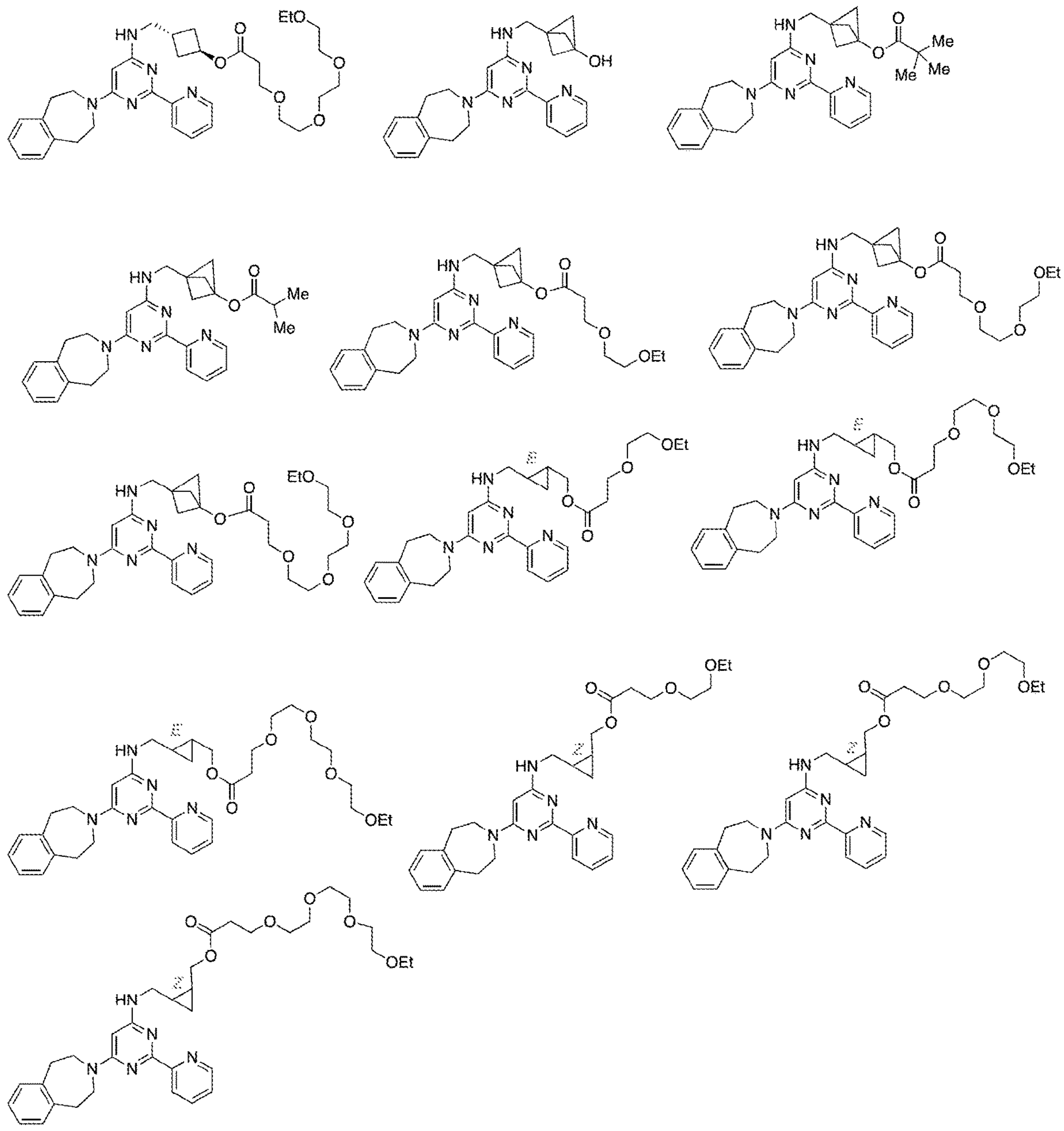

The synthesis and screening of UR-8 have shown promising cytotoxicity against established three H3K27M DIPG cell lines (SF8628, DIPG-007, and SU-DIPG IV) and is amenable to further structural modification to enhance potency and selectivity (FIG. 4). This synthetic route readily allows late-stage structural modifications of the side-chain. Thus, using this route, a small focused library of UR-8 analogs bearing both chains shortened and extended side-chains, is exemplified in FIG. 5.

Example 5

Synthesis of 3-((2-(pyridin-2-yl)-6-(1,2,4,5-tetrahydro-3H-benzo[d]azepin-3-yl)pyrimidin-4-yl)amino)propan-1-ol (UR-8)

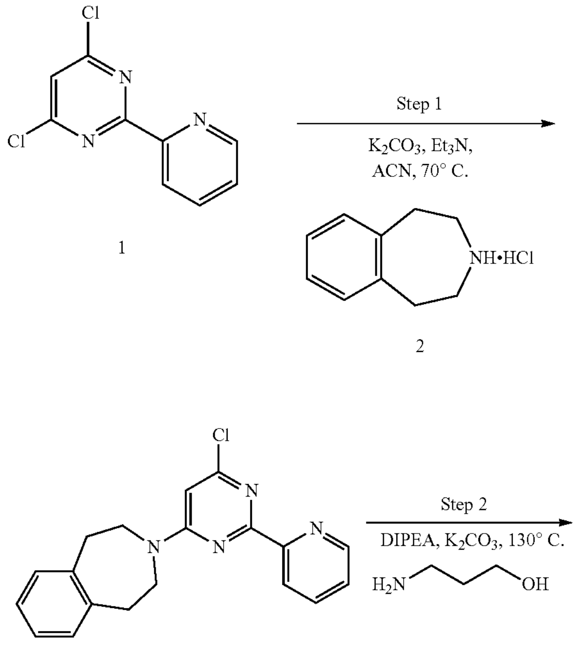

1

2

3

-continued

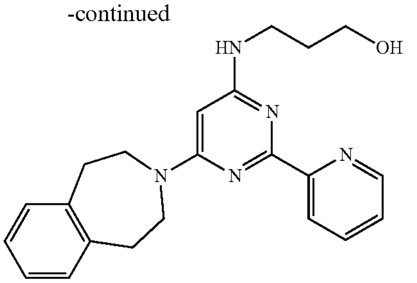

UR-8

Synthesis of 3-(6-chloro-2-(pyridin-2-yl)pyrimidin-4-yl)-2,3,4,5-tetrahydro-1H-benzo[d]azepine

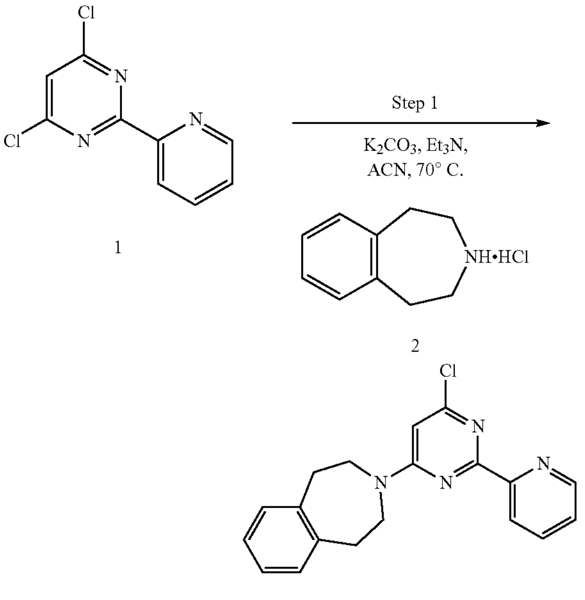

1 2 3

An oven dried round bottom flask was charged with a solution of 4,6-dichloro-2-(pyridin-2-yl)pyrimidine in anhydrous acetonitrile (11.2 g 49.54 mmol in 80 mL). Freshly activated potassium carbonate (13.7 g, 99.08 mmol), triethylamine (14 mL, 99.08 mmol) and 2,3,4,5-tetrahydro-1H-benzo[d]azepine hydrochloride (10 g, 54.5 mmol) were added and the contents were heated at 70° C. for 14 h. The reaction mixture was filtered and concentrated under reduced pressure. The crude mixture was diluted with ethyl acetate (500 mL) and washed with half saturated brine (2×100 mL), dried over anhydrous sodium sulphate, filtered and concentrated under reduced pressure. The crude mixture was purified by column chromatography on silica (0% to 3% methanol in dichloromethane) to yield 13.51 g (81%) of 3-(6-chloro-2-(pyridin-2-yl)pyrimidin-4-yl)-2,3,4,5-tetrahydro-1H-benzo[d]azepine as half white solid.

$^1H$ NMR (400 MHz, $CDCl_3$) δ 8.83 (d, J=4.0 Hz, 1H), 8.40 (d, J=7.9 Hz, 1H), 7.83 (t, J=7.8 Hz, 1H), 7.42-7.33 (m, 1H), 7.17 (s, 4H), 6.60 (s, 1H), 3.97 (s, 4H), 3.12-2.97 (m, 4H).

$^{13}C$ NMR (101 MHz, $CDCl_3$) δ 163.24, 162.15, 161.24, 154.51, 149.83, 140.01, 136.59, 130.03, 126.65, 124.78, 123.62, 100.72, 47.48, 36.54.

LC-MS (APCI) m/z $(M+H^{30})$ Calcd for $C_{19}H_{18}ClN_4$: 337.11 Found: 336.90.

Synthesis of 3-((2-(pyridin-2-yl)-6-(1,2,4,5-tetrahydro-3H-benzo[d]azepin-3-yl)pyrimidin-4-yl)amino)propan-1-ol (UR-8)

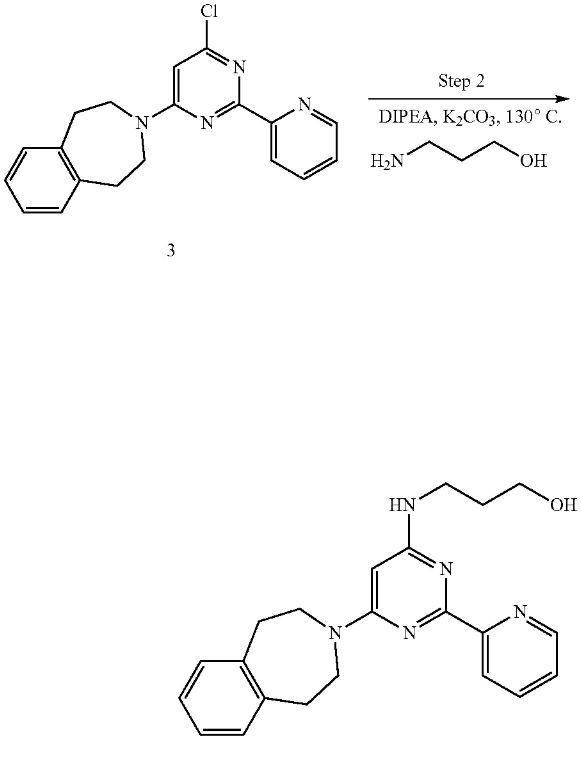

3 UR-8

An oven dried pressure tube was charged with 3-(6-chloro-2-(pyridin-2-yl)pyrimidin-4-yl)-2,3,4,5-tetrahydro-1H-benzo[d]azepine (5 g, 14.84 mmol). Freshly activated potassium carbonate 94 g, 29.68 mmol), DIPEA (5.17 mL, 29.68 mmol) and neat 3-aminopropan-1-ol (5 mL, 65.37 mmol) were added and the contents were heated at 130° C. for 8 h. The reaction mixture was diluted with dichloromethane (200 mL) and filtered. The organic layer washed with half saturated brine (3×30 mL), dried over anhydrous sodium sulphate, filtered, and concentrated. The crude mixture was purified by column chromatography on alumina (0% to 3% methanol in ethyl acetate) to yield 4.4 g (79%) of 3-((2-(pyridin-2-yl)-6-(1,2,4,5-tetrahydro-3H-benzo[d]azepin-3-yl)pyrimidin-4-yl)amino)propan-1-ol as half white solid.

$^1H$ NMR (400 MHz, $CDCl_3$): δ 8.75 (d, J=4.6 Hz, 1H), 8.45 (d, J=7.8 Hz, 1H), 7.79 (t, J=7.7 Hz, 1H), 7.32 (d, J=5.1 Hz, 1H), 7.15 (s, 4H), 5.54 (s, 1H), 4.81 (s, 1H), 3.91 (s, 4H), 3.69 (s, 4H), 3.05-2.88 (m, 4H), 1.77 (s, 2H).

$^{13}C$ NMR (101 MHz, $CDCl_3$): δ 164.63, 161.92, 155.67, 149.28, 140.92, 136.41, 129.90, 126.35, 124.26, 123.12, 80.87, 58.37, 47.32, 37.32, 36.84, 34.09.

LC-MS (APCI) m/z $(M+H^+)$ Calcd for $C_{22}H_{26}N_5O$: 376.21. Found: 376.30.

Example 6

Synthesis of 3-((2-(pyridin-2-yl)-6-(1,2,4,5-tetrahydro-3H-benzo[d]azepin-3-yl)pyrimidin-4-yl)amino)propyl pivalate (UR-95)

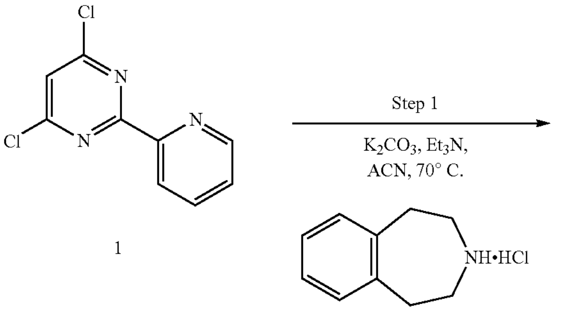

1

2

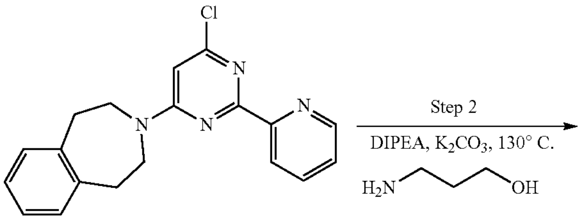

3

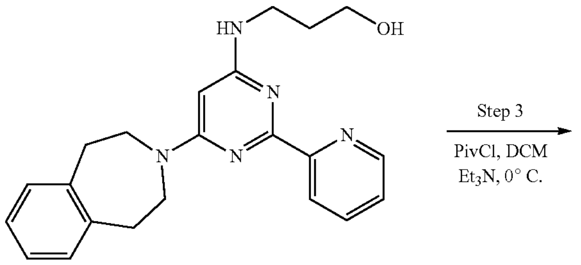

UR-8

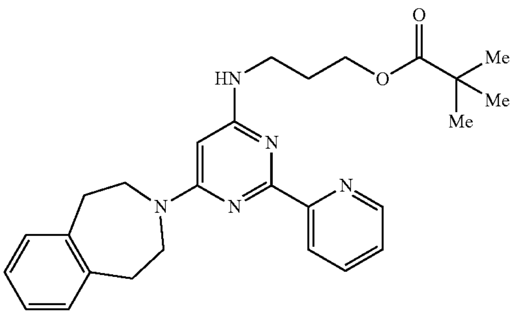

UR-95

Synthesis of 3-((2-(pyridin-2-yl)-6-(1,2,4,5-tetrahydro-3H-benzo[d]azepin-3-yl)pyrimidin-4-yl)amino)propyl pivalate (UR-95)

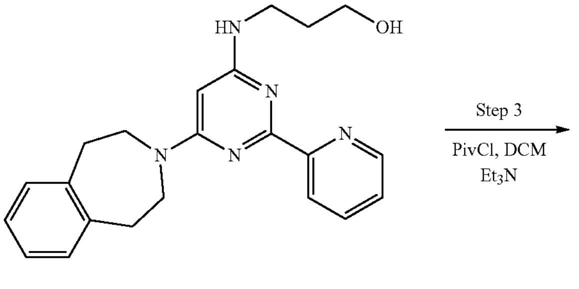

UR-8

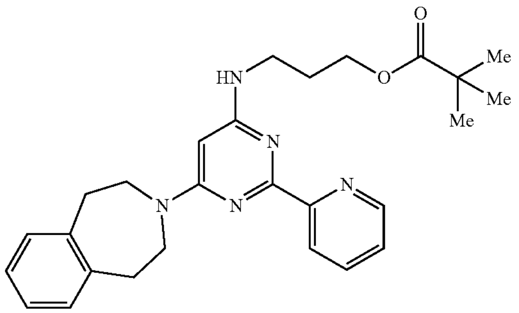

UR-95

An oven dried round bottom flask was charged with a solution of 3-((2-(pyridin-2-yl)-6-(1,2,4,5-tetrahydro-3H-benzo[d]azepin-3-yl)pyrimidin-4-yl)amino)propan-1-ol in anhydrous dichloromethane (1.64 g, 4.37 mmol in 10 mL). After cooling to 0° C., neat DIPEA (0.76 mL, 4.37 mmol) was added. A solution of pivaloyl chloride in anhydrous dichloromethane (0.5 g, 4.16 mmol in 5 mL) was added dropwise for a period of 30 min and the contents were stirred at 0° C. for 12 h. The reaction mixture was quenched with an aqueous solution of sodium bicarbonate (10 ml). After diluting with dichloromethane (50 mL), the organic layer was separated and washed with brine (1×20 mL), dried over sodium sulphate, filtered, and concentrated under reduced pressure. The crude mixture was purified by column chromatography on alumina (0% to 2% methanol in ethyl acetate) to yield 1.48 g (74%) of 3-((2-(pyridin-2-yl)-6-(1,2,4,5-tetrahydro-3H-benzo[d]azepin-3-yl)pyrimidin-4-yl)amino)propyl pivalate as white solid.

$^1H$ NMR (400 MHz, $CDCl_3$): δ 8.74 (dd, $J_1$=0.8 Hz, $J_2$=4.4 Hz, 1H), 8.40. (d, J=7.6 Hz, 1H), 7.81-7.72 (m, 1H), 7.35-7.28 (m, 1H), 7.11 (s, 4H), 5.46 (s, 1H), 4.18 (t, J=6.8 Hz, 2H), 3.98-3.83 (m, 4H), 3.37 (t, J=6.8 Hz, 2H), 3.04-2.93 (m, 4H), 2.05-1.89 (m, 2H), 1.2 (s, 9H).

$^{13}C$ NMR (125 MHz, $CDCl_3$): δ 179.2, 164.53, 163.13, 162.74, 156.56, 150.18, 141.57, 137.21, 130.69, 121.17, 124.96, 124.13, 80.03, 62.47, 48.14, 39.42, 37.39, 29.21, 27.96.

LC-MS (APCI) m/z (M+H+) Calcd for $C_{27}H_{34}N_5O_2$: 460.26. Found: 460.21.

Example 7

Synthesis of 1,1,1-trifluoro-4-((2-(pyridin-2-yl)-6-(1,2,4,5-tetrahydro-3H-benzo[d]azepin-3-yl)pyrimidin-4-yl)amino)butan-2-ol (UR-97)

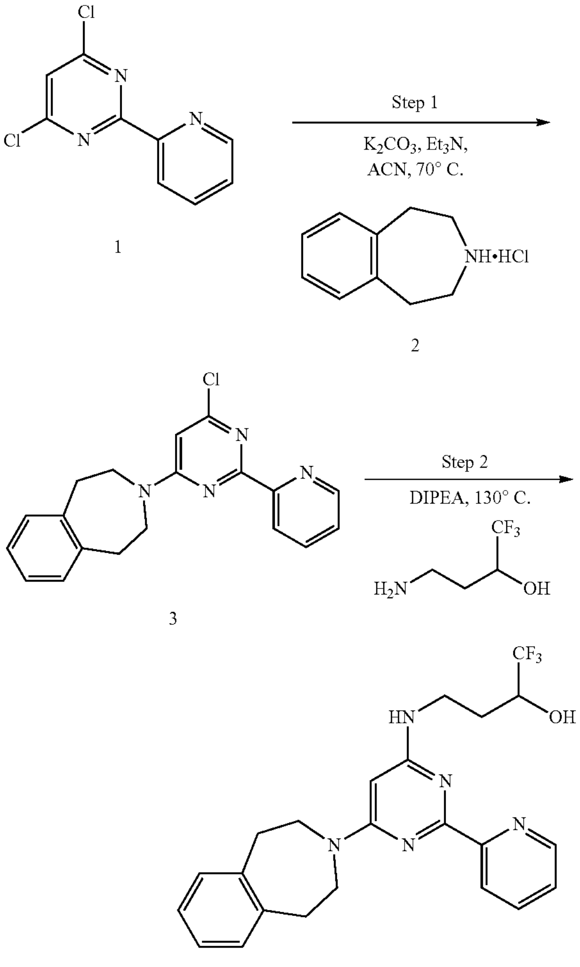

UR-97

Synthesis of 1,1,1-trifluoro-4-((2-(pyridin-2-yl)-6-(1,2,4,5-tetrahydro-3H-benzo[d]azepin-3-yl)pyrimidin-4-yl)amino)butan-2-ol (UR-97)

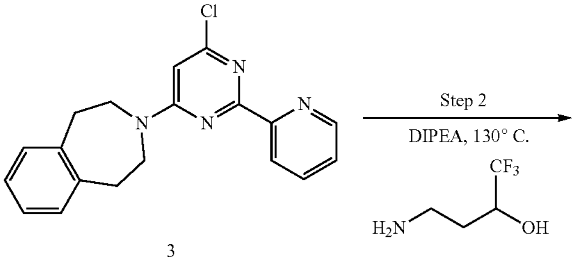

3

-continued

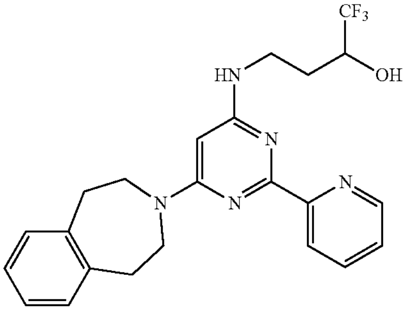

UR-97

An oven dried pressure tube was charged with 3-(6-chloro-2-(pyridin-2-yl)pyrimidin-4-yl)-2,3,4,5-tetrahydro-1H-benzo[d]azepine (1.5 g, 4.5 mmol). DIPEA (9.3 mL, 53.28 mmol) and neat 4-amino-1,1,1-trifluorobutan-2-ol hydrochloride (7.66 g, 53.28 mmol) were added and the contents were heated at 130° C. for 6 h. The reaction mixture was concentrated under reduced pressure and purified by column chromatography on alumina (0% to 3% methanol in ethyl acetate) to yield 1.28 g (65%) of 1,1,1-trifluoro-4-((2-(pyridin-2-yl)-6-(1,2,4,5-tetrahydro-3H-benzo[d]azepin-3-yl)pyrimidin-4-yl)amino)butan-2-ol as half white solid.

$^1H$ NMR (400 MHz, $CDCl_3$): δ 8.76-8.65 (m, 1H), 8.54-8.42 (m, 1H), 7.89-7.76 (m, 1H), 7.42-7.31 (m, 1H), 7.25 (s, 4H), 5.55 (s, 1H), 4.43-4.15 (m, 2H), 3.99-3.79 (m, 4H), 3.29-3.12 (m, 1H0, 2.99 (t, J=5.2 Hz, 4H), 1.87-1.71 (m, 2H).

$^{13}C$ NMR (125 MHz, $CDCl_3$): δ 165.20, 165.59, 162.08, 148.67, 141.61, 137.72, 130.71, 128.07, 127.19, 125.83, 125.49, 123.81, 82.52, 67.50 (q, J=30 Hz), 48.12, 37.56, 37.21, 33.82.

LC-MS (APCI) m/z (M+H$^+$) Calcd for $C_{23}H_{25}F_3N_5O$: 444.19. Found: 444.15.

Example 8

Synthesis of (2-(((2-(pyridin-2-yl)-6-(1,2,4,5-tetrahydro-3H-benzo[d]azepin-3-yl)pyrimidin-4-yl)amino)methyl)cyclopropyl)methanol (UR-100)

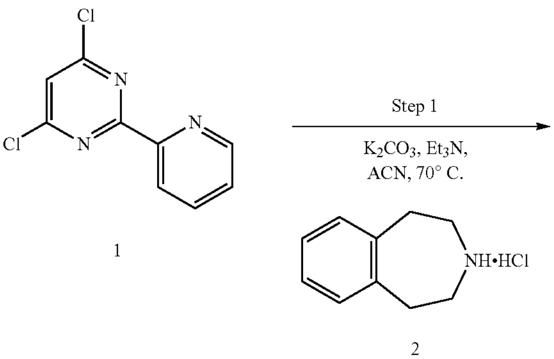

-continued

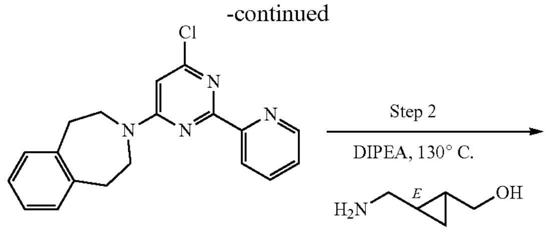

3

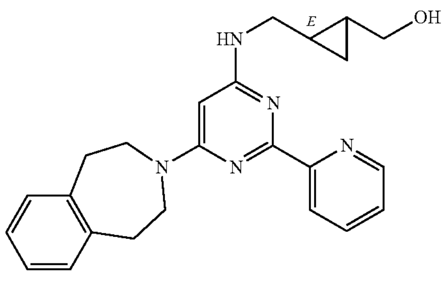

UR-100

Synthesis of E-(2-(((2-(pyridin-2-yl)-6-(1,2,4,5-tetrahydro-3H-benzo[d]azepin-3-yl)pyrimidin-4-yl)amino)methyl)cyclopropyl)methanol (UR-100)

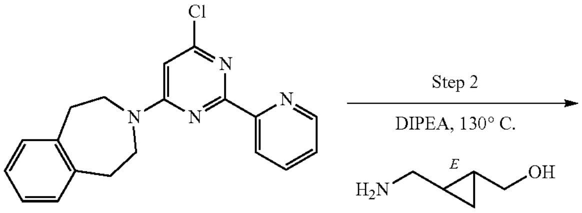

3

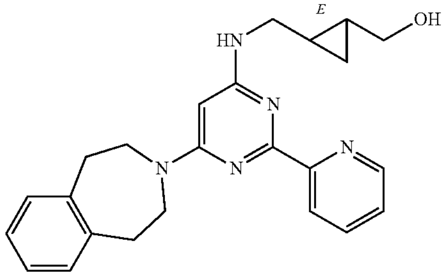

UR-100

An oven dried pressure tube was charged with 3-(6-chloro-2-(pyridin-2-yl)pyrimidin-4-yl)-2,3,4,5-tetrahydro-1H-benzo[d]azepine (0.15 g, 0.45 mmol mmol). DIPEA (0.93 mL, 5.328 mmol) and neat (2E-(aminomethyl)cyclopropyl)methanol (0.538 g, 5.328 mmol) were added and the contents were heated at 130° C. for 6 h. The reaction mixture was concentrated under reduced pressure and purified by column chromatography on alumina (0% to 3% methanol in ethyl acetate) to yield 0.11 g (62%) of E-(2-(((2-(pyridin-2-yl)-6-(1,2,4,5-tetrahydro-3H-benzo[d]azepin-3-yl)pyrimidin-4-yl)amino)methyl)-cyclopropyl)methanol as half white solid.

$^{1}$H NMR (400 MHz, $CD_3OD$): δ 8.68-8.58 (m, 1H), 8.36 (d, J=5 Hz, 1H), 7.95-7.85 (m, 1H), 7.49-7.36 (m, 1H), 7.11-6.91 (m, 4H), 5.65 (s, 1H), 3.93-76 (M, 4H), 3.49-3.39 (m, 1H), 3.39-3.31 (m, 1H), 3.29-3.15 (m, 2H), 3.01-2.85 (m, 4H), 1.11-0.91 (m, 2H), 0.61-0.39 (m, 2H).

$^{13}$C NMR (125 MHz, $CD_3OD$): δ 164.80, 162.98, 162.40, 149.03, 141.63, 137.78, 141.63, 137.78, 130.20, 126.73, 125.12, 124.19, 65.82, 47.89, 45.44, 37.04, 20.13, 17.11, 8.50.

LC-MS (APCI) m/z ($M+H^+$) Calcd for $C_{24}H_{28}N_5O$: 402.22. Found: 402.17.

Example 9

Synthesis of (2-(((2-(pyridin-2-yl)-6-(1,2,4,5-tetrahydro-3H-benzo[d]azepin-3-yl)pyrimidin-4-yl)amino)methyl)cyclopropyl)methanol (UR-101)

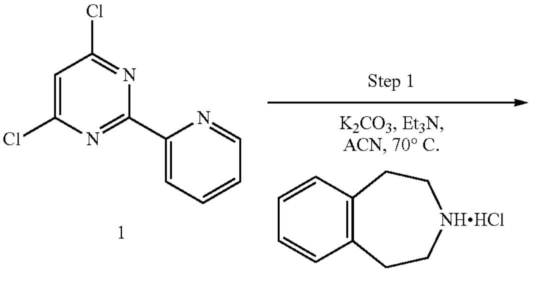

1

2

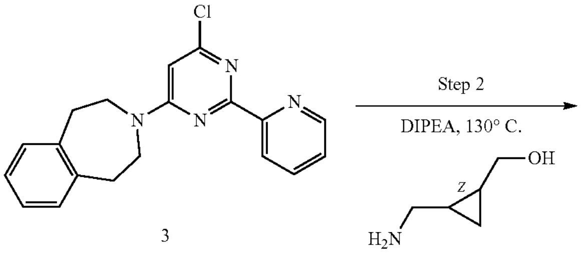

3

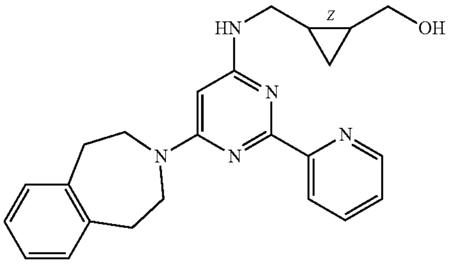

UR-101

Synthesis of (2-(((2-(pyridin-2-yl)-6-(1,2,4,5-tetrahydro-3H-benzo[d]azepin-3-yl)pyrimidin-4-yl)amino)methyl)cyclopropyl)methanol (UR-101)

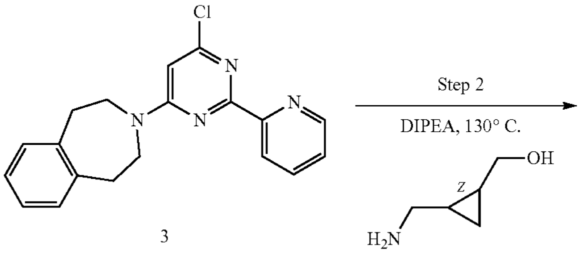

3

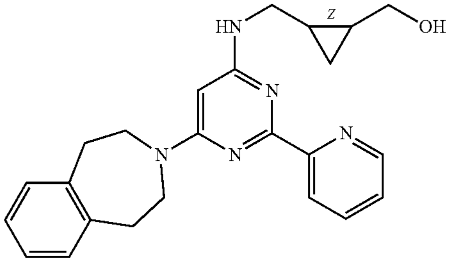

UR-101

An oven dried pressure tube was charged with 3-(6-chloro-2-(pyridin-2-yl)pyrimidin-4-yl)-2,3,4,5-tetrahydro-1H-benzo[d]azepine (0.15 g, 0.45 mmol mmol). DIPEA (0.93 mL, 5.328 mmol) and neat (2Z-(aminomethyl)cyclopropyl)methanol (0.538 g, 5.328 mmol) were added and the contents were heated at 130° C. for 6 h. The reaction mixture was concentrated under reduced pressure and purified by column chromatography on alumina (0% to 3% methanol in ethyl acetate) to yield 0.12 g (68%) of Z-(2-(((2-(pyridin-2-yl)-6-(1,2,4,5-tetrahydro-3H-benzo[d]azepin-3-yl)pyrimidin-4-yl)amino)methyl)-cyclopropyl)methanol as half white solid.

$^{1}$H NMR (500 MHz, $CD_3OD$): δ 8.63-8.56 (m, 1H), 8.36 (d, J=10 Hz, 1H), 7.48-7.39 (m, 1H), 7.49-7.35 (m, 1H), 7.15-6.98 (m, 4H), 5.66 (s, 1H), 3.95-3.83 (m, 4H), 3.81-3.71 (m, 1H), 3.54-3.45 (m, 2H), 3.39-3.26 (m, 2H), 2.99-2.87 (m, 4H), 1.35-1.12 (m, 2H), 0.84-0.76 (m, 1H), 0.29-0.21 (m, 1H).

$^{13}$C NMR (101 MHz, $CD_3OD$): δ 164.82, 162.99, 162.53, 156.75, 149.01, 141.64, 137.77, 130.20, 126.73, 125.10, 124.22, 80.93, 62.14, 47.84, 41.50, 37.06, 18.17, 16.05, 8.33.

LC-MS (APCI) m/z (M+H$^{+}$) Calcd for $C_{24}H_{28}N_5O$: 402.22. Found: 402.17.

Example 10

Synthesis of (2-(((2-(pyridin-2-yl)-6-(1,2,4,5-tetrahydro-3H-benzo[d]azepin-3-yl)pyrimidin-4-yl)amino)methyl)cyclopropyl)methyl pivalate (UR-102)

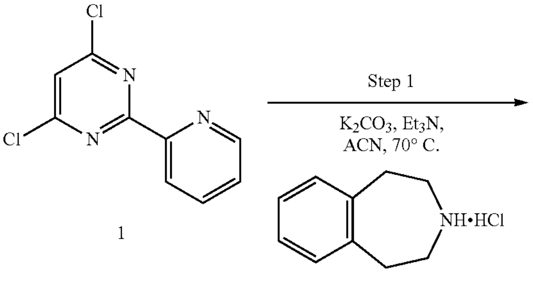

1

2

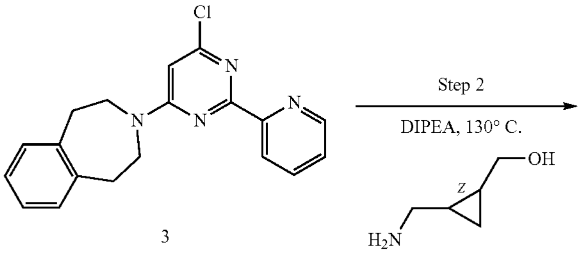

3

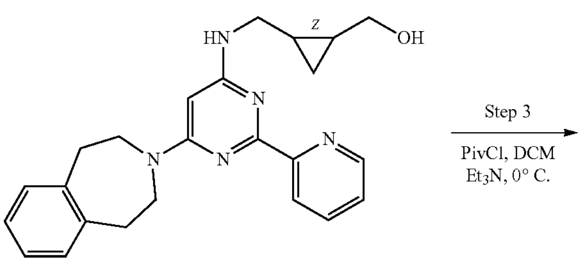

UR-101

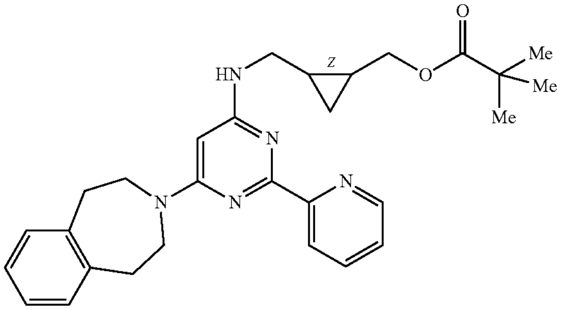

UR-102

Synthesis of (2-(((2-(pyridin-2-yl)-6-(1,2,4,5-tetrahydro-3H-benzo[d]azepin-3-yl)pyrimidin-4-yl)amino)methyl)cyclopropyl)methyl pivalate

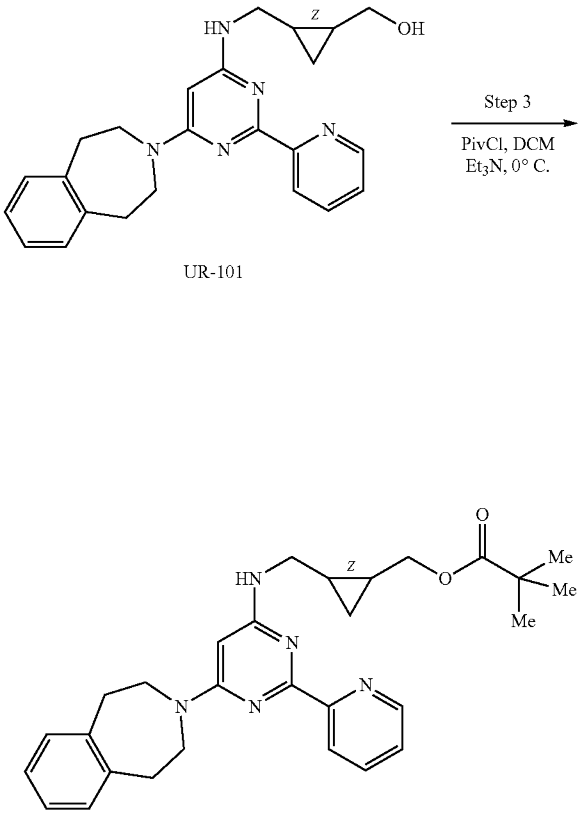

UR-101

UR-102

An oven dried round bottom flask was charged with a solution of (2-(((2-(pyridin-2-yl)-6-(1,2,4,5-tetrahydro-3H-benzo[d]azepin-3-yl)pyrimidin-4-yl)amino)methyl)cyclopropyl)methanol in anhydrous dichloromethane (155 mg, 0.386 mmol in 1 mL). After cooling to 0° C., neat triethylamine (0.05 mL, 0.394 mmol) and potassium carbonate (0.16 g, 1.158 mmol) were added. Neat pivaloyl chloride (0.05 mL, 0.397 mmol) was added and the contents were stirred at 0° C. for 8 h. The reaction mixture was quenched with an aqueous solution of sodium bicarbonate (1 mL). After diluting with dichloromethane (10 mL), the organic layer was washed with brine (1×5 mL), dried over sodium sulphate, filtered, and concentrated under reduced pressure. The crude mixture was purified by column chromatography on alumina (0% to 100% ethyl acetate in n-hexanes) to yield 87 mg (46%) of (2-(((2-(pyridin-2-yl)-6-(1,2,4,5-tetrahydro-3H-benzol[d]azepin-3-yl)pyrimidin-4-yl)amino)methyl)-cyclopropyl)methyl pivalate as white solid.

$^1$H NMR (400 MHz, $CDCl_3$): δ 8.78 (d, J=4 Hz, 1H), 8.42 (d, J=7.6 Hz, 1H), 7.85-7.71 (m, 1H), 7.41-7.29 (m, 1H), 7.14 (s, 4H), 5.44 (s, 1H), 4.39-4.25 (m, 1H), 4.09-3.85 (m, 5H), 3.39-3.21 (m, 2H), 3.08-2.91 (m, 4H), 1.47-1.21 (m, 12H), 0.96-0.76 (m, 2H), 0.42-0.31 (m, 1H).

LC-MS (APCI) m/z (M+H+) Calcd for $C_{29}H_{36}N_5O_2$: 486.28. Found: 486.23.

Example 11

Synthesis of N-hydroxy-3-((2-(pyridin-2-yl)-6-(1,2,4,5-tetrahydro-3H-benzo[d]azepin-3-yl)pyrimidin-4-yl)amino)propenamide (UR-96)

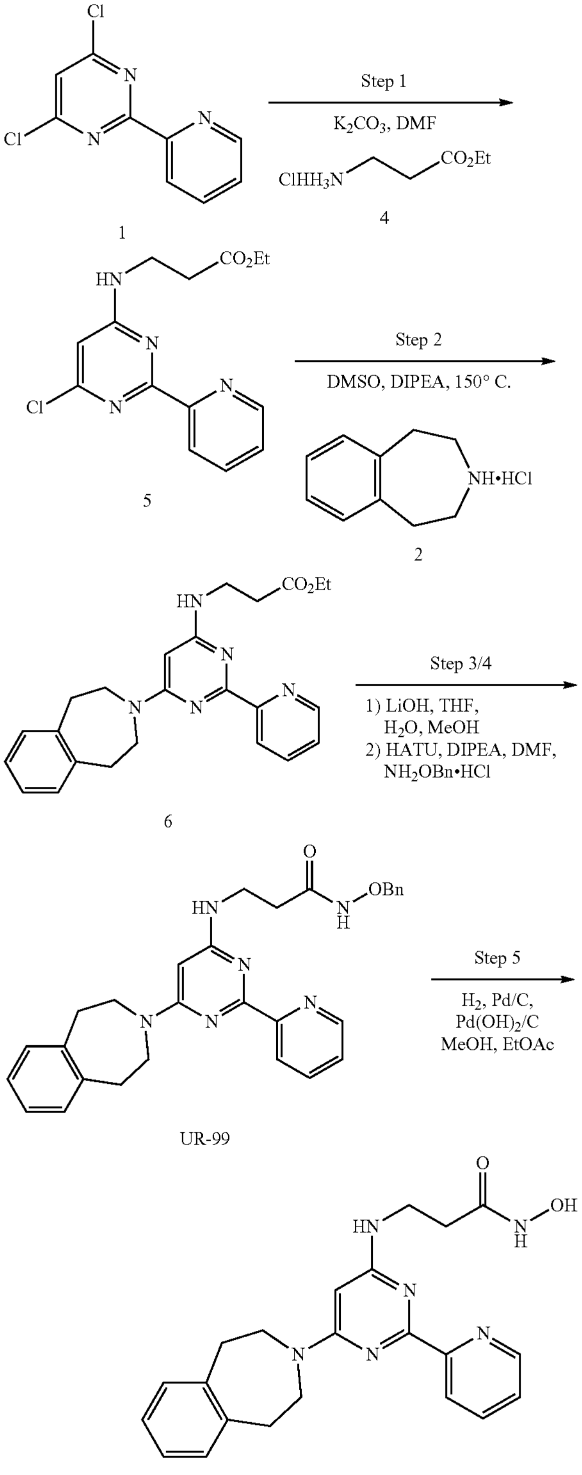

1

4

5

2

6

UR-99

UR-96

Synthesis of 3-((6-chloro-2-(pyridin-2-yl)pyrimidin-4-yl)amino)propanoate

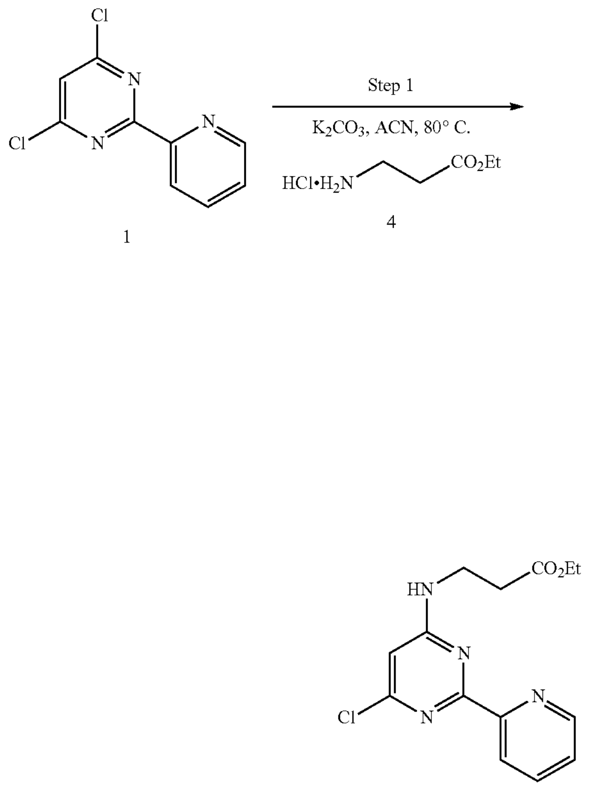

1 4 5

An oven dried round bottom flask was charged with a solution of 4,6-dichloro-2-(pyridin-2-yl)pyrimidine in anhydrous acetonitrile (5 g, 22.11 mmol in 30 mL). Freshly activated potassium carbonate (6.1 g, 44.22) triethylamine (6.1 mL, 44.22 mmol) and ethyl 3-aminopropanoate hydrochloride (3.7 g, 24.32 mmol) were sequentially added and the contents were heated at 80° C. for 14 h. The reaction mixture was filtered and concentrated under reduced pressure. The crude mixture was redissolved in water (50 mL) and extracted with dichloromethane (5×50 mL). The combined organic layer was washed with brine (2×100 mL), dried over anhydrous sodium sulphate, filtered, and concentrated under reduced pressure. The crude mixture was purified by column chromatography on silica (0% to 60% ethyl acetate in n-hexanes) to yield 5.53 g (81%) of ethyl 3-((6-chloro-2-(pyridin-2-yl)pyrimidin-4-yl)amino)propanoate as pale yellow solid.

$^1$H NMR (500 MHz, $CDCl_3$): δ 8.78-8.68 (m, 1H), 8.35 (d, J=10 Hz, 1H), 7.81-7.69 (m, 1H), 7.39-7.24 (m, 1H), 6.33 (s, 1H), 5.93 (s, 1H), 4.08 (q, J=7.5 Hz, 2H), 3.66 (bs, 2H), 2.39 (t, J=5 Hz, 2H) 1.19 (t, J=7.5 Hz, 3H).

$^{13}$C NMR (125 MHz, $CDCl_3$): δ 172.54, 164.32, 164.14, 161.37, 154.80, 150.50, 137.54, 125.71, 124.58, 61.66, 37.82, 34.53, 14.86.

LC-MS (APCI) m/z (M+H+) Calcd for $C_{14}H_{15}ClN_4O_2$: 307.09. Found: 307.05.

Synthesis of ethyl 3-((2-(pyridin-2-yl)-6-(1,2,4,5-tetrahydro-3H-benzo[d]azepin-3-yl)pyrimidin-4-yl)amino)propanoate

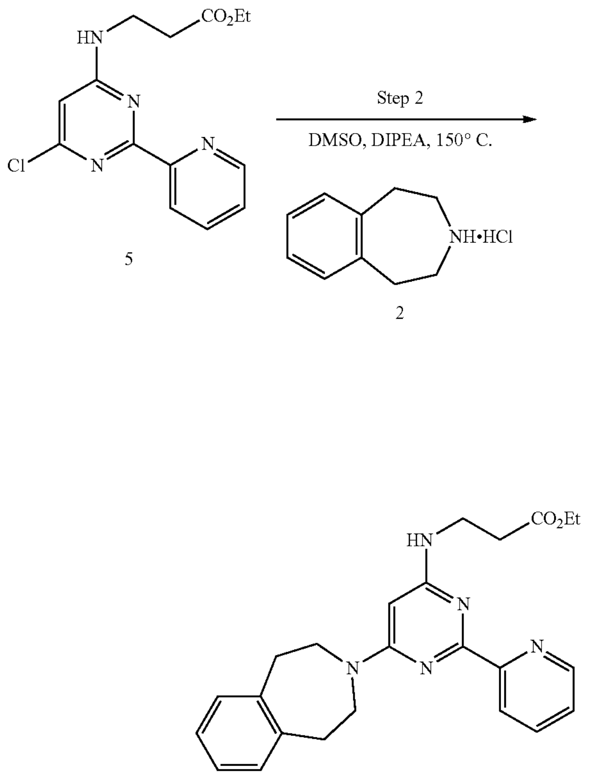

5 2 6

An oven dried round bottom flask was charged with a solution of ethyl 3-((6-chloro-2-(pyridin-2-yl)pyrimidin-4-yl)amino)propanoate in anhydrous dimethyl sulfoxide (3.9 g, 13 mmol in 6 mL). Neat DIPEA (4.6 mL, 26 mmol) and 2,3,4,5-tetrahydro-1H-benzo[d]azepine hydrochloride (2.4 g, 13 mmol) were added and the contents were heated at 160° C. for 18 h. The reaction mixture was concentrated under reduced pressure and the crude mixture was dissolved in dichloromethane (300 mL) It was washed with water (5×50 mL), brine (3×100 mL), dried over anhydrous sodium sulphate, filtered, and concentrated under reduced pressure. The crude mixture was purified by column chromatography on alumina (0% to 1% methanol in ethyl acetate) to yield 3.3 g (62%) of ethyl 3-((2-(pyridin-2-yl)-6-(1,2,4,5-tetrahydro-3H-benzo[d]azepin-3-yl)pyrimidin-4-yl)amino)propanoate as half white solid.

$^1$H NMR (400 MHz, $CDCl_3$): δ 8.76 (d, J=4 Hz, 1H), 8.42 (d, J=5.2 Hz, 1H), 7.85-7.74 (m, 1H), 7.38-7.28 (m 1H), 7.14 (s, 4H), 5.54 (s, 1H), 4.16 (q, J=7.2 Hz, 2H), 3.98-3.88 (m, 4H), 3.69-3.55 (m, 2H), 3.09-2.95 (m, 4H), 2.65 (t, J=8 Hz, 2H), 1.26 (t, J=7.2 Hz, 3H).

$^{13}$C NMR (125 MHz, $CDCl_3$): δ 172.60, 164.44, 163.12, 162.89, 156.66, 150.24, 141.62, 137.19, 130.70, 127.15, 124.91, 124.18, 80.16, 61.57, 48.14, 38.21, 37.62, 34.93, 14.94.

LC-MS (APCI) m/z (M+H+) Calcd for $C_{24}H_{28}N_5O_2$: 418.22. Found: 418.16.

Synthesis of N-(benzyloxy)-3-((2-(pyridin-2-yl)-6-(1,2,4,5-tetrahydro-3H-benzo[d]azepin-3-yl)pyrimidin-4-yl)amino)propenamide (UR-99)

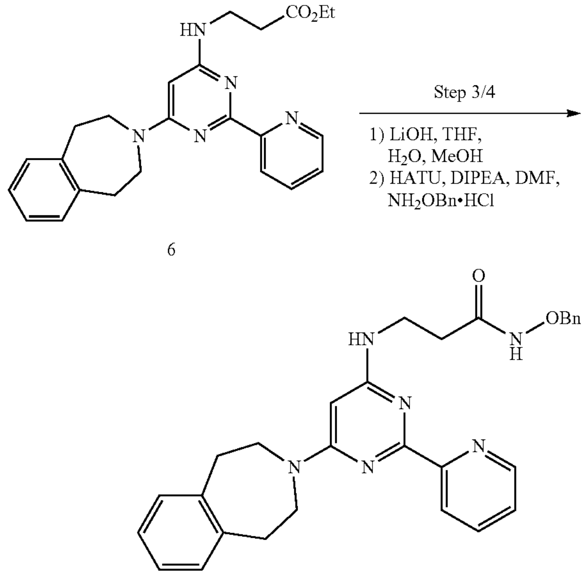

6

UR-99

A round bottom flask was charged with a solution of ethyl 3-((2-(pyridin-2-yl)-6-(1,2,4,5-tetrahydro-3H-benzo[d]azepin-3-yl)pyrimidin-4-yl)amino)propanoate in methanol (0.9 g, 2.156 mmol in 1 mL). Tetrahydrofuran (3 mL) and an aqueous solution of lithium hydroxide (0.215 g 5.39 mmol in 3 mL) were added, and the contents were heated at 80° C. for 14 h. The reaction mixture was concentrated under reduced pressure and the crude mixture was azeotropically dried with toluene twice (2×20 mL). The crude mixture was carefully acidified with concentrated hydrochloric acid until the pH was 5. The reaction mixture was concentrated under reduced pressure and the pale-yellow solid was azeotropically dried with toluene three time (3×30 mL). The crude mixture was taken to the next step without purification.

An oven dried round bottom flask was charged with pale yellow powder from the previous step (0.56 g, 1.34 mmol) Anhydrous N,N-dimethyl formamide (2 mL), DIPEA (0.93 mL, 5.36 mmol), O-benzylhydroxylamine hydrochloride (0.43 g, 2.68 mmol) and HATU (0.764 g, 2 mmol) were sequentially added and the contents were stirred at room temperature for 14 h. The reaction mixture was concentrated under reduced pressure and the crude mixture was redissolved in ethyl acetate (30 mL) and washed with half saturated brine (2×10 mL), dried over anhydrous sodium sulphate, filtered and concentrated under reduced pressure. The crude mixture was purified by column chromatography on alumina (0% to 10% methanol in ethyl acetate) to yield 0.65 g (66%) of N-(benzyloxy)-3-((2-(pyridin-2-yl)-6-(1,2,4,5-tetrahydro-3H-benzo[d]azepin-3-yl)pyrimidin-4-yl)amino)propanamide as half white solid.

$^{1}H$ NMR (400 MHz, $CDCl_3$): δ 8.62 (d, J=2.8 Hz, 1H), 8.39 (d, J=7.6 Hz, 1H), 7.71 (t, J=8.4 Hz, 1H), 7.39=7.13 (m, 6H), 7.12 (s, 4H), 5.89-5.61 (m, 1H), 4.91-4.71 (m, 2H), 3.95 (s, 4H), 3.86 (s, 2H), 2.96 (s, 4H), 2.48 (s, 2H).

$^{13}C$ NMR (125 MHz, $CDCl_3$): δ 170.19, 163.68, 162.64, 161.72, 155.75, 149.89, 141.52, 137.41, 136.36, 130.73, 130.25, 129.84, 129.07, 127.19, 125.32, 124.07, 81.48, 78.70, 48.17, 39.32, 37.55, 34.82.

LC-MS (APCI) m/z (M+H+) Calcd for $C_{29}H_{31}N_6O_2$: 495.24. Found: 495.19.

Synthesis of N-hydroxy-3-((2-(pyridin-2-yl)-6-(1,2,4,5-tetrahydro-3H-benzo[d]azepin-3-yl)pyrimidin-4-yl)amino)propenamide (UR-96)

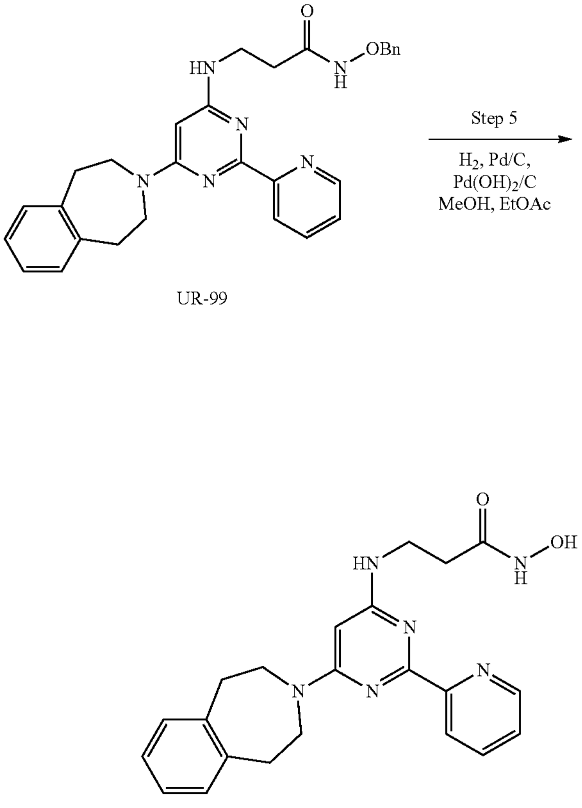

UR-99

UR-96

An oven dried round bottom flask was charged with a solution of N-(benzyloxy)-3-((2-(pyridin-2-yl)-6-(1,2,4,5-tetrahydro-3H-benzo[d]azepin-3-yl)pyrimidin-4-yl)amino)propanamide in 1:1 mixture of methanol (and ethyl acetate 0.1 g in 2 mL). 10% Palladium on carbon (30 mg) and 20% palladium hydroxide on carbon (18 mg) were added and the contents were stirred in an atmosphere of hydrogen for 2 days. The reaction was diluted with methanol (10 mL) and carefully filtered. The filtrate was concentrated under reduced pressure to yield 46 mg of N-hydroxy-3-((2-(pyridin-2-yl)-6-(1,2,4,5-tetrahydro-3H-benzo[d]azepin-3-yl)pyrimidin-4-yl)amino)propanamide as pale yellow solid.

$^{1}H$ NMR (500 MHz, $CD_3OD$): δ 8.61 (bs, 1H), 8.35 (d, J=10 Hz, 1H), 7.91-7.81 (m, 1H), 7.46-7.35 (m, 1H), 7.14-6.94 (m, 4H), 5.66 (s, 1H), 4.89 (bs, 1H), 3.98-3.78 (m, 4H), 3.76-3.56 (m, 2H), 2.93-2.83 (m, 4H), 2.53-2.35 (m, 2H).

$^{13}C$ NMR (125 MHz, $CD_3OD$): δ 170.50, 164.32, 162.83, 162.05, 156.25, 149.06, 141.53, 138.86, 130.23, 126.74, 125.27, 124.23, 81.22, 53.72, 38.18, 36.98, 33.59.

LC-MS (APCI) m/z (M+H+) Calcd for $C_{22}H_{25}N_6O_2$: 405.20. Found: 405.15.

Example 12
Synthesis of 3-((2-(pyridin-2-yl)-6-(1,2,4,5-tetrahydro-3H-benzo[d]azepin-3-yl)pyrimidin-4-yl)amino)propyl 3-(2-(2-ethoxyethoxy)ethoxy)propanoate
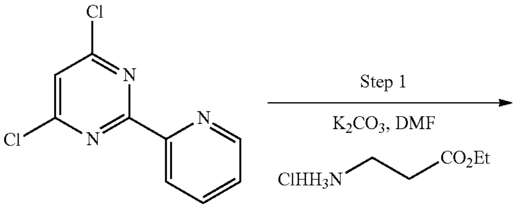
1
4
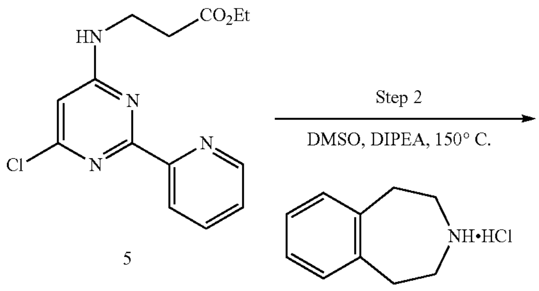
5
2
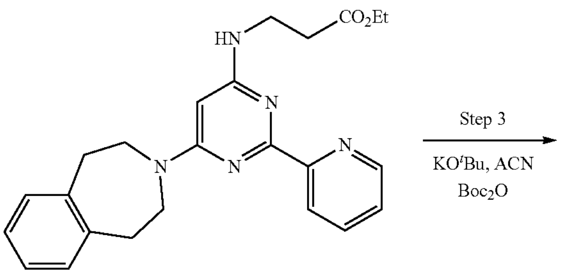
6
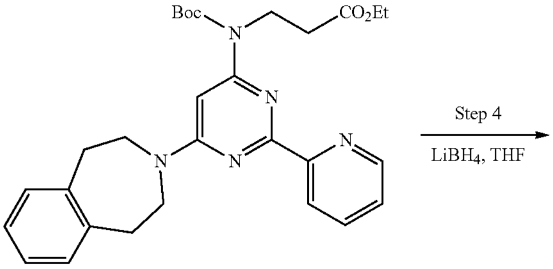
7
-continued
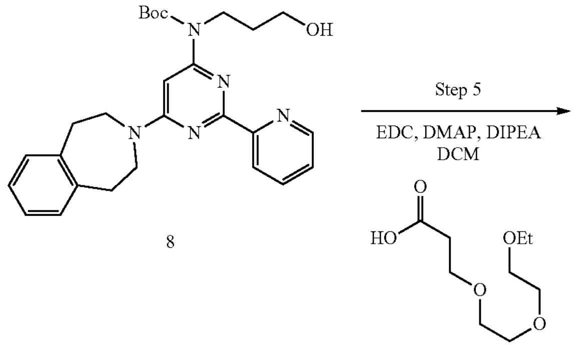
8
9
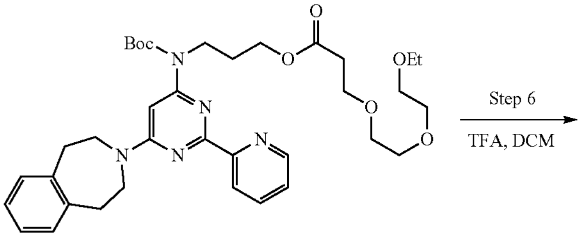
10
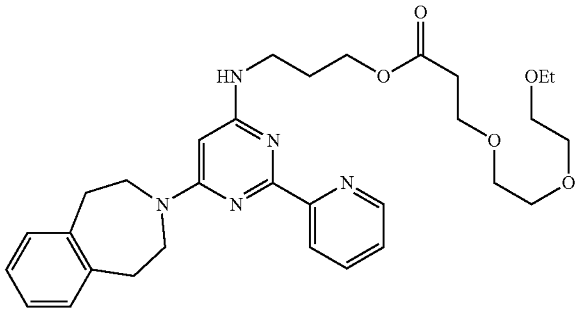
UR-98
Synthesis of ethyl 3-((tert-butoxycarbonyl)(2-(pyridin-2-yl)-6-(1,2,4,5-tetrahydro-3H-benzo[d]azepin-3-yl)pyrimidin-4-yl)amino)propanoate
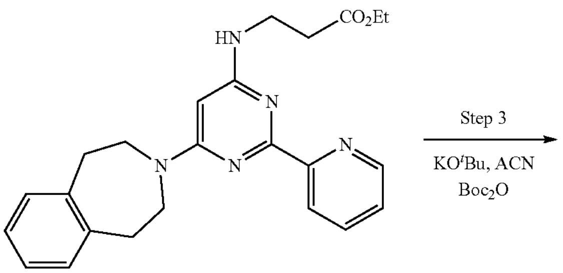
6

-continued

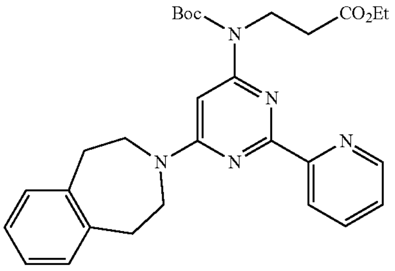

7

An oven dried round bottom flask was charged with a solution of ethyl 3-((2-(pyridin-2-yl)-6-(1,2,4,5-tetrahydro-3H-benzo[d]azepin-3-yl)pyrimidin-4-yl)amino)propanoate in acetonitrile (1.4 g, 3.35 mmol in 4 mL) Potassium tert-butoxide (25 mg) and di-tert-butyl dicarbonate (2.19 g, 10.06 mmol) were added sequentially and the contents were heated at 80° C. for 8 h. The reaction mixture was diluted with ethyl acetate (100 mL) and washed with half saturated brine (2×40 mL), dried over sodium sulphate, filtered and concentrated under reduced pressure. The crude mixture was purified by column chromatography on alumina (0% to 25% ethyl acetate in n-hexanes) to yield 0.96 g (55%) of ethyl 3-((tert-butoxycarbonyl)(2-(pyridin-2-yl)-6-(1,2,4,5-tetrahydro-3H-benzo[d]azepin-3-yl)pyrimidin-4-yl)amino)propanoate as pale yellow oil.

$^{1}$H NMR (500 MHz, $CDCl_3$): δ) 8.76 (d, J=5 Hz, 1H), 8.36 (s, J=5 Hz 1H), 7.77 (dd, $J_1$=5 Hz, $J_2$=10 Hz, 1H), 7.32 (dd, $J_1$=5 Hz, $J_2$=10 Hz, 1H), 7.11 (s, 4H), 4.39 (t, J=8 Hz, 2H), 4.06 (q, J=8 Hz, 2H), 3.97 (s, 4H), 3.05-2.95 (m, 4H), 2.74 (t, J=8 Hz, 2H), 1.54 (s, 9H), 1.17 (t, J=8 Hz, 3H).

$^{13}$C NMR (125 MHz, $CDCl_3$): δ 172.63, 163.84, 162.74, 161.27, 156.63, 154.22, 150.27, 141.52, 137.34, 130.70, 127.19, 124.95, 124.45, 94.76, 82.58, 61.10, 48.27, 42.97, 37.71, 35.00, 29.08, 14.88.

LC-MS (APCI) m/z (M+H$^+$) Calcd for $C_{29}H_{36}N_5O_4$: 518.27. Found: 518.21.

Synthesis of tert-butyl (3-hydroxypropyl)(2-(pyridin-2-yl)-6-(1,2,4,5-tetrahydro-3H-benzo[d]azepin-3-yl)pyrimidin-4-yl)carbamate

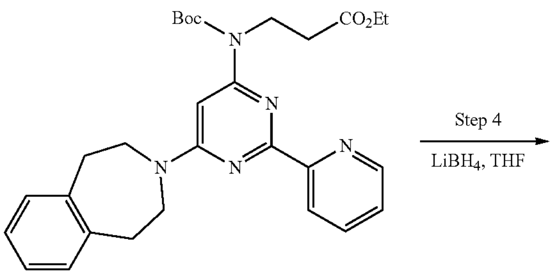

7

-continued

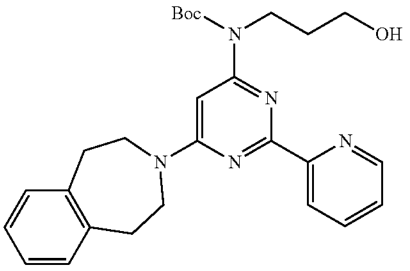

8

An oven dried round bottom flask was charged with a solution of ethyl 3-((tert-butoxycarbonyl)(2-(pyridin-2-yl)-6-(1,2,4,5-tetrahydro-3H-benzo[d]azepin-3-yl)pyrimidin-4 yl)amino)propanoate in anhydrous diethyl ether (0.95 g, 1.88 mmol in 10 mL). A 4 M solution of lithium borohydride in tetrahydrofuran (0.24 mL, 0.943 mmol) was added and the contents were stirred at room temperature for 8 h. The reaction mixture was quenched with 10 mL of methanol and the contents were concentrated under reduced pressure. The crude mixture was purified by column chromatography on alumina (0% to 90% ethyl acetate in n-hexanes) to yield 0.585 g (67%) of tert-butyl (3-hydroxypropyl)(2-(pyridin-2-yl)-6-(1,2,4,5-tetrahydro-3H-benzo[d]azepin-3-yl)pyrimidin-4-yl)carbamate as white foam.

$^{1}$H NMR (500 MHz, $CDCl_3$): δ 8.76 (d, J=5 Hz, 1H), 8.48 (d, j=10 Hz 1H), 7.89-7.74 (m, 1H), 7.39-7.32 (m, 1H), 7.24 (s, 1H), 7.13 (s, 4H), 4.28-4.18 (m, 2H), 4.03-3.85 (m, 4H), 3.75-3.63 (m, 2H), 3.07-2.93 (m, 4H), 1.96-1.85 (m, 2H), 1.54 (s, 9H), $^{13}$C NMR (125 MHz, $CDCl_3$): δ 163.34, 162.47, 161.37, 155.29, 154.67, 149.53, 141.43, 138.06, 130.77, 127.25, 125.62, 123.90, 93.27, 82.48, 58.41, 48.33, 43.48, 37.61, 33.60, 29.10.

LC-MS (APCI) m/z (M+H$^+$) Calcd for $C_{27}H_{33}N_5O_3$: 476.26. Found: 476.21.

Synthesis of 3-((tert-butoxycarbonyl)(2-(pyridin-2-yl)-6-(1,2,4,5-tetrahydro-3H-benzo[d]azepin-3-yl) pyrimidin-4-yl)amino)propyl 3-(2-(2-ethoxyethoxy) ethoxy)propanoate

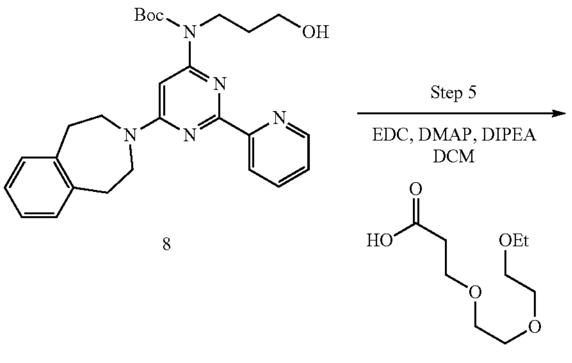

8

9

-continued

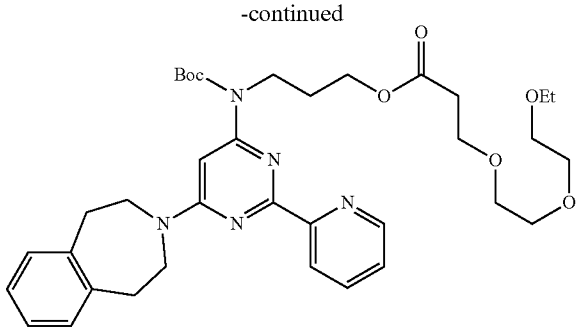

10

An oven dried round bottom flask was charged with a solution of tert-butyl (3-hydroxypropyl)(2-(pyridin-2-yl)-6-(1,2,4,5-tetrahydro-3H-benzo[d]azepin-3-yl)pyrimidin-4-yl)carbamate in dichloromethane (0.1 g, 0.21 mmol in 0.6 mL). DMAP (26 mg, 0.21 mmol), DIPEA (0.08 mL 0.45 mmol) and 3-(2-(2-ethoxyethoxy)ethoxy)propanoic acid (61 mg, 0.295 mmol) were added sequentially. After cooling to 0° C., EDC (70 mg, 0.365 mmol) was added, and the contents were warmed to room temperature and stirred overnight. The reaction mixture was concentrated under reduced pressure and the crude mixture was purified by column chromatography on alumina (0% to 80% ethyl acetate in n-hexanes) to yield 0.1 g (67%) of 3-((tert-butoxycarbonyl)(2-(pyridin-2-yl)-6-(1,2,4,5-tetrahydro-3H-benzo[d]azepin-3-yl)pyrimidin-4-yl)amino)propyl 3-(2-(2-ethoxyethoxy)ethoxy)propanoate as colorless viscous oil.

$^1$H NMR (500 MHz, $CDCl_3$): δ8.78 (d, J=5 Hz, 1H), 8.36 (d, J=10 Hz, 1H), 7.81 (t, J=10 Hz, 1H), 7.17-7.11 (m, 1H), 7.10-7.01 (m, 5H), 4.29-4.17 (m, 4H), 4.03-3.86 (m, 4H), 3.67 (t, J=10 Hz, 2H), 3.62-3.43 (m, 10H), 3.08-2.95 (m, 4H), 2.53 (t, J=10 Hz, 2H), 2.09-1.98 (m, 2H), 1.54 (s, 9H), 1.25 (t, J=10 Hz, 3H).

$^{13}$C NMR (125 MHz, $CDCl_3$): δ172.26, 163.81, 162.63, 161.48, 156.54, 154.46, 150.26, 141.54, 137.46, 141.54, 137.46, 130.70, 127.18, 124.97, 124.36, 94.82, 82.37, 71.40, 71.21, 71.11, 70.54, 67.34, 67.26, 63.46, 48.27, 43.93, 37.31, 35.72, 29.10, 29.05, 15.88.

LC-MS (APCI) m/z (M+H$^+$) Calcd for $C_{36}H_{50}N_5O_7$: 664.36. Found: 664.31.

Synthesis of 3-((2-(pyridin-2-yl)-6-(1,2,4,5-tetrahydro-3H-benzo[d]azepin-3-yl)pyrimidin-4-yl)amino)propyl 3-(2-(2-ethoxyethoxy)ethoxy)propanoate

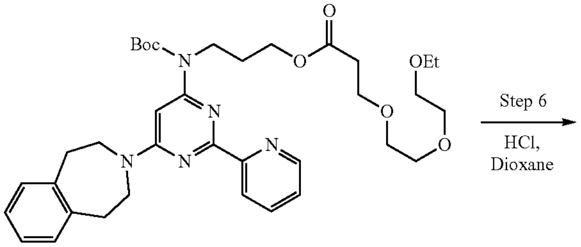

10

-continued

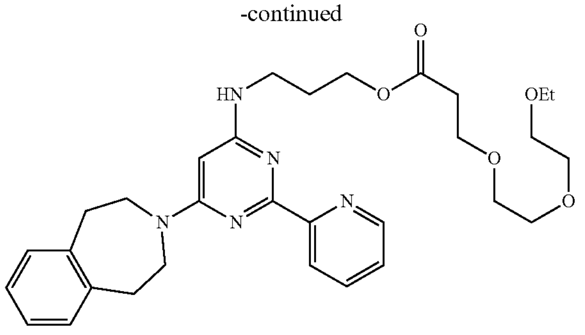

UR-98

An oven dried round bottom flask was charged with a solution of 3-((tert-butoxycarbonyl)(2-(pyridin-2-yl)-6-(1,2,4,5-tetrahydro-3H-benzo[d]azepin-3-yl)pyrimidin-4-yl)amino)propyl 3-(2-(2-ethoxyethoxy)ethoxy)propanoate in dichloromethane (140 mg, 0.21 mmol in 1 mL). A solution of hydrogen chloride in dioxane (0.15 mL, 0.6 mmol, 4N) was added and the contents were stirred at room temperature for 3 h. The reaction mixture was concentrated under reduced pressure. The crude mixture was redissolved in dichloromethane (10 mL) and washed with an aqueous solution of sodium bicarbonate (2x3 mL), brine (1x5 mL), dried over sodium sulphate, filtered and concentrated under reduced pressure. The crude mixture was purified by column chromatography on alumina (0% to 2% methanol in ethyl acetate) to yield 87 mg (73%) of 3-((2-(pyridin-2-yl)-6-(1,2,4,5-tetrahydro-3H-benzo[d]azepin-3-yl)pyrimidin-4-yl)amino)propyl 3-(2-(2-ethoxyethoxy)ethoxy)propanoate as half white solid.

$^1$H NMR (400 MHz, $CDCl_3$): δ8.76 (d, J=4 Hz, 1H), 8.43 (d, J=8 Hz, 1H), 7.85-7.76 (m, 1H), 7.37-7.28 (m, 1H), 7.19 (s, 4H), 5.50 (s, 1H), 5.16 (bs, 1H), 4.24 (t, J=6 Hz, 2H), 3.99-3.85 (m, 4H), 3.77 (t, J=6.4 Hz, 2H), 3.69-3.44 (m, 8H), 3.42-3.29 (m, 2H), 3.09-2.95 (m, 2H), 2.09-1.91 (m, 2H), 1.17 (t, J=8 Hz, 3H)

$^{13}$C NMR (125 MHz, $CDCl_3$): δ 172.28, 164.76, 163.17, 162.91, 156.75, 150.24, 141.63, 137.16, 130.71, 127.17, 124.87, 124.15, 79.95, 71.41, 71.24, 71.18, 70.53, 67.34, 62.72, 54.17, 48.15, 39.50, 37.64, 35.83, 29.19, 15.88.

LC-MS (APCI) m/z (M+H$^+$) Calcd for $C_{36}H_{50}N_5O_7$: 564.31. Found: 564.26.

All references cited herein are incorporated herein by reference in their entireties. It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

We claim:

1. A compound or a pharmaceutically acceptable salt thereof, wherein the compound is represented by Formula I,

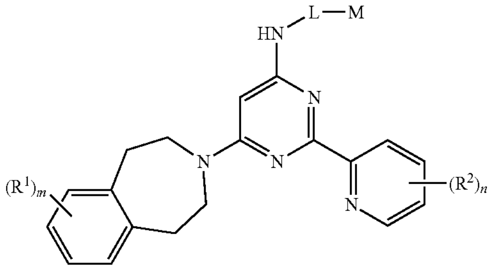

Wherein:

L is a linker selected from the group consisting of $C_{1-6}$alkylene, $C_{2-6}$alkenylene, and $C_{2-6}$alkynlene, each of which is optionally substituted with one or more substituents selected from $C_{1-6}$alkyl, halo$C_{1-6}$alkyl, halogen, wherein two or more $C_{1-6}$alkyl substituents optionally link up to form a 3-6 membered ring;

M is selected from the group consisting of $OR^a$, $C(O)R^b$, 3-6 membered cycloalkylnone, 4-6 membered lactam, and 4-6 membered lactone;

$R^a$ is selected from the group consisting of H, $C_{1-6}$alkyl, halo$C_{1-6}$alkyl, $C(O)C_{1-6}$alkyl, $C(O)C_{1-4}$alkylene-$(OC_{2-4}$ alkylene$)_p$-$OC_{1-4}$alkyl;

$R^b$ is selected from the group consisting of halo$C_{1-4}$alkyl, $C_{1-4}$alkylene-OH, $NR^cR^d$;

$R^c$ is H or $C_{1-4}$alkyl;

$R^d$ is OH, $OC_{1-6}$alkyl, $OC_{1-4}$alkylene$C_{6-10}$aryl, $OC_{1-4}$alkylene$C_{5-10}$heteroaryl, $C_{6-10}$aryl, or $C_{5-10}$heteroaryl, wherein the $C_{6-10}$aryl or $C_5$-10heteroaryl is optionally substituted with one or more substituents selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$;

each $R^e$ is independently H or $C_{1-4}$alkyl;

each $R^1$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

each $R^2$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

m and n are each an integer ranging from 0 to 4; and p is an integer ranging from 1 to 20, provided the compound is not

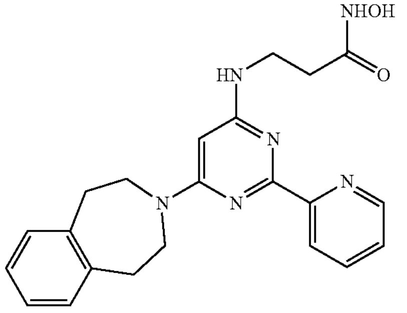

or

-continued

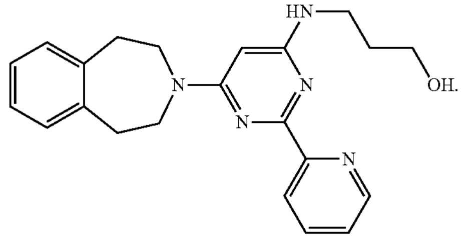

2. The compound or the pharmaceutically acceptable salt thereof of claim 1, wherein M is OH, L is optionally substituted $C_{2-4}$alkylene.

3. The compound or the pharmaceutically acceptable salt thereof of claim 1, wherein M is OH, and L is $C_{2-4}$alkylene substituted with halo$C_{1-6}$alkyl.

4. The compound or the pharmaceutically acceptable salt thereof of claim 3, wherein the halo$C_{1-6}$alkyl is $CF_3$.

5. The compound or the pharmaceutically acceptable salt thereof of claim 1, wherein M is OH, and L is $C_{3-6}$alkylene wherein two substituents of the $C_{3-6}$alkylene link up to form a 3-5 membered carbocyclic ring.

6. The compound or the pharmaceutically acceptable salt thereof of claim 5, wherein the two substituents of the $C_{3-6}$alkylene link up to form a 3 membered carbocyclic ring.

7. The compound or the pharmaceutically acceptable salt thereof of claim 1, wherein L is $C_{2-6}$alkylene, wherein M is selected from the group consisting of $OR^a$, and $R^a$ is $C(O)C_{1-6}$alkyl.

8. The compound or the pharmaceutically acceptable salt thereof of claim 7, wherein $R^a$ is $C(O)_{tert}$butyl.

9. The compound or the pharmaceutically acceptable salt thereof of claim 1, wherein L is $C_{2-6}$alkylene, wherein M is selected from the group consisting of $OR^a$, and $R^a$ is C(O $C_{1-4}$alkylene-$(OC_{2-4}$alkylene$)_p$-$OC_{1-4}$alkyl.

10. The compound or the pharmaceutically acceptable salt thereof of claim 9, wherein p is 1-3.

11. The compound or the pharmaceutically acceptable salt thereof of claim 1, wherein L is $C_{2-6}$alkylene, M is $C(O)R^b$, and $R^b$ is selected from the group consisting of halo$C_{1-4}$alkyl, $C_{1-4}$alkylene-OH, and $NR^cR^d$.

12. The compound or the pharmaceutically acceptable salt thereof of claim 11, wherein $R^c$ is H or $C_{1-4}$alkyl, and $R^d$ is OH or $OC_{1-2}$alkylene$C_6$aryl.

13. The compound or the pharmaceutically acceptable salt thereof of claim 1, wherein L is $C_{2-6}$alkylene, and M is selected from the group consisting of 3-6 membered cycloalkylnone, 4-6 membered lactam, and 4-6 membered lactone.

14. The compound or the pharmaceutically acceptable salt thereof of claim 1, wherein the compound is selected from the group consisting of

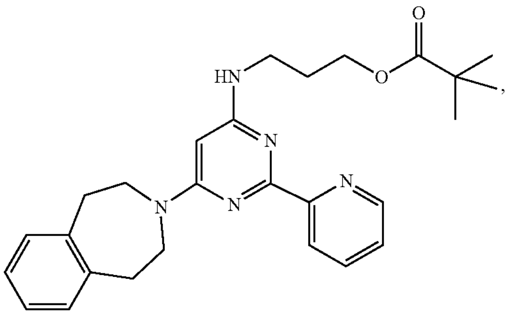
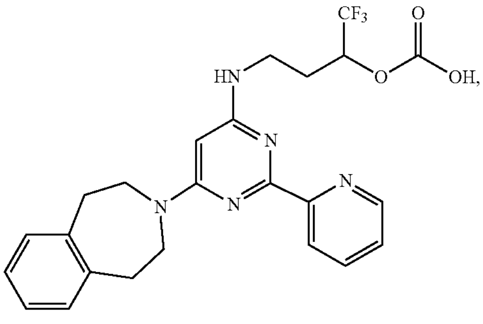
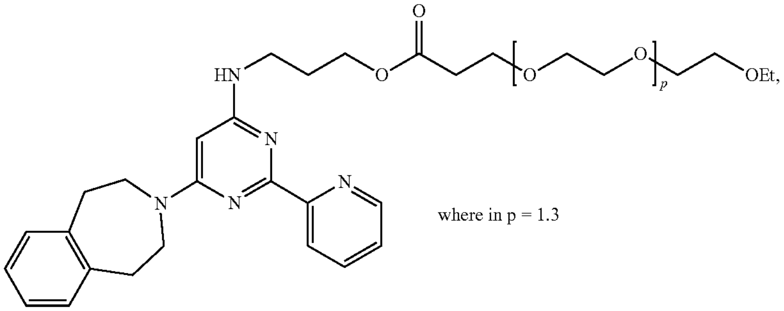
where in p = 1.3
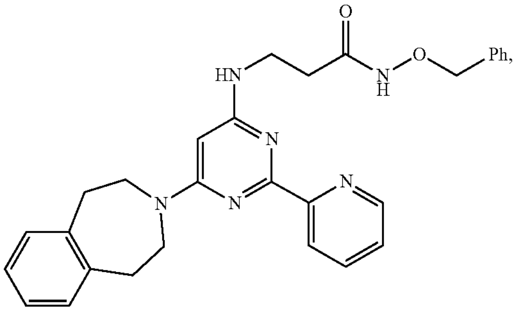
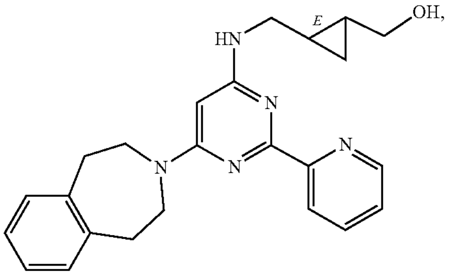
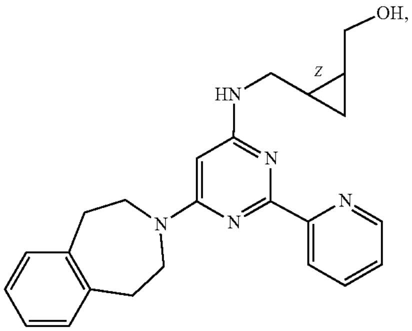
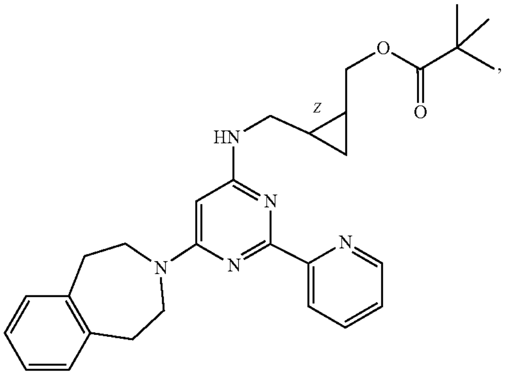
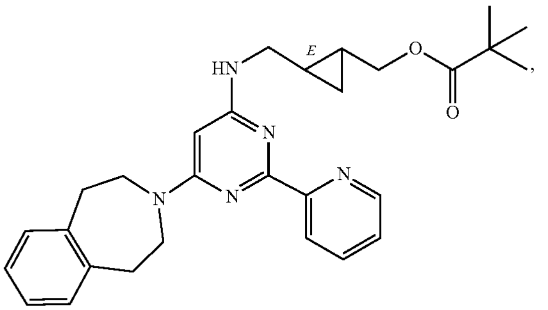
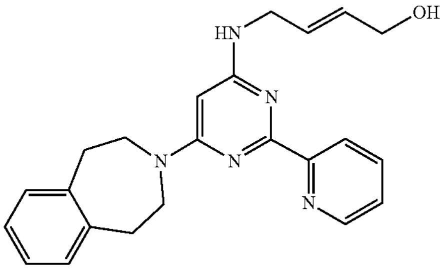

-continued
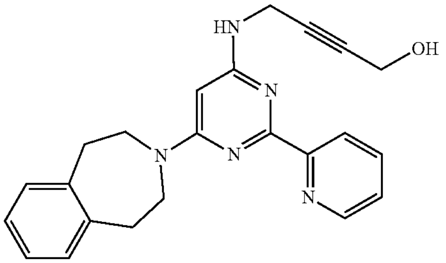
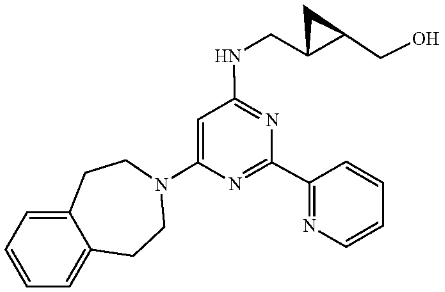
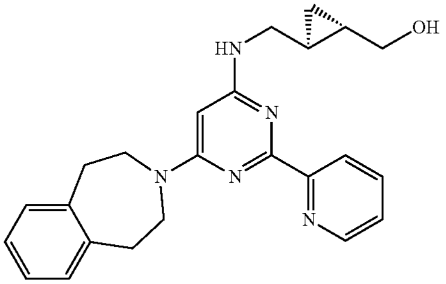
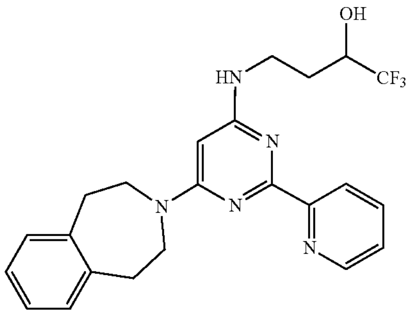
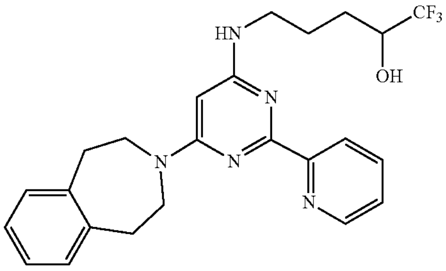
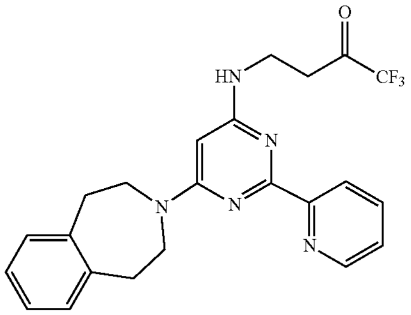
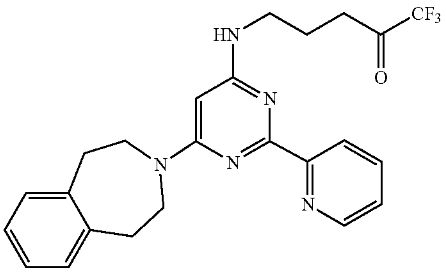
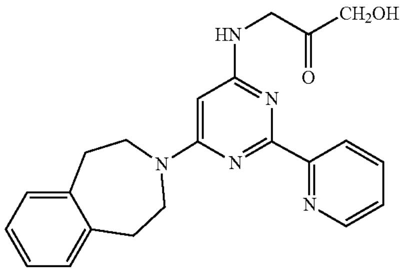
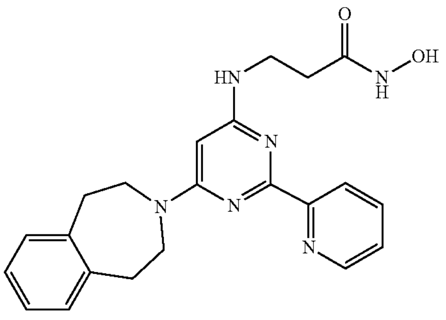
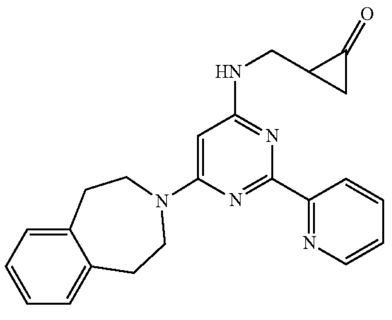

-continued
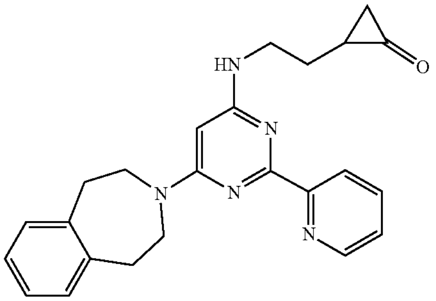
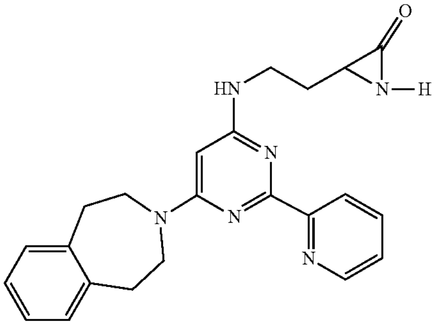
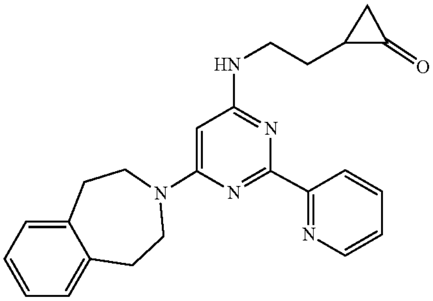
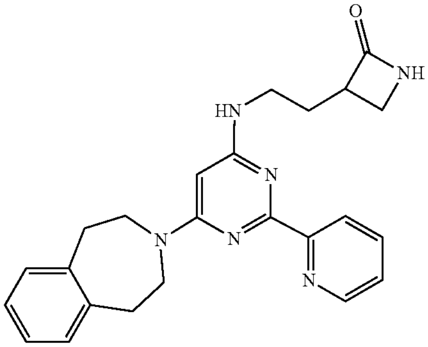
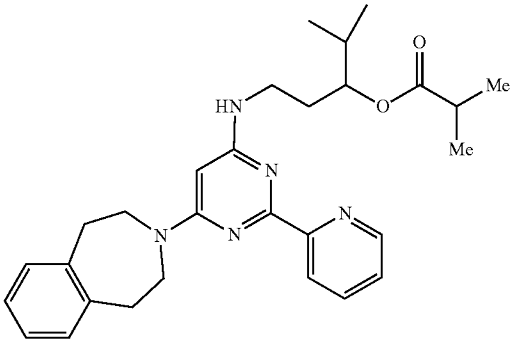
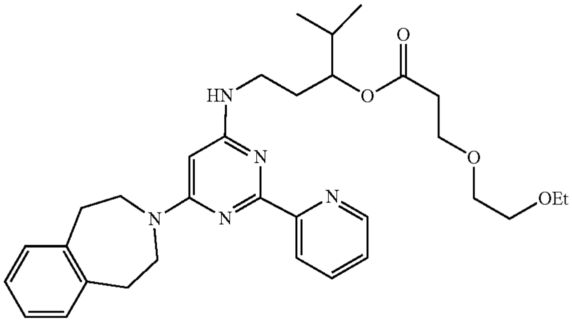
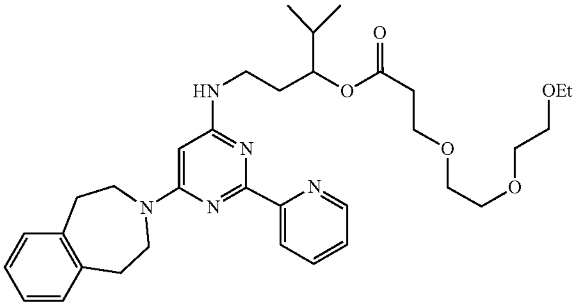
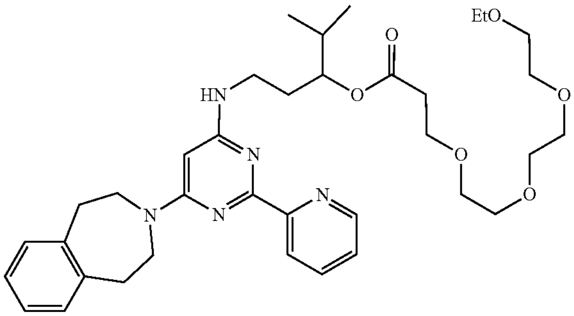
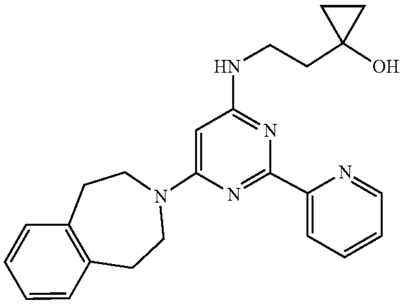

-continued
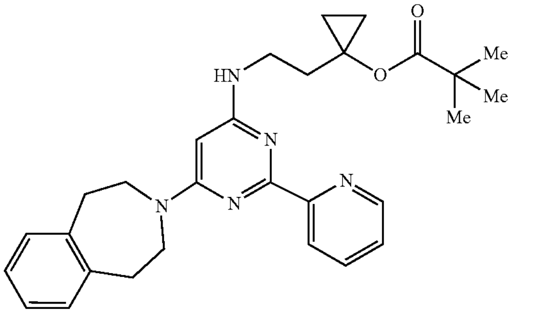
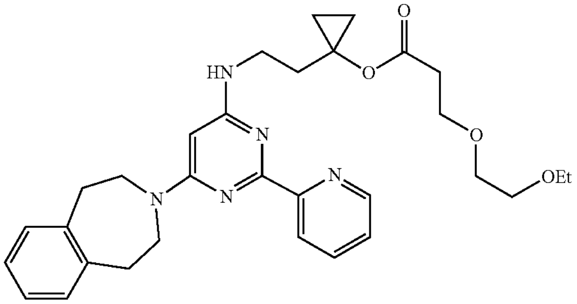
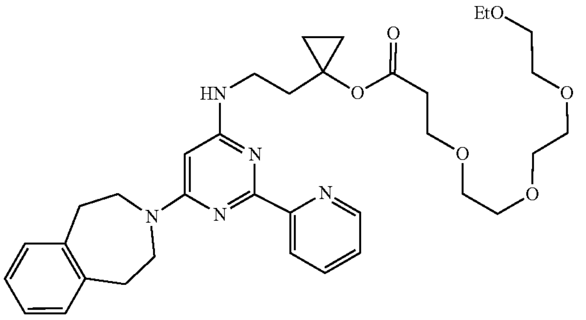
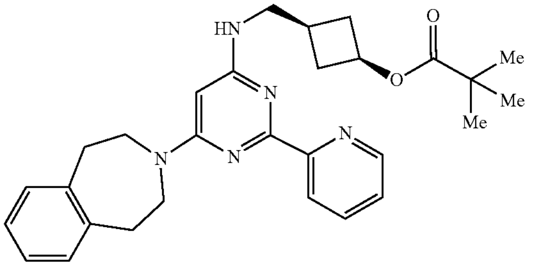
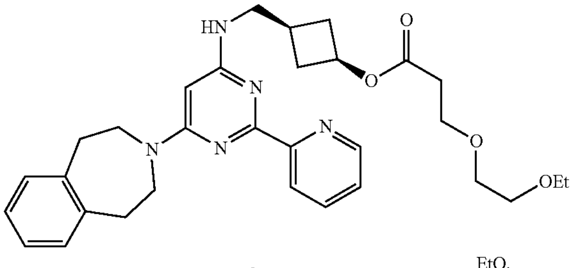
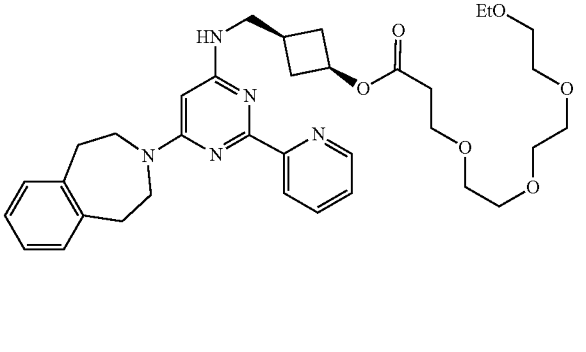
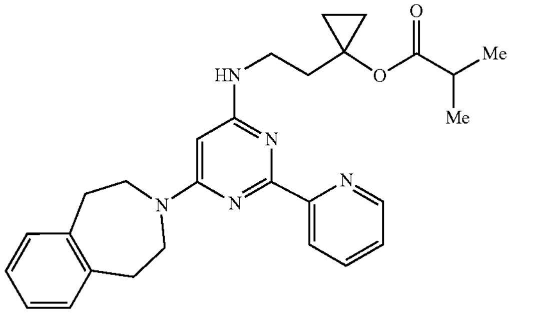
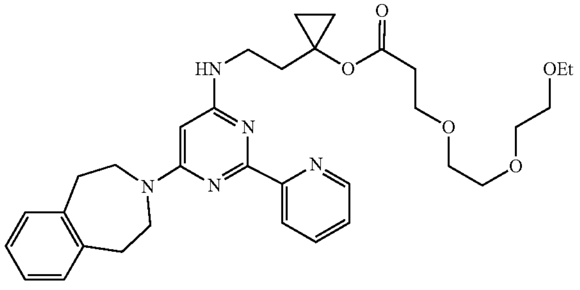
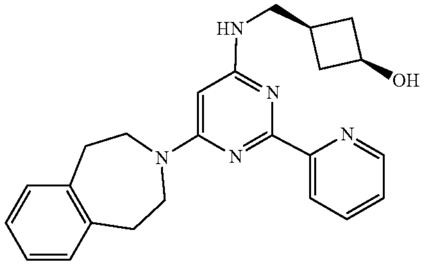
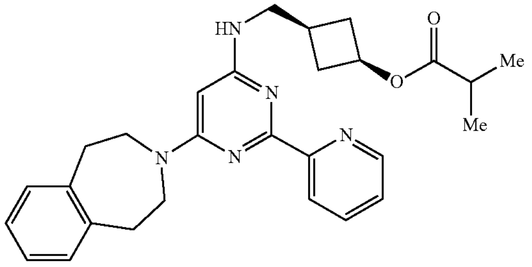
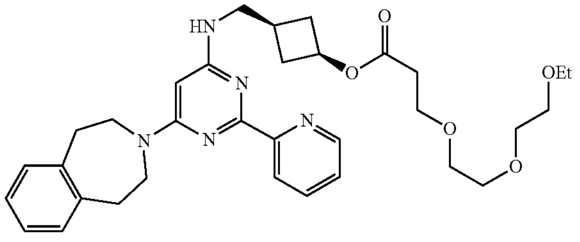
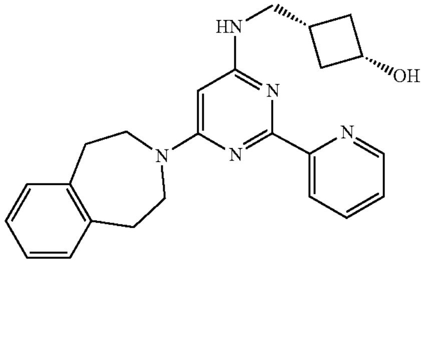

-continued
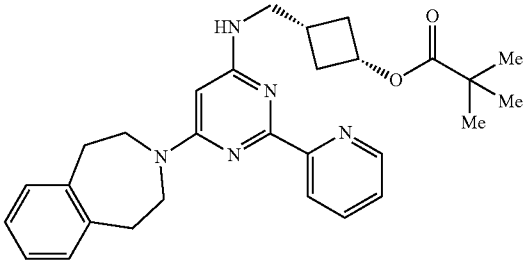
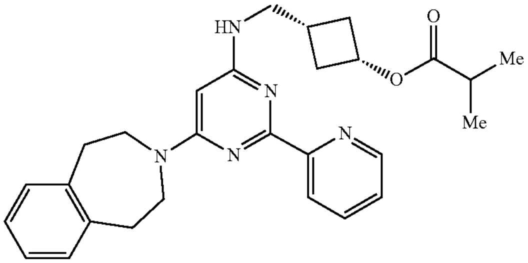
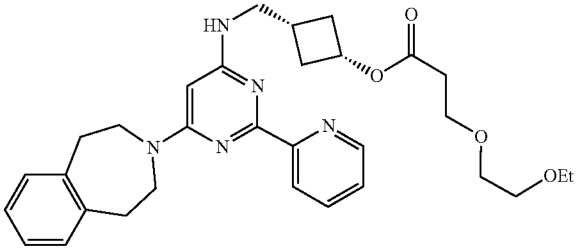
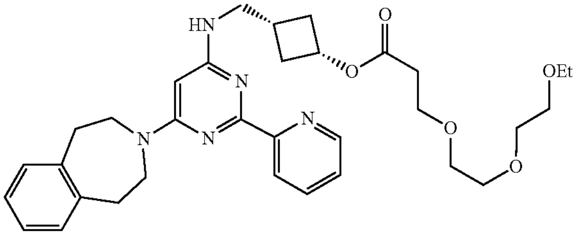
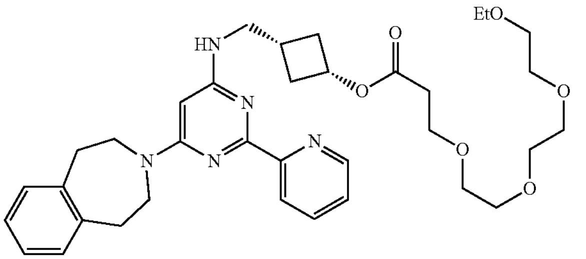
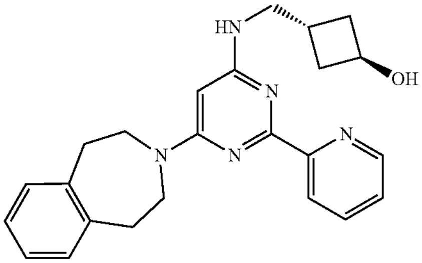
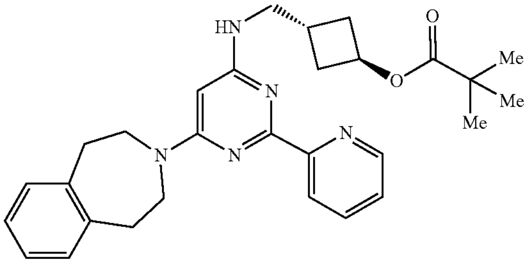
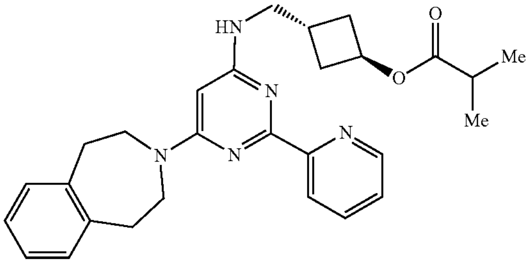
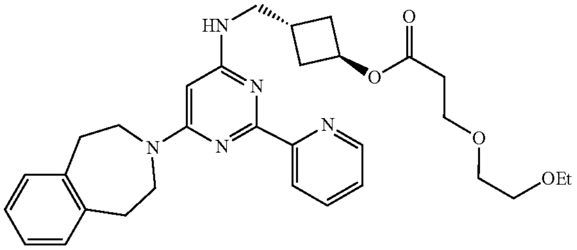
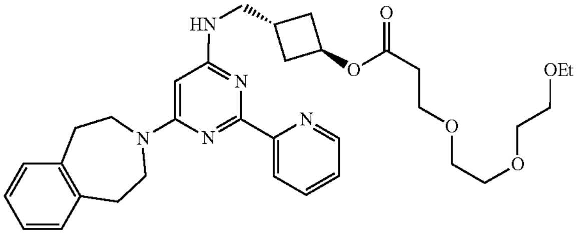
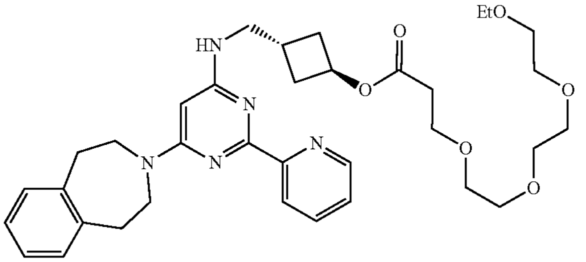
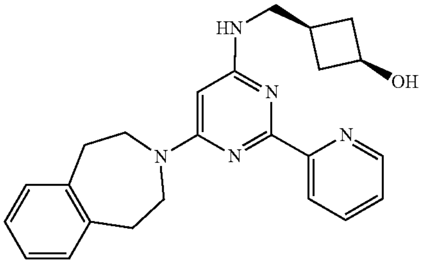

-continued
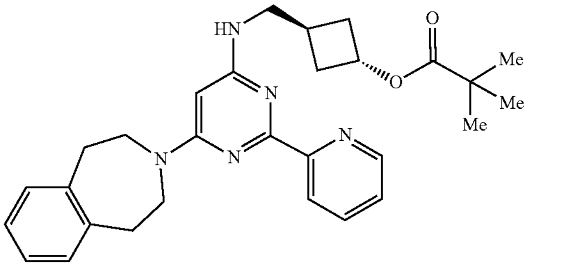
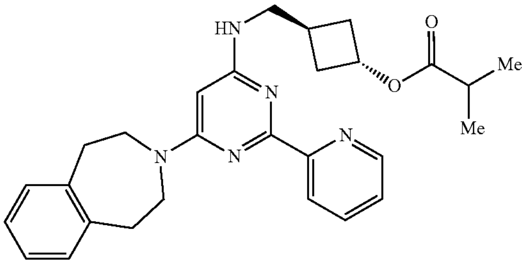
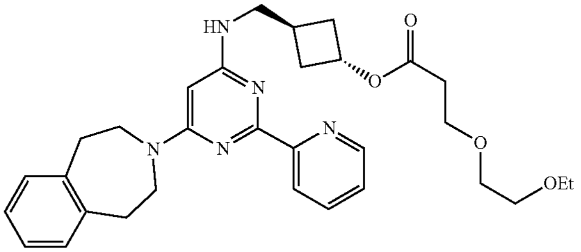
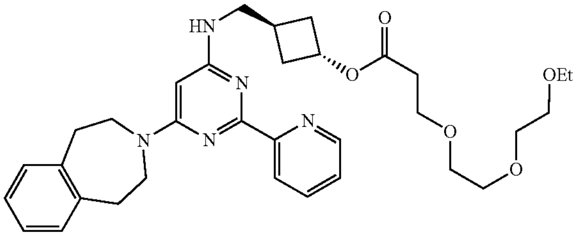
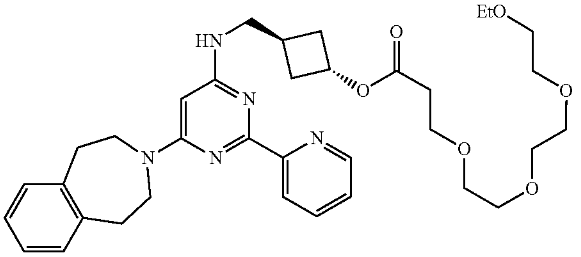
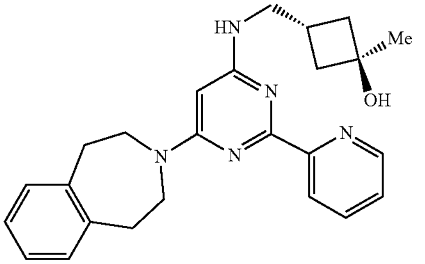
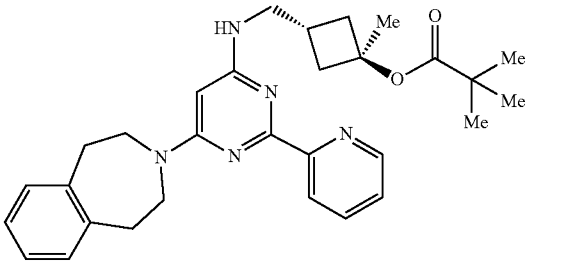
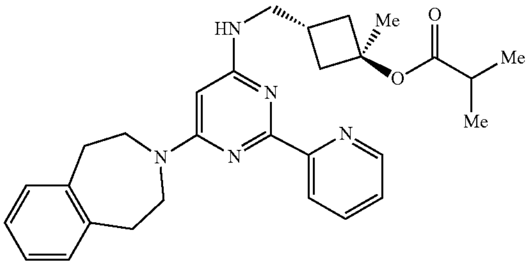
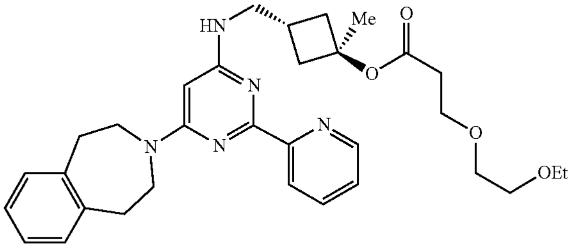
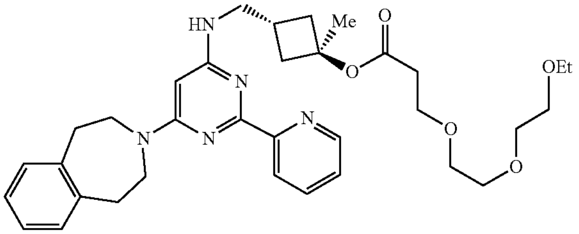
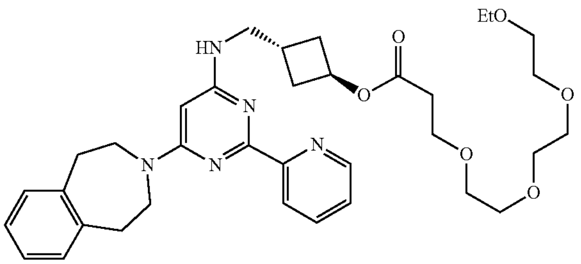
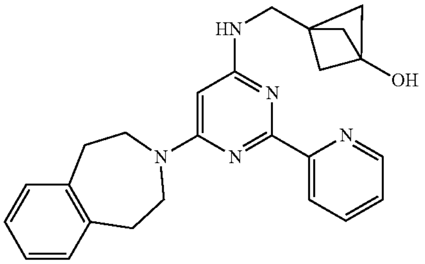

-continued
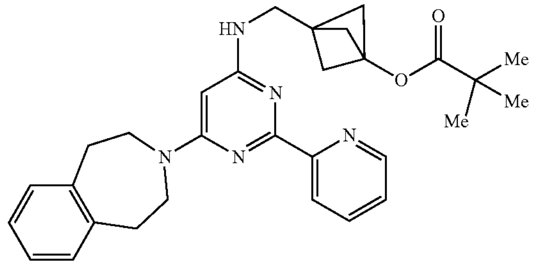
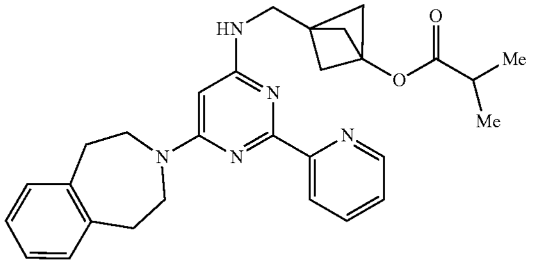
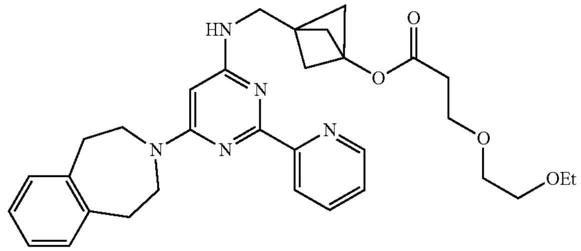
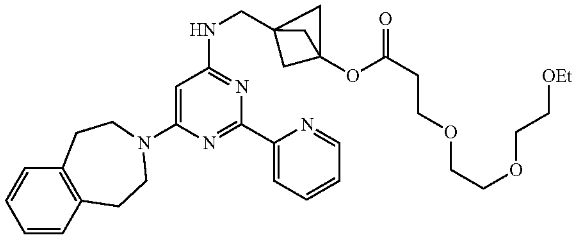
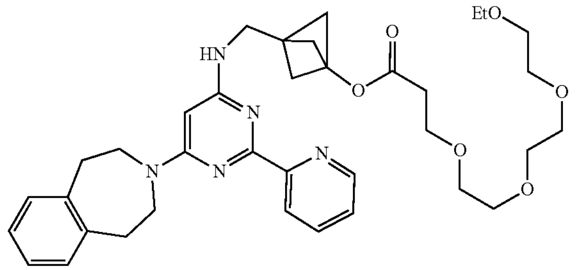
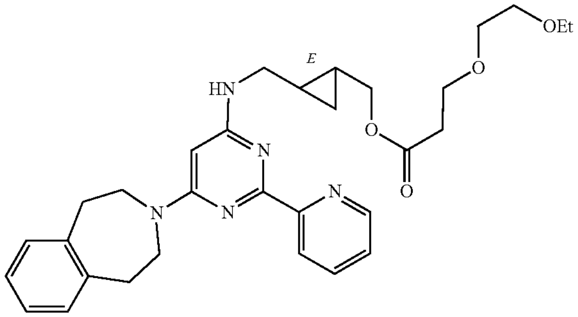
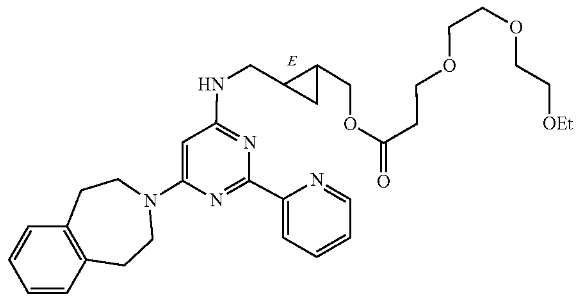
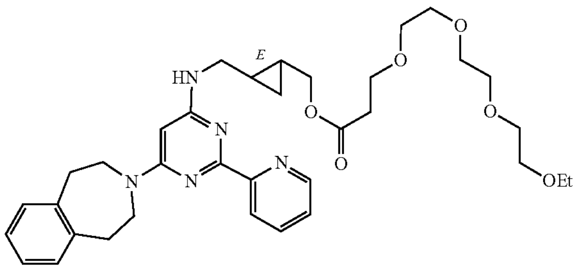
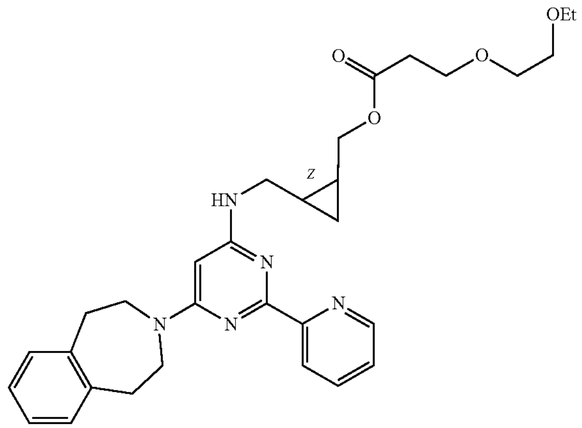
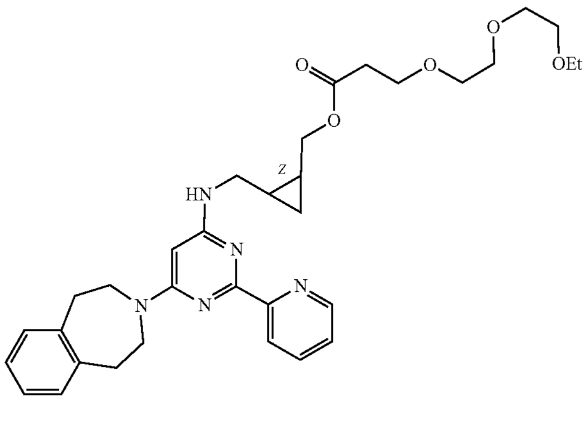

-continued

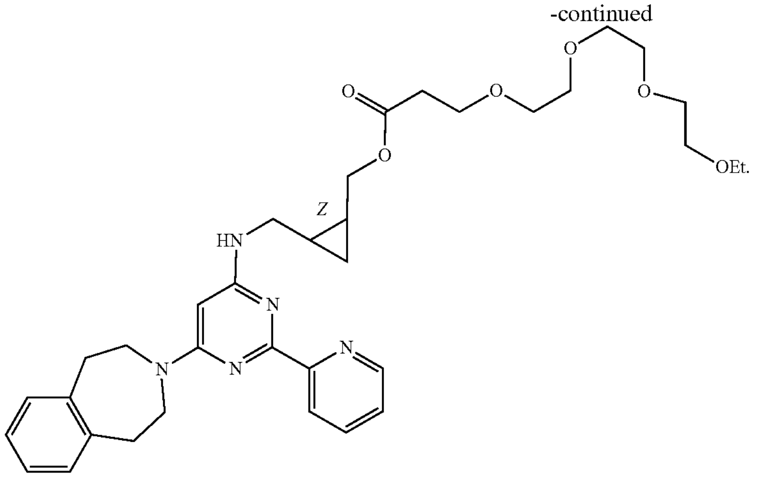

15. The compound or the pharmaceutically acceptable salt thereof of claim 1, wherein the compound is

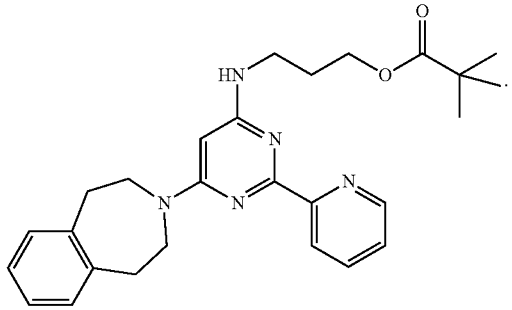 [SMILES: CC(C)(C)C(=O)OCCCNc1cc(N2CCc3ccccc3CC2)nc(-c2ccccn2)n1]

16. The compound or the pharmaceutically acceptable salt thereof of claim 1, wherein the compound is

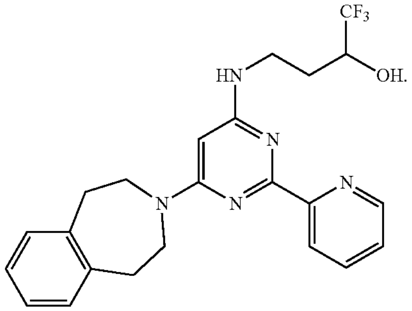 [SMILES: OC(CCNc1cc(N2CCc3ccccc3CC2)nc(-c2ccccn2)n1)C(F)(F)F]

17. The compound or the pharmaceutically acceptable salt thereof of claim 1, wherein the compound is

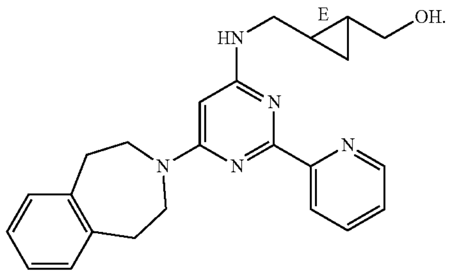 [SMILES: OCC1CC1CNc1cc(N2CCc3ccccc3CC2)nc(-c2ccccn2)n1]

18. The compound or the pharmaceutically acceptable salt thereof of claim 1, wherein the compound is

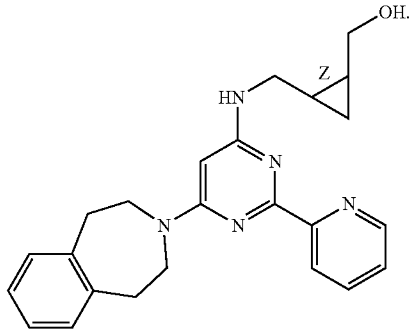 [SMILES: OCC1CC1CNc1cc(N2CCc3ccccc3CC2)nc(-c2ccccn2)n1]

19. The compound or the pharmaceutically acceptable salt thereof of claim 1, wherein the compound is

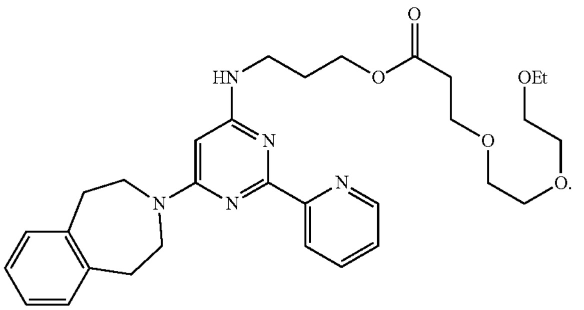 [SMILES: CCOCCOCCOCCC(=O)OCCCNc1cc(N2CCc3ccccc3CC2)nc(-c2ccccn2)n1]

20. The compound or the pharmaceutically acceptable salt thereof of claim 1, wherein the compound is

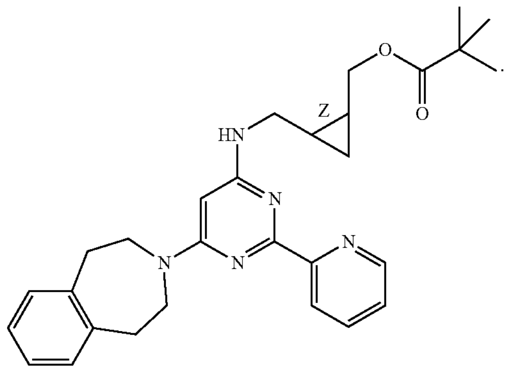 [SMILES: CC(C)(C)C(=O)OCC1CC1CNc1cc(N2CCc3ccccc3CC2)nc(-c2ccccn2)n1]

21. A pharmaceutical formulation comprising a therapeutically effective amount of the compound or the pharmaceutically acceptable salt thereof of claim 1 and a pharmaceutically acceptable carrier.

22. A method of treating a disease in a subject, comprising administering to the subject a therapeutically effective amount of a compound of Formula I or a pharmaceutically acceptable salt thereof, wherein the disease is diffuse intrinsic pontine glioma (DIPG), wherein the compound is represented by Formula I, Formula I

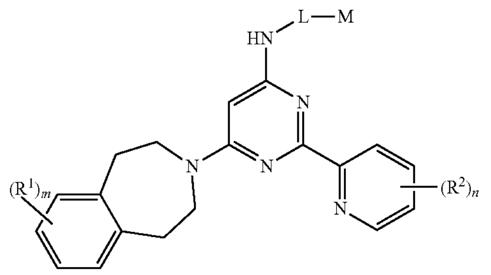

Wherein:

L is a linker selected from the group consisting of $C_{1-6}$alkylene, $C_{2-6}$alkenylene, and $C_{2-6}$alkynlene, each of which is optionally substituted with one or more substituents selected from $C_{1-6}$alkyl, halo$C_{1-6}$alkyl, halogen, wherein two or more $C_{1-6}$alkyl substituents optionally link up to form a 3-6 membered ring;

M is selected from the group consisting of $OR^a$, $C(O)R^b$, 3-6 membered cycloalkylnone, 4-6 membered lactam, and 4-6 membered lactone;

$R^a$ is selected from the group consisting of H, $C_{1-6}$alkyl, halo$C_{1-6}$alkyl, C (O) $C_{1-6}$alkyl, $C(O)C_{1-4}$alkylene-$(OC_{2-4}$alkylene$)_p$-$OC_{1-4}$alkyl;

$R^b$ is selected from the group consisting of halo$C_{1-4}$alkyl, $C_{1-4}$alkylene-OH, $NR^cR^d$;

$R^c$ is H or $C_{1-4}$alkyl;

$R^d$ is OH, $OC_{1-6}$alkyl, $OC_{1-4}$alkylene$C_{6-10}$aryl, $OC_{1-4}$alkylene$C_{5-10}$heteroaryl, $C_{6-10}$aryl, or $C_{5-10}$heteroaryl, wherein the $C_{6-10}$aryl or $C_{5-10}$heteroaryl is optionally substituted with one or more substituents selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$;

each $R^e$ is independently H or $C_{1-4}$alkyl;

each $R^1$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

each $R^2$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

m and n are each an integer ranging from 0 to 4; and p is an integer ranging from 1 to 20, provided the compound is not

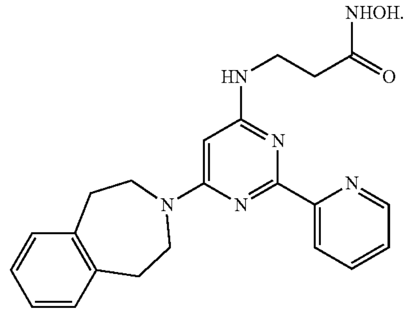

23. A method of treating a disease in a subject, comprising administering to the subject a therapeutically effective amount of a compound of Formula I or a pharmaceutically acceptable salt thereof, wherein the disease is selected from the group consisting of glioblastomas, diffuse intrinsic pontine glioma (DIPG), ependymoma, T-cell acute lymphoblastic leukemia, acute myeloid leukemia, diffuse large B-cell lymphoma, neuroblastoma, prostate cancer, gastric cancer, multiple myeloma, rheumatoid arthritis, other arthritis, and bone metastases, wherein the compound is represented by Formula I, Formula I

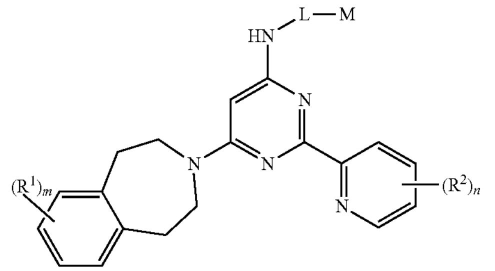

Wherein:

L is a linker selected from the group consisting of $C_{1-6}$alkylene, $C_{2-6}$alkenylene, and $C_{2-6}$alkynlene, each of which is optionally substituted with one or more substituents selected from $C_{1-6}$alkyl, halo$C_{1-6}$alkyl, halogen, wherein two or more $C_{1-6}$alkyl substituents optionally link up to form a 3-6 membered ring;

M is selected from the group consisting of $OR^a$, $C(O)R^b$, 3-6 membered cycloalkylnone, 4-6 membered lactam, and 4-6 membered lactone;

$R^a$ is selected from the group consisting of H, $C_{1-6}$alkyl, halo$C_{1-6}$alkyl, C (O) $C_{1-6}$alkyl, $C(O)C_{1-4}$alkylene-($OC_{2-4}$alkylene)$_p$-$OC_{1-4}$alkyl;

$R^b$ is selected from the group consisting of halo$C_{1-4}$alkyl, $C_{1-4}$alkylene-OH, $NR^cR^d$;

$R^c$ is H or $C_{1-4}$alkyl;

$R^d$ is OH, $OC_{1-6}$alkyl, $OC_{1-4}$alkylene$C_{6-10}$aryl, $OC_{1-4}$alkylene$C_{5-10}$heteroaryl, $C_{6-10}$aryl, or $C_{5-10}$heteroaryl, wherein the $C_{6-10}$aryl or $C_{5-10}$heteroaryl is optionally substituted with one or more substituents selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$;

each $R^e$ is independently H or $C_{1-4}$alkyl;

each $R^1$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

each $R^2$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

m and n are each an integer ranging from 0 to 4; and p is an integer ranging from 1 to 20, provided the compound is not

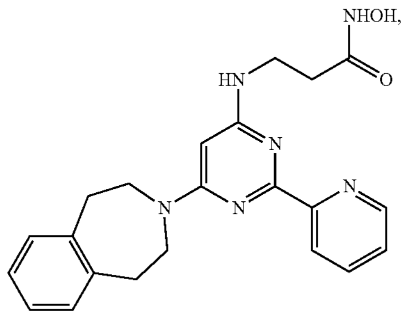

wherein the subjected has been determined to have a mutation selected from the group consisting of mutation of H3K27M, mutation of TP53 (H3.3 and H3.1 K27M-mutant DIPG), and mutation of ACVR1 (H3.1 K27M-mutant DIPG).

24. A method of inhibiting JMJD3 histone H3K27 demethylase, comprising contacting the JMJD3 histone H3K27 demethylase a therapeutically effective amount of a compound of Formula I or a pharmaceutically acceptable salt thereof wherein the compound is represented by Formula I, Formula I

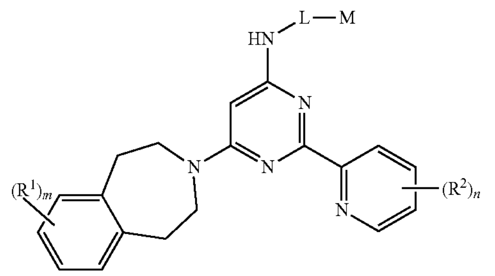

Wherein:

L is a linker selected from the group consisting of $C_{1-6}$alkylene, $C_{2-6}$alkenylene, and $C_{2-6}$alkynlene, each of which is optionally substituted with one or more substituents selected from $C_{1-6}$alkyl, halo$C_{1-6}$alkyl, halogen, wherein two or more $C_{1-6}$alkyl substituents optionally link up to form a 3-6 membered ring;

M is selected from the group consisting of $OR^a$, $C(O)R^b$, 3-6 membered cycloalkylnone, 4-6 membered lactam, and 4-6 membered lactone;

$R^a$ is selected from the group consisting of H, $C_{1-6}$alkyl, halo$C_{1-6}$alkyl, $C(O)C_{1-6}$alkyl, $C(O)C_{1-4}$alkylene-($OC_{2-4}$alkylene)$_p$-$OC_{1-4}$alkyl;

$R^b$ is selected from the group consisting of halo$C_{1-4}$alkyl, $C_{1-4}$alkylene-OH, $NR^cR^d$;

$R^c$ is H or $C_{1-4}$alkyl;

$R^d$ is OH, $OC_{1-6}$alkyl, $OC_{1-4}$alkylene$C_{6-10}$aryl, $OC_{1-4}$alkylene$C_{5-10}$heteroaryl, $C_{6-10}$aryl, or $C_{5-10}$heteroaryl, wherein the $C_{6-10}$aryl or $C_{5-10}$heteroaryl is optionally substituted with one or more substituents selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$;

each $R^e$ is independently H or $C_{1-4}$alkyl;

each $R^1$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

each $R^2$ is independently selected from the group consisting of halogen, acyl, CN, haloalkyl, hydroxyl, $C_{1-6}$alkyl, $OC_{1-6}$alkyl, hydroxy$C_{1-6}$alkyl, carboxamide, amido and $N(R^e)_2$;

m and n are each an integer ranging from 0 to 4; and p is an integer ranging from 1 to 20, provided the compound is not

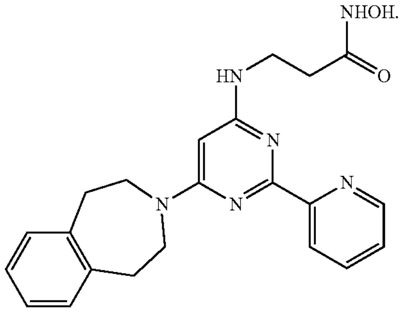

25. The compound or the pharmaceutically acceptable salt thereof of claim 1, wherein $R^d$ is $OC_{1-6}$alkyl, $OC_{1-4}$alkylene$C_{6-10}$aryl, $OC_{1-4}$alkylene$C_{5-10}$heteroaryl, $C_{6-10}$aryl, or $C_5$-10heteroaryl, wherein the $C_{6-10}$aryl or $C_5$-10heteroaryl is optionally substituted with one or more substituents selected from the group consisting of halogen, acyl, CN, haloalkyl, hydroxyl, $C_{1-6}$alkyl, $OC_{1-6}$alkyl, hydroxy$C_{1-6}$alkyl, and $N(R^e)_2$.

26. The method of claim 22, wherein the compound is

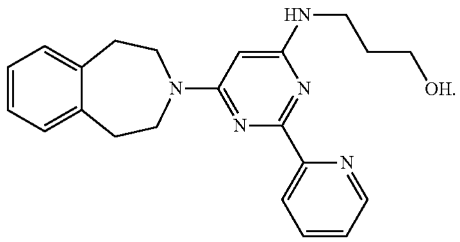 [SMILES: OCCCNc1cc(N2CCc3ccccc3CC2)nc(-c2ccccn2)n1]

* * * * *